US006387690B1

(12) United States Patent
Schülein et al.

(10) Patent No.: US 6,387,690 B1
(45) Date of Patent: *May 14, 2002

(54) ENDOGLUCANASES

(75) Inventors: Martin Schülein, Copenhagen; Lene Nonboe Andersen, Allerød; Søren Flensted Lassen, Copenhagen; Markus Sakari Kauppinen, Copenhagen; Lene Lange, Valby; Ruby Ilum Nielsen, Farum, all of (DK); Michiko Ihara; Shinobu Takagi, both of Chiba (JP)

(73) Assignee: Novozymes A/S, Bagsvaerd (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/229,911

(22) Filed: Jan. 13, 1999

Related U.S. Application Data

(62) Division of application No. 08/651,136, filed on May 21, 1996, now Pat. No. 6,001,639.

(30) Foreign Application Priority Data

| Mar. 17, 1995 | (DK) | 0272/95 |
| Aug. 8, 1995 | (DK) | 0885/95 |
| Aug. 8, 1995 | (DK) | 0886/95 |
| Aug. 8, 1995 | (DK) | 0887/95 |
| Aug. 8, 1995 | (DK) | 0888/95 |
| Feb. 12, 1996 | (DK) | 0137/96 |

(51) Int. Cl.$^7$ .......... D06M 16/00; C12N 9/42; D21C 1/00; C11D 3/386
(52) U.S. Cl. .......... 435/263; 435/209; 435/277; 570/320; 570/321
(58) Field of Search .......... 435/6, 263, 209, 435/277, 91.2; 532/23.2, 24.3; 510/320, 321

(56) References Cited

FOREIGN PATENT DOCUMENTS

| EP | 0307564 | 3/1989 |
| GB | 1368599 | 10/1974 |
| WO | WO 90/02790 | 3/1990 |
| WO | WO 91/10732 | 7/1991 |
| WO | WO 91/17243 | 11/1991 |
| WO | WO 91/17244 | 11/1991 |
| WO | WO 93/20193 | 10/1993 |
| WO | WO 94/07998 | 4/1994 |
| WO | WO 94/21801 | 9/1994 |
| WO | WO 94/26880 | 11/1994 |
| WO | WO 95/02043 | 1/1995 |
| WO | WO 95/24471 | 9/1995 |
| WO | WO 95/26398 | 10/1995 |

OTHER PUBLICATIONS

Hernrissat, Cellulose, vol. 1, pp. 169–196 (1994).
Béguin, Annu. Rev. Microbiol., vol. 44, pp. 219–248 (1990).
Henrissat, Biochem. J., vol. 280, pp. 309–316 (1991).
Saloheimo et al., Gene, vol. 63, pp. 11–21 (1988).
Penttiläet al., Gene vol. 45, pp. 253–263 (1986).
Ali et al., FEMS Microbiology Letters, vol. 25, pp. 15–22 (1995).
Xue et al., Journal of General Microbiology, vol. 138, pp. 2397–2403 (1992).
Bëguin et al., FEMS Microbiology Reviews, vol. 13, pp. 25–58 (1994).
Sheppard et al., Gene, vol. 150, pp. 163–167 (1994).
Wang et al., Gene, vol. 58, pp. 125–128 (1995).
Xue et al., Journal of General Microbiology, vol. 138, pp. 1413–1420 (1992).

(List continued on next page.)

Primary Examiner—Elizabeth Slobodyansky
(74) Attorney, Agent, or Firm—Elias J. Lambiris

(57) ABSTRACT

The present invention relates to enzyme preparations consisting essentially of an enzyme which has cellulytic activity and comprises a first amino acid sequence consisting of 14 amino acid residues having the following sequence

Figure 2A:
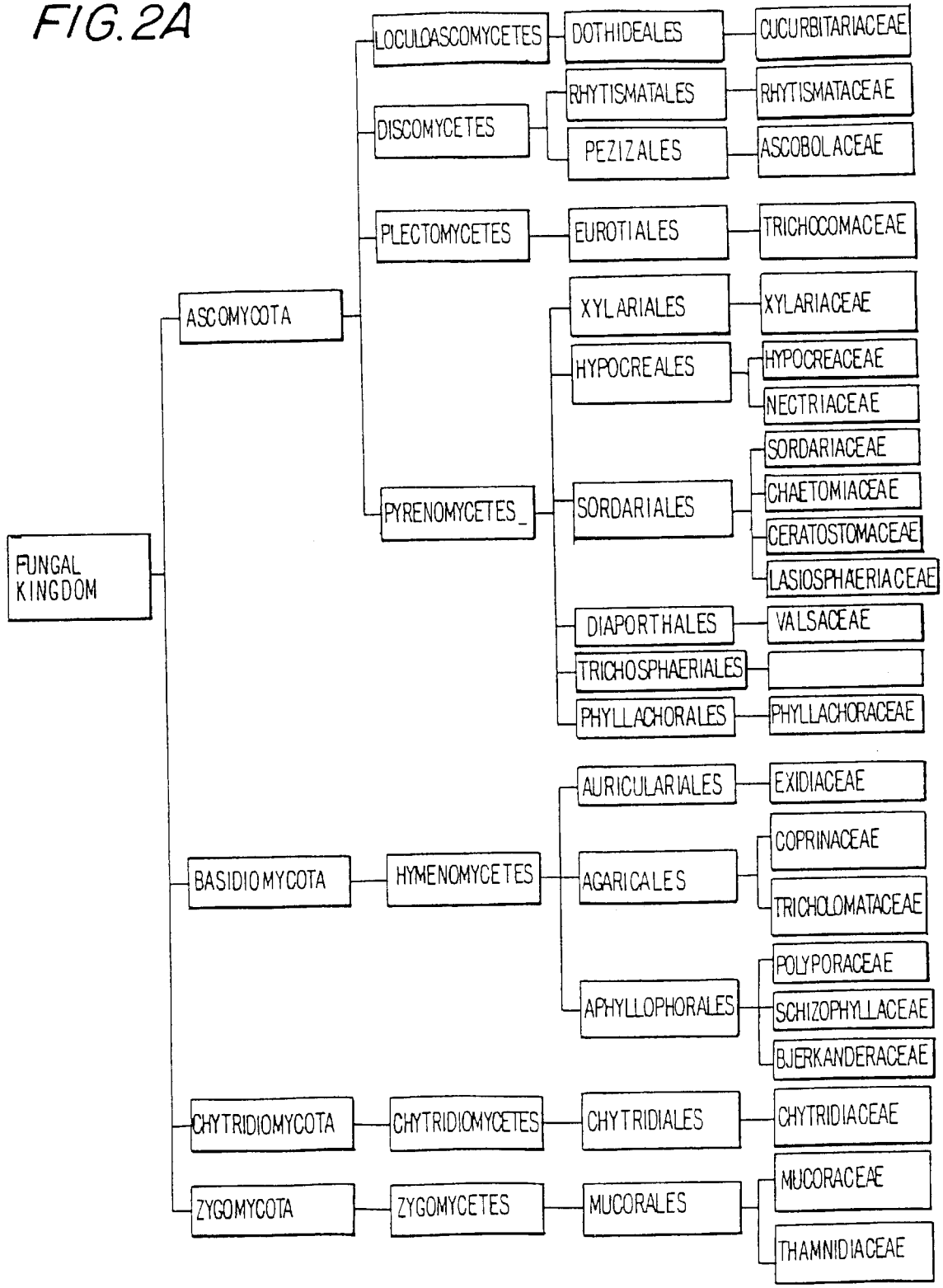

```
Thr Arg Xaa Xaa Asp Cys Cys Xaa Xaa Xaa Cys Xaa
 1   2   3   4   5   6   7   8   9  10  11  12
Trp Xaa
 13  14
``` and a second amino acid sequence consisting of 5 amino acid residues having the following sequence

```
Trp Cys Cys Xaa Cys
 1   2   3   4   5
``` wherein, in position 3 of the first sequence, the amino acid is Trp, Tyr or Phe; in position 4 of the first sequence, the amino acid is Trp, Tyr or Phe; in position 8 of the first sequence, the amino acid is Arg, Lys or His; in position 9, 10, 12 and 14, respectively, of the first sequence, and in position 4 of the second sequence, the amino acid is any of the 20 naturally occurring amino acid residues with the provisos that, in the first amino acid sequence, (i) when the amino residue in position 12 is Ser, then the amino acid residue in position 14 is not Ser, and (ii) when the amino residue in position 12 is Gly, then the amino acid residue in position 14 is not Ala, performs very good in industrial applications such as laundry compositions, for biopolishing of newly manufactured textiles, for providing an abraded look of cellulosic fabric or garment, and for treatment of paper pulp. Further, the invention relates to DNA constructs encoding such enzymes, a method for providing a gene encoding for such enzymes, a method of producing the enzymes, enzyme preparations containing such enzymes, and the use of these enzymes for a number of industrial applications.

11 Claims, 8 Drawing Sheets

OTHER PUBLICATIONS

Wang et al., Applied and Environmental Microbiology, vol. 61, No. 5, pp. 2004–2006 (1995).

Xu et al., Journal of General Microbiology, vol. 138, pp. 2397–2403 (1992).

DalbØge et al., Mol Gen Genet, vol. 243, pp. 253–260 (1994).

Saloheimo et al., Molecular Microbiology, vol. 32, No. 2, pp. 219–228 (1994).

Ooi et al., Nucleic Acids Research, vol. 18, No. 19, pp. 5884 (1990).

Van Arsdell et al., Bio/Technology, vol. 5, pp. 60–64 (1987).

Enari, Chapter 4, Microbial Cellulases, pp. 183–223.

Gonzalez et al., Appl. Microbiol. Biotechnol, vol. 38, pp. 370–375.

Yamane et al., Methods in Enzymology, vol. 160, pp. 200–391 (1988).

Ooi et al., Curr Genet, vol. 18, pp. 217–222 (1990).

FIG. 1A (sequence alignment figure)

FIG. 1B

| | | | | | |
|---|---|---|---|---|---|
| Acremonium I | 242 | - - - - - - - - - - - - - - - - - - - - - - - - - - - | - - - - - - - - - - - - - - - - - | - - - - - - - - - - - - - - - - - - - - - - | 241 |
| V. colletotrichoides | 243 | T T I T A S S S S S S S S S S - - - | - - - - - - - - - - - - - - - - - | - - - - - - - - - - - - - - - - - - - - - - | 257 |
| C. scabella | 0 | - - - - - - - - - - - - - - - - - - - - - - - - - - - | - - - - - - - - - - - - - - - - - | - - - - - - - - - - - - - - - - - - - - - - | 226 |
| Acremonium II | 246 | P T T T T T S S K P K T T S A P S T L S N P S A P Q Q P G N T D | | | 277 |
| T. terrestris | 245 | P T S T A P G S G Q - - - - - - - - - - - - - - - - - | | | 254 |
| M. thermophila | 0 | | | | 225 |
| M. phaseolina | 0 | | | | 222 |

| | | | | | |
|---|---|---|---|---|---|
| Acremonium I | 242 | - - - - - - - - - - - - - - - - - T T T S S P P Q P T N G G G G T S P | | | 260 |
| V. colletotrichoides | 258 | - - - - - - - - - - - - - - - - - - T T A G S P P V P T G G G S G P T S P | | | 276 |
| C. scabella | 0 | | | | 226 |
| Acremonium II | 278 | R P A E T T T T K L P A L P A T T S S P A V S V P S S A R V P | | | 309 |
| T. terrestris | 255 | - - - - - - - - - - - - - - - - - - - T S - - - - - P G G G S G C T S Q | | | 266 |
| M. thermophila | 0 | | | | 225 |
| M. phaseolina | 0 | | | | 222 |

| | | | | | |
|---|---|---|---|---|---|
| Acremonium I | 261 | H W G Q C G G Q G - W S G P T A C A G G S T C N L I N P W Y S Q | | | 291 |
| V. colletotrichoides | 277 | V W G Q C G G Q G - W S G P T R C V A G S T C S V V N P W Y S Q | | | 307 |
| C. scabella | 0 | | | | 226 |
| Acremonium II | 310 | L W G Q C D S E A S W D A P K K C A K G T K C V Y Y N D W Y S Q | | | 341 |
| T. terrestris | 267 | K W A Q C G G I G - F S G C T T C V S G T T C Q K L N D Y Y S Q | | | 297 |
| M. thermophila | 0 | | | | 225 |
| M. phaseolina | 0 | | | | 222 |

| | | | | | |
|---|---|---|---|---|---|
| Acremonium I | 292 | C I P N - - - - - - - - - - - - - - - - - - - - - - - | | | 295 |
| V. colletotrichoides | 308 | C F P - - - - - - - - - - - - - - - - - - - - - - - - | | | 310 |
| C. scabella | 0 | | | | 226 |
| Acremonium II | 342 | C Q P K N S C A - - - - - - - - - - - - - - - - - - - | | | 349 |
| T. terrestris | 298 | C L - - - - - - - - - - - - - - - - - - - - - - - - - | | | 299 |
| M. thermophila | 0 | | | | 225 |
| M. phaseolina | 0 | | | | 222 |

Fig. 1C

FIG. 3A

| | | | | | | |
|---|---|---|---|---|---|---|
| H. nigrescens | 29 | A N Q T P W A V S D D F A Y G F A A T A L A G - - - - - - - - - - - - - - - - - - - - - - | | | | 51 |
| T. verrucosus | 27 | A K Q T P W A - - - - - - - - - - - - - - - - - - - - - - - - - - - - - - - - - - - - - - | | | | 33 |
| H. grisea | 32 | A D Q T P W A L N D D F A Y G F A A T A I S G G S E A S - - - - - - - - - - - - - - - - - | | | | 59 |
| C. longenarium | 27 | S - - - - - - - - - - - - - - - - - - - - - - - - - - - - - - - - - - - - - - - - - - - - | | | | 27 |
| P. punctata | 15 | S N Q S P W A V N D D L A Y G W A A V S I A G - - - - - - - - - - - - - - - - - - - - - - | | | | 37 |
| X. hypoxylon | 25 | S N Q S P W A V D D S L S Y G W A A V R I Y G H T E T T W C C A C Y E - - - - - - - - - - | | | | 59 |
| Coniothecium sp. | 32 | S T Q Q P W A V N D N L A Y G F A A T A V N I A G - - - - - - - - - - - - - - - - - - - - | | | | 57 |
| P. verrucylosum | 16 | S N Q P W V V N D N L A Y G F A A V R I A G Q S E - - - - - - - - - - - - - - - - - - - - | | | | 38 |
| F. anguioides | 34 | S S H S P W A V S D S L S Y G W A A V R I A G Q S E - - - - - - - - - - - - - - - - - - - | | | | 59 |
| S. dilutellus | 14 | A S Q E P W A V S S N V A Y G F A A V R I S G - - - - - - - - - - - - - - - - - - - - - - | | | | 36 |
| F. oxy. ssp. lycop. | 25 | T N Y S P W A V N D E L A Y G F A A T K I S G G S E A S W C C A C Y L - - - - - - - - - - | | | | 59 |
| T. thermophila | 24 | S N Y S P W A V N D D L A Y G F A V T K L S G G S E A - - - - - - - - - - - - - - - - - - | | | | 50 |
| P. nitens | 28 | T N Y S P W A V N D N L A Y G F A A T K L A G G S E - - - - - - - - - - - - - - - - - - - | | | | 53 |
| C. virescens | 27 | S N T S P E A V N N L A Y G F A A T K L A G G S E A - - - - - - - - - - - - - - - - - - - | | | | 53 |
| Nigrospora sp. | 25 | S N T S P W A V S D Q L A Y G Y V A T S I S G G T E S - - - - - - - - - - - - - - - - - - | | | | 51 |
| CBS 271.96 | 27 | S N T S P W A V S D Q L A Y G Y L A T S L S G G T E S - - - - - - - - - - - - - - - - - - | | | | 53 |
| C. foecundissimum | 33 | A N N S P W A V N D - - A Y G F A A T K L S G G T E S S - - - - - - - - - - - - - - - - - | | | | 60 |
| N. pinea | 12 | A N N S P W A V N D - - - - - - - - - - - - - - - - - - - - - - - - - - - - - - - - - - - | | | | 21 |
| C. cuniculorum | 33 | S N N S P W A V D D Q T A Y G F A A T A I S G Q S E S S - - - - - - - - - - - - - - - - - | | | | 60 |
| C. fresenii | 29 | S N N S P W A V D D Q T A Y G F A A T A I S G Q S - - - - - - - - - - - - - - - - - - - - | | | | 53 |
| S. boninensis | 11 | S N N S P W A V N E D - - - - - - - - - - - - - - - - - - - - - - - - - - - - - - - - - - | | | | 21 |
| T. roseum | 30 | A N Y Q P W A V N D Q L A Y G F A A T A I N G G T E - - - - - - - - - - - - - - - - - - - | | | | 55 |
| D. gossypina | 27 | T Y S T P W A V D D N L S Y G F A A A K L S G - - - - - - - - - - - - - - - - - - - - - - | | | | 49 |
| E. glanduloso | 27 | N N Q P W A V N D L V S Y G F A A T A I N G G N - - - - - - - - - - - - - - - - - - - - - | | | | 51 |
| U. bilgramii | 20 | S N Q P W A V N D T F S Y G F A G I F I T G H V E - - - - - - - - - - - - - - - - - - - - | | | | 45 |
| CBS 270.96 | 0 | - - - - - - - - - - - - - - - - - - - - - - - - - - - - - - - - - - - - - - - - - - - - - | | | | 28 |

FIG. 3B

SEQUENCE LISTING (1) GENERAL INFORMATION:

(iii) NUMBER OF SEQUENCES: 109

(2) INFORMATION FOR SEQ ID NO: 1:

(i) SEQUENCE CHARACTERISTICS:
      (A) LENGTH: 960 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 113..787

(xi) SEQUENCE DESCRIPTION: SEQ ID NO: 1:

```
AAAGAAAGGC TCTCTGCTGT CGTCGCTCTC GTCGCTCTCG TCGGCATCCT CCATCCGTCC        60

GCCTTTGATA ACCCGCTCCC CGACTCAGTC AAGACGACGC ATACTTGGCA CC ATG          115
                                                        Met
                                                        1

CAT CTC TCC GCC ACC ACC GGG TTC CTC GCC CTC CCG GTC CTG GCC CTG        163
His Leu Ser Ala Thr Thr Gly Phe Leu Ala Leu Pro Val Leu Ala Leu
          5                  10                  15

GAC CAG CTC TCG GGC ATC GGC CAG ACG ACC CGG TAC TGG GAC TGC TGC        211
Asp Gln Leu Ser Gly Ile Gly Gln Thr Thr Arg Tyr Trp Asp Cys Cys
            20                  25                  30

AAG CCG AGC TGC GCC TGG CCC GGC AAG GGC CCC TCG TCT CCG GTG CAG        259
Lys Pro Ser Cys Ala Trp Pro Gly Lys Gly Pro Ser Ser Pro Val Gln
        35                  40                  45

GCC TGC GAC AAG AAC GAC AAC CCG CTC AAC GAC GGC GGC TCC ACC CGG        307
Ala Cys Asp Lys Asn Asp Asn Pro Leu Asn Asp Gly Gly Ser Thr Arg
 50                  55                  60                  65

TCC GGC TGC GAC GCG GGC GGC AGC GCC TAC ATG TGC TCC TCC CAG AGC        355
Ser Gly Cys Asp Ala Gly Gly Ser Ala Tyr Met Cys Ser Ser Gln Ser
                70                  75                  80

CCC TGG GCC GTC AGC GAC GAG CTG TCG TAC GGC TGG GCG GCC GTC AAG        403
Pro Trp Ala Val Ser Asp Glu Leu Ser Tyr Gly Trp Ala Ala Val Lys
             85                  90                  95

CTC GCC GGC AGC TCC GAG TCG CAG TGG TGC TGC GCC TGC TAC GAG CTG        451
Leu Ala Gly Ser Ser Glu Ser Gln Trp Cys Cys Ala Cys Tyr Glu Leu
            100                 105                 110
```

```
ACC TTC ACC AGC GGG CCG GTC GCG GGC AAG AAG ATG ATT GTG CAG GCG        499
Thr Phe Thr Ser Gly Pro Val Ala Gly Lys Lys Met Ile Val Gln Ala
    115                 120                 125

ACC AAC ACC GGT GGC GAC CTG GGC GAC AAC CAC TTT GAC CTG GCC ATC        547
Thr Asn Thr Gly Gly Asp Leu Gly Asp Asn His Phe Asp Leu Ala Ile
130                 135                 140                 145

CCC GGT GGC GGT GTC GGT ATT TTC AAC GCC TGC ACC GAC CAG TAC GGC        595
Pro Gly Gly Gly Val Gly Ile Phe Asn Ala Cys Thr Asp Gln Tyr Gly
                150                 155                 160

GCT CCC CCG AAC GGC TGG GGC GAC CGC TAC GGC GGC ATC CAT TCC AAG        643
Ala Pro Pro Asn Gly Trp Gly Asp Arg Tyr Gly Gly Ile His Ser Lys
            165                 170                 175

GAA GAG TGC GAA TCC TTC CCG GAG GCC CTC AAG CCC GGC TGC AAC TGG        691
Glu Glu Cys Glu Ser Phe Pro Glu Ala Leu Lys Pro Gly Cys Asn Trp
        180                 185                 190

CGC TTC GAC TGG TTC CAA AAC GCC GAC AAC CCG TCG GTC ACC TTC CAG        739
Arg Phe Asp Trp Phe Gln Asn Ala Asp Asn Pro Ser Val Thr Phe Gln
    195                 200                 205

GAG GTG GCC TGC CCG TCG GAG CTC ACG TCC AAG AGC GGC TGC TCC CGT        787
Glu Val Ala Cys Pro Ser Glu Leu Thr Ser Lys Ser Gly Cys Ser Arg
210                 215                 220                 225

TAAGAGGGAA GAGAGGGGGC TGGAAGGACC GAAAGATTCA ACCTCTGCTC CTGCTGGGG       847

AGCTCGGGCG CGAGTGTGAA ACTGGTGTAA ATATTGTGGC ACACACAAGC TACTACAGT       907

CGTCTCGCCG TCCGGCTAAC TAGCCTTGCT GCGGATCTGT CCAAAAAAAA AAA             960

(2) INFORMATION FOR SEQ ID NO: 2:

(i) SEQUENCE CHARACTERISTICS:
        (A) LENGTH: 225 amino acids
        (B) TYPE: amino acid
        (D) TOPOLOGY: linear (ii) MOLECULE TYPE: protein (xi) SEQUENCE DESCRIPTION: SEQ ID NO: 2:

Met His Leu Ser Ala Thr Thr Gly Phe Leu Ala Leu Pro Val Leu Ala
 1               5                  10                  15

Leu Asp Gln Leu Ser Gly Ile Gly Gln Thr Thr Arg Tyr Trp Asp Cys
                20                  25                  30

Cys Lys Pro Ser Cys Ala Trp Pro Gly Lys Gly Pro Ser Ser Pro Val
            35                  40                  45

Gln Ala Cys Asp Lys Asn Asp Asn Pro Leu Asn Asp Gly Gly Ser Thr
        50                  55                  60

Arg Ser Gly Cys Asp Ala Gly Ser Ala Tyr Met Cys Ser Ser Gln
65                  70                  75                  80

Ser Pro Trp Ala Val Ser Asp Glu Leu Ser Tyr Gly Trp Ala Ala Val
                85                  90                  95

Lys Leu Ala Gly Ser Ser Glu Ser Gln Trp Cys Cys Ala Cys Tyr Glu
            100                 105                 110

Leu Thr Phe Thr Ser Gly Pro Val Ala Gly Lys Lys Met Ile Val Gln
        115                 120                 125

Ala Thr Asn Thr Gly Gly Asp Leu Gly Asp Asn His Phe Asp Leu Ala
    130                 135                 140

Ile Pro Gly Gly Gly Val Gly Ile Phe Asn Ala Cys Thr Asp Gln Tyr
145                 150                 155                 160

Gly Ala Pro Pro Asn Gly Trp Gly Asp Arg Tyr Gly Gly Ile His Ser
                165                 170                 175
```

```
Lys Glu Glu Cys Glu Ser Phe Pro Glu Ala Leu Lys Pro Gly Cys Asn
            180                 185                 190

Trp Arg Phe Asp Trp Phe Gln Asn Ala Asp Asn Pro Ser Val Thr Phe
        195                 200                 205

Gln Glu Val Ala Cys Pro Ser Glu Leu Thr Ser Lys Ser Gly Cys Ser
    210                 215                 220

Arg
225

(2) INFORMATION FOR SEQ ID NO: 3:

(i) SEQUENCE CHARACTERISTICS:
        (A) LENGTH: 894 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..891

(xi) SEQUENCE DESCRIPTION: SEQ ID NO: 3:

ATG CAT CTC TCC GCC ACC ACC GGG TTC CTC GCC CTC CCG GTC CTG GCC      48
Met His Leu Ser Ala Thr Thr Gly Phe Leu Ala Leu Pro Val Leu Ala
                230                 235                 240

CTG GAC CAG CTC TCG GGC ATC GGC CAG ACG ACC CGG TAC TGG GAC TGC      96
Leu Asp Gln Leu Ser Gly Ile Gly Gln Thr Thr Arg Tyr Trp Asp Cys
            245                 250                 255

TGC AAG CCG AGC TGC GCC TGG CCC GGC AAG GGC CCC TCG TCT CCG GTG     144
Cys Lys Pro Ser Cys Ala Trp Pro Gly Lys Gly Pro Ser Ser Pro Val
        260                 265                 270

CAG GCC TGC GAC AAG AAC GAC AAC CCG CTC AAC GAC GGC GGC TCC ACC     192
Gln Ala Cys Asp Lys Asn Asp Asn Pro Leu Asn Asp Gly Gly Ser Thr
    275                 280                 285

CGG TCC GGC TGC GAC GCG GGC GGC AGC GCC TAC ATG TGC TCC TCC CAG     240
Arg Ser Gly Cys Asp Ala Gly Gly Ser Ala Tyr Met Cys Ser Ser Gln
290                 295                 300                 305

AGC CCC TGG GCC GTC AGC GAC GAG CTG TCG TAC GGC TGG GCG GCC GTC     288
Ser Pro Trp Ala Val Ser Asp Glu Leu Ser Tyr Gly Trp Ala Ala Val
                310                 315                 320

AAG CTC GCC GGC AGC TCC GAG TCG CAG TGG TGC TGC GCC TGC TAC GAG     336
Lys Leu Ala Gly Ser Ser Glu Ser Gln Trp Cys Cys Ala Cys Tyr Glu
            325                 330                 335

CTG ACC TTC ACC AGC GGG CCG GTC GCG GGC AAG AAG ATG ATT GTG CAG     384
Leu Thr Phe Thr Ser Gly Pro Val Ala Gly Lys Lys Met Ile Val Gln
        340                 345                 350

GCG ACC AAC ACC GGT GGC GAC CTG GGC GAC AAC CAC TTT GAC CTG GCC     432
Ala Thr Asn Thr Gly Gly Asp Leu Gly Asp Asn His Phe Asp Leu Ala
    355                 360                 365

ATC CCC GGT GGC GGT GTC GGT ATT TTC AAC GCC TGC ACC GAC CAG TAC     480
Ile Pro Gly Gly Gly Val Gly Ile Phe Asn Ala Cys Thr Asp Gln Tyr
370                 375                 380                 385

GGC GCT CCC CCG AAC GGC TGG GGC GAC CGC TAC GGC GGC ATC CAT TCC     528
Gly Ala Pro Pro Asn Gly Trp Gly Asp Arg Tyr Gly Gly Ile His Ser
                390                 395                 400

AAG GAA GAG TGC GAA TCC TTC CCG GAG GCC CTC AAG CCC GGC TGC AAC     576
Lys Glu Glu Cys Glu Ser Phe Pro Glu Ala Leu Lys Pro Gly Cys Asn
            405                 410                 415

TGG CGC TTC GAC TGG TTC CAA AAC GCC GAC AAC CCG TCG GTC ACC TTC     624
Trp Arg Phe Asp Trp Phe Gln Asn Ala Asp Asn Pro Ser Val Thr Phe
```

```
              420                 425                 430
CAG GAG GTG GCC TGC CCG TCG GAG CTC ACG TCC AAG AGC GGC TGC TCC    672
Gln Glu Val Ala Cys Pro Ser Glu Leu Thr Ser Lys Ser Gly Cys Ser
        435                 440                 445

CGT CCC TCC AGC AGC ACC AGC TCT CCG GTC AAC CAG CCT ACC AGC ACC    720
Arg Pro Ser Ser Ser Thr Ser Ser Pro Val Asn Gln Pro Thr Ser Thr
450                 455                 460                 465

AGC ACC ACG TCC ACC TCC ACC ACC TCG AGC CCG CCA GTC CAG CCT ACG    768
Ser Thr Thr Ser Thr Ser Thr Thr Ser Ser Pro Pro Val Gln Pro Thr
                470                 475                 480

ACT CCC AGC GGC TGC ACT GCT GAG AGG TGG GCT CAG TGC GGC GGC AAT    816
Thr Pro Ser Gly Cys Thr Ala Glu Arg Trp Ala Gln Cys Gly Gly Asn
            485                 490                 495

GGC TGG AGC GGC TGC ACC ACC TGC GTC GCT GGC AGC ACT TGC ACG AAG    864
Gly Trp Ser Gly Cys Thr Thr Cys Val Ala Gly Ser Thr Cys Thr Lys
        500                 505                 510

ATT AAT GAC TGG TAC CAT CAG TGC CTG TAG                            894
Ile Asn Asp Trp Tyr His Gln Cys Leu
    515                 520

(2) INFORMATION FOR SEQ ID NO: 4:

(i) SEQUENCE CHARACTERISTICS:
        (A) LENGTH: 297 amino acids
        (B) TYPE: amino acid
        (D) TOPOLOGY: linear (ii) MOLECULE TYPE: protein (xi) SEQUENCE DESCRIPTION: SEQ ID NO: 4:

Met His Leu Ser Ala Thr Thr Gly Phe Leu Ala Leu Pro Val Leu Ala
  1               5                  10                  15

Leu Asp Gln Leu Ser Gly Ile Gly Gln Thr Thr Arg Tyr Trp Asp Cys
             20                  25                  30

Cys Lys Pro Ser Cys Ala Trp Pro Gly Lys Gly Pro Ser Ser Pro Val
         35                  40                  45

Gln Ala Cys Asp Lys Asn Asp Asn Pro Leu Asn Asp Gly Gly Ser Thr
     50                  55                  60

Arg Ser Gly Cys Asp Ala Gly Gly Ser Ala Tyr Met Cys Ser Ser Gln
 65                  70                  75                  80

Ser Pro Trp Ala Val Ser Asp Glu Leu Ser Tyr Gly Trp Ala Ala Val
                 85                  90                  95

Lys Leu Ala Gly Ser Ser Glu Ser Gln Trp Cys Cys Ala Cys Tyr Glu
            100                 105                 110

Leu Thr Phe Thr Ser Gly Pro Val Ala Gly Lys Lys Met Ile Val Gln
        115                 120                 125

Ala Thr Asn Thr Gly Gly Asp Leu Gly Asp Asn His Phe Asp Leu Ala
    130                 135                 140

Ile Pro Gly Gly Gly Val Gly Ile Phe Asn Ala Cys Thr Asp Gln Tyr
145                 150                 155                 160

Gly Ala Pro Pro Asn Gly Trp Gly Asp Arg Tyr Gly Gly Ile His Ser
                165                 170                 175

Lys Glu Glu Cys Glu Ser Phe Pro Glu Ala Leu Lys Pro Gly Cys Asn
            180                 185                 190

Trp Arg Phe Asp Trp Phe Gln Asn Ala Asp Asn Pro Ser Val Thr Phe
        195                 200                 205

Gln Glu Val Ala Cys Pro Ser Glu Leu Thr Ser Lys Ser Gly Cys Ser
    210                 215                 220
```

| | | | | | | | | | | | | |
|---|---|---|---|---|---|---|---|---|---|---|---|---|
|Arg|Pro|Ser|Ser|Thr|Ser|Ser|Pro|Val|Asn|Gln|Pro|Thr|Ser|Thr|
|225| | | |230| | | |235| | | |240|

Ser Thr Thr Ser Thr Ser Thr Thr Ser Ser Pro Pro Val Gln Pro Thr
                    245                 250                 255

Thr Pro Ser Gly Cys Thr Ala Glu Arg Trp Ala Gln Cys Gly Gly Asn
            260                 265                 270

Gly Trp Ser Gly Cys Thr Thr Cys Val Ala Gly Ser Thr Cys Thr Lys
        275                 280                 285

Ile Asn Asp Trp Tyr His Gln Cys Leu
    290                 295

(2) INFORMATION FOR SEQ ID NO: 5:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..924

(xi) SEQUENCE DESCRIPTION: SEQ ID NO: 5:

```
ATG CAT CTC TCC GCC ACC ACC GGG TTC CTC GCC CTC CCG GTC CTG GCC      48
Met His Leu Ser Ala Thr Thr Gly Phe Leu Ala Leu Pro Val Leu Ala
            300                 305                 310

CTG GAC CAG CTC TCG GGC ATC GGC CAG ACG ACC CGG TAC TGG GAC TGC      96
Leu Asp Gln Leu Ser Gly Ile Gly Gln Thr Thr Arg Tyr Trp Asp Cys
    315                 320                 325

TGC AAG CCG AGC TGC GCC TGG CCC GGC AAG GGC CCC TCG TCT CCG GTG     144
Cys Lys Pro Ser Cys Ala Trp Pro Gly Lys Gly Pro Ser Ser Pro Val
330                 335                 340                 345

CAG GCC TGC GAC AAG AAC GAC AAC CCG CTC AAC GAC GGC GGC TCC ACC     192
Gln Ala Cys Asp Lys Asn Asp Asn Pro Leu Asn Asp Gly Gly Ser Thr
                350                 355                 360

CGG TCC GGC TGC GAC GCG GGC GGC AGC GCC TAC ATG TGC TCC TCC CAG     240
Arg Ser Gly Cys Asp Ala Gly Gly Ser Ala Tyr Met Cys Ser Ser Gln
            365                 370                 375

AGC CCC TGG GCC GTC AGC GAC GAG CTG TCG TAC GGC TGG GCG GCC GTC     288
Ser Pro Trp Ala Val Ser Asp Glu Leu Ser Tyr Gly Trp Ala Ala Val
    380                 385                 390

AAG CTC GCC GGC AGC TCC GAG TCG CAG TGG TGC TGC GCC TGC TAC GAG     336
Lys Leu Ala Gly Ser Ser Glu Ser Gln Trp Cys Cys Ala Cys Tyr Glu
395                 400                 405

CTG ACC TTC ACC AGC GGG CCG GTC GCG GGC AAG AAG ATG ATT GTG CAG     384
Leu Thr Phe Thr Ser Gly Pro Val Ala Gly Lys Lys Met Ile Val Gln
410                 415                 420                 425

GCG ACC AAC ACC GGT GGC GAC CTG GGC GAC AAC CAC TTT GAC CTG GCC     432
Ala Thr Asn Thr Gly Gly Asp Leu Gly Asp Asn His Phe Asp Leu Ala
                430                 435                 440

ATC CCC GGT GGC GGT GTC GGT ATT TTC AAC GCC TGC ACC GAC CAG TAC     480
Ile Pro Gly Gly Gly Val Gly Ile Phe Asn Ala Cys Thr Asp Gln Tyr
            445                 450                 455

GGC GCT CCC CCG AAC GGC TGG GGC GAC CGC TAC GGC GGC ATC CAT TCC     528
Gly Ala Pro Pro Asn Gly Trp Gly Asp Arg Tyr Gly Gly Ile His Ser
    460                 465                 470

AAG GAA GAG TGC GAA TCC TTC CCG GAG GCC CTC AAG CCC GGC TGC AAC     576
Lys Glu Glu Cys Glu Ser Phe Pro Glu Ala Leu Lys Pro Gly Cys Asn
```

```
TGG CGC TTC GAC TGG TTC CAA AAC GCC GAC AAC CCG TCG GTC ACC TTC      624
Trp Arg Phe Asp Trp Phe Gln Asn Ala Asp Asn Pro Ser Val Thr Phe
490             495                 500                 505

CAG GAG GTG GCC TGC CCG TCG GAG CTC ACG TCC AAG AGC GGC TGC TCC      672
Gln Glu Val Ala Cys Pro Ser Glu Leu Thr Ser Lys Ser Gly Cys Ser
                510                 515                 520

CGT AAC GAC GAC GGC AAC TTC CCT GCC GTC CAG ATC CCC TCC AGC AGC      720
Arg Asn Asp Asp Gly Asn Phe Pro Ala Val Gln Ile Pro Ser Ser Ser
            525                 530                 535

ACC AGC TCT CCG GTC AAC CAG CCT ACC AGC ACC AGC ACC ACG TCC ACC      768
Thr Ser Ser Pro Val Asn Gln Pro Thr Ser Thr Ser Thr Thr Ser Thr
        540                 545                 550

TCC ACC ACC TCG AGC CCG CCA GTC CAG CCT ACG ACT CCC AGC GGC TGC      816
Ser Thr Thr Ser Ser Pro Pro Val Gln Pro Thr Thr Pro Ser Gly Cys
    555                 560                 565

ACT GCT GAG AGG TGG GCT CAG TGC GGC GGC AAT GGC TGG AGC GGC TGC      864
Thr Ala Glu Arg Trp Ala Gln Cys Gly Gly Asn Gly Trp Ser Gly Cys
570             575                 580                 585

ACC ACC TGC GTC GCT GGC AGC ACT TGC ACG AAG ATT AAT GAC TGG TAC      912
Thr Thr Cys Val Ala Gly Ser Thr Cys Thr Lys Ile Asn Asp Trp Tyr
                590                 595                 600

CAT CAG TGC CTG TAG                                                  927
His Gln Cys Leu
            605

(2) INFORMATION FOR SEQ ID NO: 6:

(i) SEQUENCE CHARACTERISTICS:
        (A) LENGTH: 308 amino acids
        (B) TYPE: amino acid
        (D) TOPOLOGY: linear (ii) MOLECULE TYPE: protein (xi) SEQUENCE DESCRIPTION: SEQ ID NO: 6:

Met His Leu Ser Ala Thr Thr Gly Phe Leu Ala Leu Pro Val Leu Ala
 1               5                  10                  15

Leu Asp Gln Leu Ser Gly Ile Gly Gln Thr Thr Arg Tyr Trp Asp Cys
                20                  25                  30

Cys Lys Pro Ser Cys Ala Trp Pro Gly Lys Gly Pro Ser Ser Pro Val
            35                  40                  45

Gln Ala Cys Asp Lys Asn Asp Asn Pro Leu Asn Asp Gly Gly Ser Thr
        50                  55                  60

Arg Ser Gly Cys Asp Ala Gly Gly Ser Ala Tyr Met Cys Ser Ser Gln
65                  70                  75                  80

Ser Pro Trp Ala Val Ser Asp Glu Leu Ser Tyr Gly Trp Ala Ala Val
                85                  90                  95

Lys Leu Ala Gly Ser Ser Glu Ser Gln Trp Cys Cys Ala Cys Tyr Glu
            100                 105                 110

Leu Thr Phe Thr Ser Gly Pro Val Ala Gly Lys Lys Met Ile Val Gln
        115                 120                 125

Ala Thr Asn Thr Gly Gly Asp Leu Gly Asp Asn His Phe Asp Leu Ala
    130                 135                 140

Ile Pro Gly Gly Gly Val Gly Ile Phe Asn Ala Cys Thr Asp Gln Tyr
145                 150                 155                 160

Gly Ala Pro Pro Asn Gly Trp Gly Asp Arg Tyr Gly Gly Ile His Ser
                165                 170                 175
```

```
Lys Glu Glu Cys Glu Ser Phe Pro Glu Ala Leu Lys Pro Gly Cys Asn
            180                 185                 190

Trp Arg Phe Asp Trp Phe Gln Asn Ala Asp Asn Pro Ser Val Thr Phe
        195                 200                 205

Gln Glu Val Ala Cys Pro Ser Glu Leu Thr Ser Lys Ser Gly Cys Ser
    210                 215                 220

Arg Asn Asp Asp Gly Asn Phe Pro Ala Val Gln Ile Pro Ser Ser Ser
225                 230                 235                 240

Thr Ser Ser Pro Val Asn Gln Pro Thr Ser Ser Thr Thr Ser Thr
                245                 250                 255

Ser Thr Thr Ser Ser Pro Pro Val Gln Pro Thr Thr Pro Ser Gly Cys
            260                 265                 270

Thr Ala Glu Arg Trp Ala Gln Cys Gly Gly Asn Gly Trp Ser Gly Cys
        275                 280                 285

Thr Thr Cys Val Ala Gly Ser Thr Cys Thr Lys Ile Asn Asp Trp Tyr
        290                 295                 300

His Gln Cys Leu
305
```

(2) INFORMATION FOR SEQ ID NO: 7:

(i) SEQUENCE CHARACTERISTICS:
        (A) LENGTH: 1154 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 51..935

(xi) SEQUENCE DESCRIPTION: SEQ ID NO: 7:

```
CCAGTGTGCT GGAAAGCCTT CGTGCTGTCC CCGACGTATC CCTGACCGCC ATG CGT        56
                                                      Met Arg
                                                          310

TCC ACC AGC ATC TTG ATC GGC CTT GTT GCC GGC GTC GCT GCT CAG AGC      104
Ser Thr Ser Ile Leu Ile Gly Leu Val Ala Gly Val Ala Ala Gln Ser
                315                 320                 325

TCT GGC TCT GGC CAT ACA ACC AGG TAC TGG GAC TGC TGC AAG CCC TCA      152
Ser Gly Ser Gly His Thr Thr Arg Tyr Trp Asp Cys Cys Lys Pro Ser
            330                 335                 340

TGC GCC TGG GAT GAG AAG GCG GCT GTC AGC CGG CCG GTC ACA ACA TGC      200
Cys Ala Trp Asp Glu Lys Ala Ala Val Ser Arg Pro Val Thr Thr Cys
        345                 350                 355

GAC AGG AAC AAC AGC CCC CTT TCG CCC GGC GCT GTG AGC GGC TGC GAC      248
Asp Arg Asn Asn Ser Pro Leu Ser Pro Gly Ala Val Ser Gly Cys Asp
    360                 365                 370

CCC AAC GGC GTT GCA TTC ACC TGC AAC GAC AAC CAG CCT TGG GCC GTA      296
Pro Asn Gly Val Ala Phe Thr Cys Asn Asp Asn Gln Pro Trp Ala Val
375                 380                 385                 390

AAC AAC AAT GTC GCC TAC GGT TTT GCG GCT ACC GCC TTC CCT GGT GGC      344
Asn Asn Asn Val Ala Tyr Gly Phe Ala Ala Thr Ala Phe Pro Gly Gly
                395                 400                 405

AAT GAG GCG TCG TGG TGC TGT GCC TGC TAT GCT CTT CAA TTC ACA TCC      392
Asn Glu Ala Ser Trp Cys Cys Ala Cys Tyr Ala Leu Gln Phe Thr Ser
            410                 415                 420

GGC CCC GTT GCT GGC AAG ACG ATG GTT GTG CAA TCC ACC AAC ACT GGC      440
Gly Pro Val Ala Gly Lys Thr Met Val Val Gln Ser Thr Asn Thr Gly
        425                 430                 435
```

```
GGA GAT CTC AGC GGC ACT CAC TTC GAT ATC CAG ATG CCC GGT GGA GGT        488
Gly Asp Leu Ser Gly Thr His Phe Asp Ile Gln Met Pro Gly Gly Gly
    440                 445                 450

CTC GGC ATC TTC GAC GGC TGC ACC CCG CAG TTC GGC TTC ACG TTC CCC        536
Leu Gly Ile Phe Asp Gly Cys Thr Pro Gln Phe Gly Phe Thr Phe Pro
455                 460                 465                 470

GGC AAC CGC TAC GGC GGT ACC ACG AGC CGC AGC CAG TGC GCC GAG CTG        584
Gly Asn Arg Tyr Gly Gly Thr Thr Ser Arg Ser Gln Cys Ala Glu Leu
                475                 480                 485

CCC TCC GTC CTC CGT GAC GGC TGC CAC TGG CGT TAC GAC TGG TTC AAC        632
Pro Ser Val Leu Arg Asp Gly Cys His Trp Arg Tyr Asp Trp Phe Asn
                490                 495                 500

GAT GCC GAC AAC CCC AAC GTC AAC TGG CGC CGC GTC CGA TGC CCG GCG        680
Asp Ala Asp Asn Pro Asn Val Asn Trp Arg Arg Val Arg Cys Pro Ala
    505                 510                 515

GCC CTC ACG AAC CGC TCC GGC TGC GTC CGC AAC GAC GAC AAC AGC TAC        728
Ala Leu Thr Asn Arg Ser Gly Cys Val Arg Asn Asp Asp Asn Ser Tyr
    520                 525                 530

CCC GTC TTC GAG CCC GGC ACG GGC ACC CCG CCG ACC CCC ACG ACC ACG        776
Pro Val Phe Glu Pro Gly Thr Gly Thr Pro Pro Thr Pro Thr Thr Thr
535                 540                 545                 550

ACT ACC AGC TCC CCT CCT CAG CCC ACC AAC GGC GGA GGC GGC GGC ACT        824
Thr Thr Ser Ser Pro Pro Gln Pro Thr Asn Gly Gly Gly Gly Gly Thr
                555                 560                 565

TCT CCT CAC TGG GGC CAG TGC GGC GGC CAG GGC TGG TCT GGC CCG ACG        872
Ser Pro His Trp Gly Gln Cys Gly Gly Gln Gly Trp Ser Gly Pro Thr
                570                 575                 580

GCC TGT GCC GGT GGG TCG ACC TGC AAC CTG ATC AAC CCG TGG TAC TCC        920
Ala Cys Ala Gly Gly Ser Thr Cys Asn Leu Ile Asn Pro Trp Tyr Ser
                585                 590                 595

CAG TGC ATT CCC AAC TAAGTGATCC GGGCATTGCG GTCGAAAGGG GACCGTTAGT        975
Gln Cys Ile Pro Asn
        600

CGACAAGGCC CAGCCAGACC TCAGGCAGGT GGCTGCCATG GCAGATTGTA TATAGTCTTC     1035

CGAGTACATA CTATTGAATG AAAATAAGAG CGGCTCGGAC CATGAGCAGA TGCCATTTGA     1095

TAAAAAAAAA AAAAAAAAA AAAAAAAAA AAAAAAAAAA AAAAAAAAAA AAAAAAAA        1154

(2) INFORMATION FOR SEQ ID NO: 8:

(i) SEQUENCE CHARACTERISTICS:
        (A) LENGTH: 295 amino acids
        (B) TYPE: amino acid
        (D) TOPOLOGY: linear (ii) MOLECULE TYPE: protein (xi) SEQUENCE DESCRIPTION: SEQ ID NO: 8:

Met Arg Ser Thr Ser Ile Leu Ile Gly Leu Val Ala Gly Val Ala Ala
  1               5                  10                  15

Gln Ser Ser Gly Ser Gly His Thr Thr Arg Tyr Trp Asp Cys Cys Lys
                20                  25                  30

Pro Ser Cys Ala Trp Asp Glu Lys Ala Ala Val Ser Arg Pro Val Thr
            35                  40                  45

Thr Cys Asp Arg Asn Asn Ser Pro Leu Ser Pro Gly Ala Val Ser Gly
        50                  55                  60

Cys Asp Pro Asn Gly Val Ala Phe Thr Cys Asn Asp Asn Gln Pro Trp
 65                  70                  75                  80

Ala Val Asn Asn Asn Val Ala Tyr Gly Phe Ala Ala Thr Ala Phe Pro
```

```
                         85                  90                  95
Gly Gly Asn Glu Ala Ser Trp Cys Cys Ala Cys Tyr Ala Leu Gln Phe
                100                 105                 110

Thr Ser Gly Pro Val Ala Gly Lys Thr Met Val Gln Ser Thr Asn
        115                 120                 125

Thr Gly Gly Asp Leu Ser Gly Thr His Phe Asp Ile Gln Met Pro Gly
    130                 135                 140

Gly Gly Leu Gly Ile Phe Asp Gly Cys Thr Pro Gln Phe Gly Phe Thr
145                 150                 155                 160

Phe Pro Gly Asn Arg Tyr Gly Gly Thr Thr Ser Arg Ser Gln Cys Ala
                165                 170                 175

Glu Leu Pro Ser Val Leu Arg Asp Gly Cys His Trp Arg Tyr Asp Trp
        180                 185                 190

Phe Asn Asp Ala Asp Asn Pro Asn Val Asn Trp Arg Arg Val Arg Cys
                195                 200                 205

Pro Ala Ala Leu Thr Asn Arg Ser Gly Cys Val Arg Asn Asp Asp Asn
210                 215                 220

Ser Tyr Pro Val Phe Glu Pro Gly Thr Gly Thr Pro Thr Pro Thr
225                 230                 235                 240

Thr Thr Thr Thr Ser Ser Pro Pro Gln Pro Thr Asn Gly Gly Gly Gly
                245                 250                 255

Gly Thr Ser Pro His Trp Gly Gln Cys Gly Gly Gln Gly Trp Ser Gly
                260                 265                 270

Pro Thr Ala Cys Ala Gly Gly Ser Thr Cys Asn Leu Ile Asn Pro Trp
                275                 280                 285

Tyr Ser Gln Cys Ile Pro Asn
        290                 295

(2) INFORMATION FOR SEQ ID NO: 9:

(i) SEQUENCE CHARACTERISTICS:
        (A) LENGTH: 1423 base pairs
        (B) TYPE: nucleic acid
        (C) STRANDEDNESS: single
        (D) TOPOLOGY: linear (ii) MOLECULE TYPE: cDNA (ix) FEATURE:
         (A) NAME/KEY: CDS
         (B) LOCATION: 110..1156

(xi) SEQUENCE DESCRIPTION: SEQ ID NO: 9:

AAAGTTCTGG CCGGAACAGA TCTCCGTTGT CGATCTTCGA TTTTCCAGAC TCAGTCTGTG      60

ACACTCCTTC AATCCACATT CCTTTACTTC TTCGTCACTC ATTCACATC ATG ATT        115
                                                       Met Ile

TCA GCT TGG ATT CTC CTG GGG CTG GTA GGC GCC GTG CCC TCC TCC GTC      163
Ser Ala Trp Ile Leu Leu Gly Leu Val Gly Ala Val Pro Ser Ser Val
        300                 305                 310

ATG GCC GCC TCG GGC AAA GGC CAC ACC ACC CGC TAC TGG GAT TGC TGC      211
Met Ala Ala Ser Gly Lys Gly His Thr Thr Arg Tyr Trp Asp Cys Cys
        315                 320                 325

AAG ACT TCT TGC GCA TGG GAG GGC AAG GCA TCC GTC TCC GAG CCT GTC      259
Lys Thr Ser Cys Ala Trp Glu Gly Lys Ala Ser Val Ser Glu Pro Val
330                 335                 340                 345

CTG ACC TGT AAC AAG CAG GAC AAC CCC ATC GTC GAT GCC AAC GCC AGA      307
Leu Thr Cys Asn Lys Gln Asp Asn Pro Ile Val Asp Ala Asn Ala Arg
                350                 355                 360
```

```
AGC GGC TGC GAC GGC GGC GGG GCA TTT GCC TGT ACC AAC AAT TCC CCT      355
Ser Gly Cys Asp Gly Gly Gly Ala Phe Ala Cys Thr Asn Asn Ser Pro
            365                 370                 375

TGG GCC GTG AGC GAG GAC CTG GCC TAC GGA TTT GCT GCC ACA GCC CTC      403
Trp Ala Val Ser Glu Asp Leu Ala Tyr Gly Phe Ala Ala Thr Ala Leu
            380                 385                 390

AGC GGC GGC ACT GAG GGC AGC TGG TGC TGC GCG TGT TAC GCC ATC ACA      451
Ser Gly Gly Thr Glu Gly Ser Trp Cys Cys Ala Cys Tyr Ala Ile Thr
        395                 400                 405

TTC ACG AGT GGC CCT GTG GCT GGC AAG AAG ATG GTC GTC CAG TCC ACG      499
Phe Thr Ser Gly Pro Val Ala Gly Lys Lys Met Val Val Gln Ser Thr
410                 415                 420                 425

AAC ACG GGA GGC GAC CTG TCC AAC AAC CAC TTT GAC CTG ATG ATT CCC      547
Asn Thr Gly Gly Asp Leu Ser Asn Asn His Phe Asp Leu Met Ile Pro
                430                 435                 440

GGT GGA GGC CTC GGC ATC TTT GAC GGT TGC TCG GCT CAG TTC GGA CAA      595
Gly Gly Gly Leu Gly Ile Phe Asp Gly Cys Ser Ala Gln Phe Gly Gln
                445                 450                 455

CTT CTT CCC GGC GAG CGT TAC GGA GGT GTT TCG TCC CGC TCT CAA TGC      643
Leu Leu Pro Gly Glu Arg Tyr Gly Gly Val Ser Ser Arg Ser Gln Cys
            460                 465                 470

GAT GGC ATG CCC GAG CTC TTG AAA GAC GGT TGC CAG TGG CGC TTC GAC      691
Asp Gly Met Pro Glu Leu Leu Lys Asp Gly Cys Gln Trp Arg Phe Asp
        475                 480                 485

TGG TTC AAG AAC TCA GAC AAC CCT GAC ATC GAG TTC GAG CAG GTC CAG      739
Trp Phe Lys Asn Ser Asp Asn Pro Asp Ile Glu Phe Glu Gln Val Gln
490                 495                 500                 505

TGT CCC AAA GAG CTC ATT GCG GTC TCT GGG TGC GTC CGT GAC GAC GAT      787
Cys Pro Lys Glu Leu Ile Ala Val Ser Gly Cys Val Arg Asp Asp Asp
                510                 515                 520

AGC AGC TTT CCC GTC TTC CAA GGT TCG GGC TCA GGA GAT GTC AAC CCA      835
Ser Ser Phe Pro Val Phe Gln Gly Ser Gly Ser Gly Asp Val Asn Pro
            525                 530                 535

CCT CCC AAG CCG ACT ACG ACT ACG ACC TCG TCA AAG CCG AAA ACA ACC      883
Pro Pro Lys Pro Thr Thr Thr Thr Thr Ser Ser Lys Pro Lys Thr Thr
        540                 545                 550

TCT GCA CCA TCC ACT CTC TCG AAC CCA TCC GCC CCT CAA CAG CCA GGG      931
Ser Ala Pro Ser Thr Leu Ser Asn Pro Ser Ala Pro Gln Gln Pro Gly
555                 560                 565

AAC ACT GAT AGA CCT GCC GAG ACA ACC ACT ACC AAG CTG CCT GCC CTG      979
Asn Thr Asp Arg Pro Ala Glu Thr Thr Thr Thr Lys Leu Pro Ala Leu
570                 575                 580                 585

CCG GCC ACG ACG AGC AGC CCT GCT GTC TCA GTT CCT TCG TCC AGC GCT     1027
Pro Ala Thr Thr Ser Ser Pro Ala Val Ser Val Pro Ser Ser Ser Ala
                590                 595                 600

CGC GTG CCT TTG TGG GGG CAA TGC GAC TCG GAA GCT TCA TGG GAC GCA     1075
Arg Val Pro Leu Trp Gly Gln Cys Asp Ser Glu Ala Ser Trp Asp Ala
            605                 610                 615

CCT AAG AAG TGT GCA AAG GGC ACC AAG TGT GTC TAC GTC AAC GAC TGG     1123
Pro Lys Lys Cys Ala Lys Gly Thr Lys Cys Val Tyr Val Asn Asp Trp
        620                 625                 630

TAC TCT CAA TGC CAG CCG AAG AAC TCT TGT GCT TGAGAAGCAA TGCTCACA     1176
Tyr Ser Gln Cys Gln Pro Lys Asn Ser Cys Ala
        635                 640

ATGTCCTCTT GTCACCCCTT CTTTTCATTC CCAAACATAC TTACTGTATT ATTATTTC    1236

ATGCTTCATT TCTTGCTTGT TTCTGTCTTT CCTGCACGCA GCTTTCAACG ATACCCTT    1296

TGCGATTGCC CTACGATCAG ATGATGGGCA CGACATGGAG GATGGTTTGG GCACTCAC    1356
```

```
GTTCAGGACG GGAAAATTTA TTAGGGCTGA GATCCGTGAA TTGACTTCAT TTCGGCGG    1416

TGTCTGC                                                            1423
```

(2) INFORMATION FOR SEQ ID NO: 10:

(i) SEQUENCE CHARACTERISTICS:
        (A) LENGTH: 349 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Ile Ser Ala Trp Ile Leu Leu Gly Leu Val Gly Ala Val Pro Ser
 1               5                  10                  15

Ser Val Met Ala Ala Ser Gly Lys Gly His Thr Thr Arg Tyr Trp Asp
                20                  25                  30

Cys Cys Lys Thr Ser Cys Ala Trp Glu Gly Lys Ala Ser Val Ser Glu
            35                  40                  45

Pro Val Leu Thr Cys Asn Lys Gln Asp Asn Pro Ile Val Asp Ala Asn
        50                  55                  60

Ala Arg Ser Gly Cys Asp Gly Gly Ala Phe Ala Cys Thr Asn Asn
 65                 70                  75                  80

Ser Pro Trp Ala Val Ser Glu Asp Leu Ala Tyr Gly Phe Ala Ala Thr
                85                  90                  95

Ala Leu Ser Gly Gly Thr Glu Gly Ser Trp Cys Cys Ala Cys Tyr Ala
            100                 105                 110

Ile Thr Phe Thr Ser Gly Pro Val Ala Gly Lys Lys Met Val Val Gln
        115                 120                 125

Ser Thr Asn Thr Gly Gly Asp Leu Ser Asn Asn His Phe Asp Leu Met
130                 135                 140

Ile Pro Gly Gly Gly Leu Gly Ile Phe Asp Gly Cys Ser Ala Gln Phe
145                 150                 155                 160

Gly Gln Leu Leu Pro Gly Glu Arg Tyr Gly Gly Val Ser Ser Arg Ser
                165                 170                 175

Gln Cys Asp Gly Met Pro Glu Leu Leu Lys Asp Gly Cys Gln Trp Arg
            180                 185                 190

Phe Asp Trp Phe Lys Asn Ser Asp Asn Pro Asp Ile Glu Phe Glu Gln
        195                 200                 205

Val Gln Cys Pro Lys Glu Leu Ile Ala Val Ser Gly Cys Val Arg Asp
    210                 215                 220

Asp Asp Ser Ser Phe Pro Val Phe Gln Gly Ser Gly Ser Gly Asp Val
225                 230                 235                 240

Asn Pro Pro Pro Lys Pro Thr Thr Thr Thr Ser Ser Lys Pro Lys
                245                 250                 255

Thr Thr Ser Ala Pro Ser Thr Leu Ser Asn Pro Ser Ala Pro Gln Gln
            260                 265                 270

Pro Gly Asn Thr Asp Arg Pro Ala Glu Thr Thr Thr Lys Leu Pro
        275                 280                 285

Ala Leu Pro Ala Thr Thr Ser Ser Pro Ala Val Ser Val Pro Ser Ser
    290                 295                 300

Ser Ala Arg Val Pro Leu Trp Gly Gln Cys Asp Ser Glu Ala Ser Trp
305                 310                 315                 320

Asp Ala Pro Lys Lys Cys Ala Lys Gly Thr Lys Cys Val Tyr Val Asn
                325                 330                 335
```

```
Asp Trp Tyr Ser Gln Cys Gln Pro Lys Asn Ser Cys Ala
        340                 345
```

(2) INFORMATION FOR SEQ ID NO: 11:

(i) SEQUENCE CHARACTERISTICS:
        (A) LENGTH: 1174 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 60..956

(xi) SEQUENCE DESCRIPTION: SEQ ID NO: 11:

```
GAGCAGCACC CCTCAAGCTG TACAGTTTCC ACCCCGCTCT CTTTTCTTCG GCCCCCAGG        59

ATG CGC TCT ACT CCC GTT CTT CGC ACA ACC CTG GCC GCT GCA CTT CCT       107
Met Arg Ser Thr Pro Val Leu Arg Thr Thr Leu Ala Ala Ala Leu Pro
350         355                 360                 365

CTG GTC GCC TCC GCG GCC AGT GGC AGT GGC CAG TCC ACG AGA TAC TGG       155
Leu Val Ala Ser Ala Ala Ser Gly Ser Gly Gln Ser Thr Arg Tyr Trp
            370                 375                 380

GAC TGC TGC AAG CCG TCG TGC GCT TGG CCC GGG AAG GCC GCC GTC AGC       203
Asp Cys Cys Lys Pro Ser Cys Ala Trp Pro Gly Lys Ala Ala Val Ser
                385                 390                 395

CAA CCG GTC TAC GCG TGC GAT GCC AAC TTC CAG CGC CTG TCC GAC TTC       251
Gln Pro Val Tyr Ala Cys Asp Ala Asn Phe Gln Arg Leu Ser Asp Phe
            400                 405                 410

AAT GTC CAG TCG GGC TGC AAC GGC GGC TCG GCC TAC TCC TGC GCC GAC       299
Asn Val Gln Ser Gly Cys Asn Gly Gly Ser Ala Tyr Ser Cys Ala Asp
415                 420                 425

CAG ACT CCC TGG GCG GTG AAC GAC AAT CTC GCC TAC GGC TTC GCC GCG       347
Gln Thr Pro Trp Ala Val Asn Asp Asn Leu Ala Tyr Gly Phe Ala Ala
430                 435                 440                 445

ACG AGC ATC GCC GGC GGG TCC GAA TCC TCG TGG TGC TGC GCC TGC TAC       395
Thr Ser Ile Ala Gly Gly Ser Glu Ser Ser Trp Cys Cys Ala Cys Tyr
                450                 455                 460

GCG CTC ACC TTC ACT TCC GGT CCC GTC GCC GGC AAG ACA ATG GTG GTG       443
Ala Leu Thr Phe Thr Ser Gly Pro Val Ala Gly Lys Thr Met Val Val
            465                 470                 475

CAG TCA ACG AGC ACT GGC GGC GAC CTG GGA AGT AAC CAG TTC GAT ATC       491
Gln Ser Thr Ser Thr Gly Gly Asp Leu Gly Ser Asn Gln Phe Asp Ile
        480                 485                 490

GCC ATG CCC GGC GGC GGC GTG GGC ATC TTC AAC GGC TGC AGC TCG CAG       539
Ala Met Pro Gly Gly Gly Val Gly Ile Phe Asn Gly Cys Ser Ser Gln
    495                 500                 505

TTC GGC GGC CTC CCC GGC GCT CAA TAC GGC GGC ATT TCG TCG CGC GAC       587
Phe Gly Gly Leu Pro Gly Ala Gln Tyr Gly Gly Ile Ser Ser Arg Asp
510                 515                 520                 525

CAG TGC GAT TCC TTC CCC GCG CCG CTC AAG CCC GGC TGC CAG TGG CGG       635
Gln Cys Asp Ser Phe Pro Ala Pro Leu Lys Pro Gly Cys Gln Trp Arg
                530                 535                 540

TTT GAC TGG TTC CAG AAC GCC GAC AAC CCG ACG TTC ACG TTC CAG CAG       683
Phe Asp Trp Phe Gln Asn Ala Asp Asn Pro Thr Phe Thr Phe Gln Gln
            545                 550                 555

GTG CAG TGC CCC GCC GAG ATC GTT GCC CGC TCC GGC TGC AAG CGC AAC       731
Val Gln Cys Pro Ala Glu Ile Val Ala Arg Ser Gly Cys Lys Arg Asn
        560                 565                 570

GAC GAC TCC AGC TTC CCC GTC TTC ACC CCC CCA AGC GGT GGC AAC GGT       779
```

-continued

```
Asp Asp Ser Ser Phe Pro Val Phe Thr Pro Pro Ser Gly Gly Asn Gly
    575                 580                 585

GGC ACC GGG ACG CCC ACG TCG ACT GCG CCT GGG TCG GGC CAG ACG TCT      827
Gly Thr Gly Thr Pro Thr Ser Thr Ala Pro Gly Ser Gly Gln Thr Ser
590                 595                 600                 605

CCC GGC GGC GGC AGT GGC TGC ACG TCT CAG AAG TGG GCT CAG TGC GGT      875
Pro Gly Gly Gly Ser Gly Cys Thr Ser Gln Lys Trp Ala Gln Cys Gly
                    610                 615                 620

GGC ATC GGC TTC AGC GGA TGC ACC ACC TGT GTC TCT GGC ACC ACC TGC      923
Gly Ile Gly Phe Ser Gly Cys Thr Thr Cys Val Ser Gly Thr Thr Cys
                625                 630                 635

CAG AAG TTG AAC GAC TAC TAC TCG CAG TGC CTC TAAACAGCTT TTCGCACGAG    976
Gln Lys Leu Asn Asp Tyr Tyr Ser Gln Cys Leu
                640                 645

GTGGCGGGAC GGAGCAAGGA GACCGTCAAC TTCGTCATGC ATATTTTTTG AGCGCTCAAT   1036

ACATACATAA CCTTCGATTC TTGTACATAG CACGCCGGTA CACATCTCAC ACCGACTTTG   1096

GGGGCGGAAT CAGGCCCGTT TTAAAAAAAA AAAAAAAAAA AAAAAAAAAA AAAAAAAAAA   1156

AAAAAAAAAA AAAAAAAA                                                 1174
```

(2) INFORMATION FOR SEQ ID NO: 12:

(i) SEQUENCE CHARACTERISTICS:
        (A) LENGTH: 299 amino acids
        (B) TYPE: amino acid
        (D) TOPOLOGY: linear (ii) MOLECULE TYPE: protein (xi) SEQUENCE DESCRIPTION: SEQ ID NO: 12:

```
Met Arg Ser Thr Pro Val Leu Arg Thr Thr Leu Ala Ala Ala Leu Pro
1               5                   10                  15

Leu Val Ala Ser Ala Ala Ser Gly Ser Gly Gln Ser Thr Arg Tyr Trp
                20                  25                  30

Asp Cys Cys Lys Pro Ser Cys Ala Trp Pro Gly Lys Ala Ala Val Ser
            35                  40                  45

Gln Pro Val Tyr Ala Cys Asp Ala Asn Phe Gln Arg Leu Ser Asp Phe
        50                  55                  60

Asn Val Gln Ser Gly Cys Asn Gly Gly Ser Ala Tyr Ser Cys Ala Asp
65                  70                  75                  80

Gln Thr Pro Trp Ala Val Asn Asp Asn Leu Ala Tyr Gly Phe Ala Ala
                85                  90                  95

Thr Ser Ile Ala Gly Ser Glu Ser Ser Trp Cys Cys Ala Cys Tyr
                    100                 105                 110

Ala Leu Thr Phe Thr Ser Gly Pro Val Ala Gly Lys Thr Met Val Val
            115                 120                 125

Gln Ser Thr Ser Thr Gly Gly Asp Leu Gly Ser Asn Gln Phe Asp Ile
        130                 135                 140

Ala Met Pro Gly Gly Gly Val Gly Ile Phe Asn Gly Cys Ser Ser Gln
145                 150                 155                 160

Phe Gly Gly Leu Pro Gly Ala Gln Tyr Gly Gly Ile Ser Ser Arg Asp
                165                 170                 175

Gln Cys Asp Ser Phe Pro Ala Pro Leu Lys Pro Gly Cys Gln Trp Arg
            180                 185                 190

Phe Asp Trp Phe Gln Asn Ala Asp Asn Pro Thr Phe Thr Phe Gln Gln
        195                 200                 205

Val Gln Cys Pro Ala Glu Ile Val Ala Arg Ser Gly Cys Lys Arg Asn
```

```
         210                 215                 220
Asp Asp Ser Ser Phe Pro Val Phe Thr Pro Pro Ser Gly Gly Asn Gly
225                 230                 235                 240

Gly Thr Gly Thr Pro Thr Ser Thr Ala Pro Gly Ser Gly Gln Thr Ser
                245                 250                 255

Pro Gly Gly Gly Ser Gly Cys Thr Ser Gln Lys Trp Ala Gln Cys Gly
            260                 265                 270

Gly Ile Gly Phe Ser Gly Cys Thr Thr Cys Val Ser Gly Thr Thr Cys
        275                 280                 285

Gln Lys Leu Asn Asp Tyr Tyr Ser Gln Cys Leu
    290                 295
```

(2) INFORMATION FOR SEQ ID NO: 13:

(i) SEQUENCE CHARACTERISTICS:
        (A) LENGTH: 913 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 41..706

(xi) SEQUENCE DESCRIPTION: SEQ ID NO: 13:

```
GCACTATTCT CAGCTCCATT CTCCCTTGAA GTAATTCACC ATG TTC TCT CCG CTC      55
                                            Met Phe Ser Pro Leu
                                                300

TGG GCC CTG TCG GCT CTG CTC CTA TTT CCT GCC ACT GAA GCC ACT AGC     103
Trp Ala Leu Ser Ala Leu Leu Leu Phe Pro Ala Thr Glu Ala Thr Ser
305                 310                 315                 320

GGC GTG ACA ACC AGG TAC TGG GAC TGC TGC AAG CCG TCT TGT GCT TGG     151
Gly Val Thr Thr Arg Tyr Trp Asp Cys Cys Lys Pro Ser Cys Ala Trp
            325                 330                 335

ACG GGC AAA GCA TCC GTC TCC AAG CCC GTC GGA ACC TGC GAC ATC AAC     199
Thr Gly Lys Ala Ser Val Ser Lys Pro Val Gly Thr Cys Asp Ile Asn
        340                 345                 350

GAC AAC GCC CAG ACG CCG AGC GAT CTG CTC AAG TCG TCC TGT GAT GGC     247
Asp Asn Ala Gln Thr Pro Ser Asp Leu Leu Lys Ser Ser Cys Asp Gly
    355                 360                 365

GGC AGC GCC TAC TAC TGC AGC AAC CAG GGC CCA TGG GCC GTG AAC GAC     295
Gly Ser Ala Tyr Tyr Cys Ser Asn Gln Gly Pro Trp Ala Val Asn Asp
370                 375                 380

AGC CTT TCC TAC GGC TTC GCT GCC GCC AAG CTG TCC GGA AAG CAG GAG     343
Ser Leu Ser Tyr Gly Phe Ala Ala Ala Lys Leu Ser Gly Lys Gln Glu
385                 390                 395                 400

ACT GAT TGG TGC TGT GGC TGC TAC AAG CTC ACA TTC ACC TCC ACC GCC     391
Thr Asp Trp Cys Cys Gly Cys Tyr Lys Leu Thr Phe Thr Ser Thr Ala
            405                 410                 415

GTT TCC GGC AAG CAA ATG ATC GTG CAA ATC ACG AAC ACG GGC GGC GAC     439
Val Ser Gly Lys Gln Met Ile Val Gln Ile Thr Asn Thr Gly Gly Asp
        420                 425                 430

CTC GGC AAC AAC CAC TTC GAC ATC GCC ATG CCG GGC GGC GGC GTC GGC     487
Leu Gly Asn Asn His Phe Asp Ile Ala Met Pro Gly Gly Gly Val Gly
    435                 440                 445

ATC TTC AAC GGG TGC TCC AAG CAA TGG AAC GGC ATC AAT CTG GGC AAC     535
Ile Phe Asn Gly Cys Ser Lys Gln Trp Asn Gly Ile Asn Leu Gly Asn
450                 455                 460

CAG TAT GGC GGC TTC ACT GAC CGC TCG CAA TGT GCG ACG CTC CCG TCC     583
```

```
Gln Tyr Gly Gly Phe Thr Asp Arg Ser Gln Cys Ala Thr Leu Pro Ser
465                 470                 475                 480

AAG TGG CAG GCC AGC TGC AAC TGG CGC TTC GAC TGG TTC GAG AAT GCC      631
Lys Trp Gln Ala Ser Cys Asn Trp Arg Phe Asp Trp Phe Glu Asn Ala
                        485                 490                 495

GAC AAC CCC ACC GTC GAT TGG GAG CCT GTC ACT TGC CCA CAG GAA TTG      679
Asp Asn Pro Thr Val Asp Trp Glu Pro Val Thr Cys Pro Gln Glu Leu
            500                 505                 510

GTC GCC CGG ACT GGC TGT TCC CGT ACC TAAGTGGGGG TGGAACCTCC            726
Val Ala Arg Thr Gly Cys Ser Arg Thr
            515                 520

ATGTGAATTG GTGTATATAG CTCCTGCCTG AGCATCCACC AGTTCGCATG TGTTGATCAG    786

GAGTTGTGTT GCCTTGCTAG GAAAGACTTT GTTGGAAACT TGCGTGTTTA TTCCAATTGA    846

ATAACCCTGT ATAGACCGGT CACATTTTTC TCTGAAAAAA AAAAAAAAAA AAAAAAAAA     906

AAAAAAA                                                              913

(2) INFORMATION FOR SEQ ID NO: 14:

(i) SEQUENCE CHARACTERISTICS:
        (A) LENGTH: 222 amino acids
        (B) TYPE: amino acid
        (D) TOPOLOGY: linear (ii) MOLECULE TYPE: protein (xi) SEQUENCE DESCRIPTION: SEQ ID NO: 14:

Met Phe Ser Pro Leu Trp Ala Leu Ser Ala Leu Leu Leu Phe Pro Ala
1               5                   10                  15

Thr Glu Ala Thr Ser Gly Val Thr Thr Arg Tyr Trp Asp Cys Cys Lys
            20                  25                  30

Pro Ser Cys Ala Trp Thr Gly Lys Ala Ser Val Ser Lys Pro Val Gly
        35                  40                  45

Thr Cys Asp Ile Asn Asp Asn Ala Gln Thr Pro Ser Asp Leu Leu Lys
    50                  55                  60

Ser Ser Cys Asp Gly Gly Ser Ala Tyr Tyr Cys Ser Asn Gln Gly Pro
65                  70                  75                  80

Trp Ala Val Asn Asp Ser Leu Ser Tyr Gly Phe Ala Ala Lys Leu
                85                  90                  95

Ser Gly Lys Gln Glu Thr Asp Trp Cys Cys Gly Cys Tyr Lys Leu Thr
                100                 105                 110

Phe Thr Ser Thr Ala Val Ser Gly Lys Gln Met Ile Val Gln Ile Thr
            115                 120                 125

Asn Thr Gly Gly Asp Leu Gly Asn Asn His Phe Asp Ile Ala Met Pro
    130                 135                 140

Gly Gly Gly Val Gly Ile Phe Asn Gly Cys Ser Lys Gln Trp Asn Gly
145                 150                 155                 160

Ile Asn Leu Gly Asn Gln Tyr Gly Gly Phe Thr Asp Arg Ser Gln Cys
                165                 170                 175

Ala Thr Leu Pro Ser Lys Trp Gln Ala Ser Cys Asn Trp Arg Phe Asp
            180                 185                 190

Trp Phe Glu Asn Ala Asp Asn Pro Thr Val Asp Trp Glu Pro Val Thr
        195                 200                 205

Cys Pro Gln Glu Leu Val Ala Arg Thr Gly Cys Ser Arg Thr
    210                 215                 220

(2) INFORMATION FOR SEQ ID NO: 15:
```

```
    (i) SEQUENCE CHARACTERISTICS:
        (A) LENGTH: 808 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 37..714

(xi) SEQUENCE DESCRIPTION: SEQ ID NO: 15:

CCGCTGCTGG GTATATAATG CTCAGACTTG GAACCA ATG GTC CAT CCA AAC ATG           54
                                       Met Val His Pro Asn Met
                                                           225

CTT AAA ACG CTC GCT CCA TTG ATC ATC TTG GCC GCC TCG GTC ACA GCG          102
Leu Lys Thr Leu Ala Pro Leu Ile Ile Leu Ala Ala Ser Val Thr Ala
    230                 235                 240

CAA ACA GCA GGA GTT ACG ACC CGC TAC TGG GAC TGC TGC AAG CCA AGC          150
Gln Thr Ala Gly Val Thr Thr Arg Tyr Trp Asp Cys Cys Lys Pro Ser
245                 250                 255                 260

TGT GGA TGG AGT GGA AAG GCT TCT GTT TCT GCT CCA GTC AGA ACT TGC          198
Cys Gly Trp Ser Gly Lys Ala Ser Val Ser Ala Pro Val Arg Thr Cys
                265                 270                 275

GAT CGT AAT GGA AAT ACA CTT GGC CCA GAC GTG AAA AGC GGA TGT GAT          246
Asp Arg Asn Gly Asn Thr Leu Gly Pro Asp Val Lys Ser Gly Cys Asp
            280                 285                 290

AGC GGT GGA ACG TCA TTC ACT TGC GCG AAC AAT GGT CCA TTT GCG ATT          294
Ser Gly Gly Thr Ser Phe Thr Cys Ala Asn Asn Gly Pro Phe Ala Ile
        295                 300                 305

GAC AAT AAC ACT GCA TAT GGT TTT GCT GCA GCC CAC TTA GCG GGC TCT          342
Asp Asn Asn Thr Ala Tyr Gly Phe Ala Ala Ala His Leu Ala Gly Ser
    310                 315                 320

AGC GAA GCA GCC TGG TGT TGC CAG TGC TAC GAA TTG ACG TTT ACG AGT          390
Ser Glu Ala Ala Trp Cys Cys Gln Cys Tyr Glu Leu Thr Phe Thr Ser
325                 330                 335                 340

GGA CCC GTA GTT GGG AAG AAA CTG ACC GTT CAA GTC ACA AAC ACG GGA          438
Gly Pro Val Val Gly Lys Lys Leu Thr Val Gln Val Thr Asn Thr Gly
                345                 350                 355

GGT GAC CTC GGA AAT AAT CAC TTT GAC CTG ATG ATC CCC GGT GGA GGT          486
Gly Asp Leu Gly Asn Asn His Phe Asp Leu Met Ile Pro Gly Gly Gly
            360                 365                 370

GTT GGC CTC TTC ACA CAA GGA TGT CCT GCT CAG TTT GGG AGC TGG AAC          534
Val Gly Leu Phe Thr Gln Gly Cys Pro Ala Gln Phe Gly Ser Trp Asn
        375                 380                 385

GGG GGT GCT CAA TAC GGG GGT GTG TCC AGC CGT GAC CAA TGC TCC CAA          582
Gly Gly Ala Gln Tyr Gly Gly Val Ser Ser Arg Asp Gln Cys Ser Gln
    390                 395                 400

CTT CCA GCA GCT GTG CAA GCT GGA TGT CAA TTC CGT TTC GAC TGG ATG          630
Leu Pro Ala Ala Val Gln Ala Gly Cys Gln Phe Arg Phe Asp Trp Met
405                 410                 415                 420

GGT GGC GCG GAT AAC CCC AAC GTC ACC TTC CGA CCT GTG ACC TGC CCA          678
Gly Gly Ala Asp Asn Pro Asn Val Thr Phe Arg Pro Val Thr Cys Pro
                425                 430                 435

GCG CAG CTC ACT AAT ATC TCG GGC TGT GTT CGT AAA TGATTCACGA               724
Ala Gln Leu Thr Asn Ile Ser Gly Cys Val Arg Lys
            440                 445

ATATGTAGTG TCGAATATGT ACATGTGTAT GTACTATAGC TTCAAAGATG GAGGGTCTGT        784

TTAAAAAAAA AAAAAAAAAA AAAA                                               808
```

(2) INFORMATION FOR SEQ ID NO: 16:

(i) SEQUENCE CHARACTERISTICS:
        (A) LENGTH: 226 amino acids
        (B) TYPE: amino acid
        (D) TOPOLOGY: linear (ii) MOLECULE TYPE: protein (xi) SEQUENCE DESCRIPTION: SEQ ID NO: 16:

```
Met Val His Pro Asn Met Leu Lys Thr Leu Ala Pro Leu Ile Ile Leu
 1               5                  10                  15

Ala Ala Ser Val Thr Ala Gln Thr Ala Gly Val Thr Thr Arg Tyr Trp
            20                  25                  30

Asp Cys Cys Lys Pro Ser Cys Gly Trp Ser Gly Lys Ala Ser Val Ser
            35                  40                  45

Ala Pro Val Arg Thr Cys Asp Arg Asn Gly Asn Thr Leu Gly Pro Asp
        50                  55                  60

Val Lys Ser Gly Cys Asp Ser Gly Gly Thr Ser Phe Thr Cys Ala Asn
 65                  70                  75                  80

Asn Gly Pro Phe Ala Ile Asp Asn Asn Thr Ala Tyr Gly Phe Ala Ala
                85                  90                  95

Ala His Leu Ala Gly Ser Ser Glu Ala Ala Trp Cys Cys Gln Cys Tyr
            100                 105                 110

Glu Leu Thr Phe Thr Ser Gly Pro Val Val Gly Lys Lys Leu Thr Val
            115                 120                 125

Gln Val Thr Asn Thr Gly Gly Asp Leu Gly Asn Asn His Phe Asp Leu
        130                 135                 140

Met Ile Pro Gly Gly Gly Val Gly Leu Phe Thr Gln Gly Cys Pro Ala
145                 150                 155                 160

Gln Phe Gly Ser Trp Asn Gly Gly Ala Gln Tyr Gly Gly Val Ser Ser
                165                 170                 175

Arg Asp Gln Cys Ser Gln Leu Pro Ala Ala Val Gln Ala Gly Cys Gln
            180                 185                 190

Phe Arg Phe Asp Trp Met Gly Gly Ala Asp Asn Pro Asn Val Thr Phe
        195                 200                 205

Arg Pro Val Thr Cys Pro Ala Gln Leu Thr Asn Ile Ser Gly Cys Val
    210                 215                 220

Arg Lys
225
```

(2) INFORMATION FOR SEQ ID NO: 17:

(i) SEQUENCE CHARACTERISTICS:
        (A) LENGTH: 1048 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 13..906

(xi) SEQUENCE DESCRIPTION: SEQ ID NO: 17:

```
GACTTGGAAC CA ATG GTC CAT CCA AAC ATG CTT AAA ACG CTC GCT CCA       48
              Met Val His Pro Asn Met Leu Lys Thr Leu Ala Pro
                              230                 235

TTG ATC ATC TTG GCC GCC TCG GTC ACA GCG CAA ACA GCA GGA GTT ACG     96
```

-continued

```
                Leu Ile Ile Leu Ala Ala Ser Val Thr Ala Gln Thr Ala Gly Val Thr
                240                 245                 250

ACC CGC TAC TGG GAC TGC TGC AAG CCA AGC TGT GGA TGG AGT GGA AAG          144
Thr Arg Tyr Trp Asp Cys Cys Lys Pro Ser Cys Gly Trp Ser Gly Lys
255                 260                 265                 270

GCT TCT GTT TCT GCT CCA GTC AGA ACT TGC GAT CGT AAT GGA AAT ACA          192
Ala Ser Val Ser Ala Pro Val Arg Thr Cys Asp Arg Asn Gly Asn Thr
                275                 280                 285

CTT GGC CCA GAC GTG AAA AGC GGA TGT GAT AGC GGT GGA ACG TCA TTC          240
Leu Gly Pro Asp Val Lys Ser Gly Cys Asp Ser Gly Gly Thr Ser Phe
                290                 295                 300

ACT TGC GCG AAC AAT GGT CCA TTT GCG ATT GAC AAT AAC ACT GCA TAT          288
Thr Cys Ala Asn Asn Gly Pro Phe Ala Ile Asp Asn Asn Thr Ala Tyr
                305                 310                 315

GGT TTT GCT GCA GCC CAC TTA GCG GGC TCT AGC GAA GCA GCC TGG TGT          336
Gly Phe Ala Ala Ala His Leu Ala Gly Ser Ser Glu Ala Ala Trp Cys
                320                 325                 330

TGC CAG TGC TAC GAA TTG ACG TTT ACG AGT GGA CCC GTA GTT GGG AAG          384
Cys Gln Cys Tyr Glu Leu Thr Phe Thr Ser Gly Pro Val Val Gly Lys
335                 340                 345                 350

AAA CTG ACC GTT CAA GTC ACA AAC ACG GGA GGT GAC CTC GGA AAT AAT          432
Lys Leu Thr Val Gln Val Thr Asn Thr Gly Gly Asp Leu Gly Asn Asn
                355                 360                 365

CAC TTT GAC CTG ATG ATC CCC GGT GGA GGT GTT GGC CTC TTC ACA CAA          480
His Phe Asp Leu Met Ile Pro Gly Gly Gly Val Gly Leu Phe Thr Gln
                370                 375                 380

GGA TGT CCT GCT CAG TTT GGG AGC TGG AAC GGG GGT GCT CAA TAC GGG          528
Gly Cys Pro Ala Gln Phe Gly Ser Trp Asn Gly Gly Ala Gln Tyr Gly
                385                 390                 395

GGT GTG TCC AGC CGT GAC CAA TGC TCC CAA CTT CCA GCA GCT GTG CAA          576
Gly Val Ser Ser Arg Asp Gln Cys Ser Gln Leu Pro Ala Ala Val Gln
400                 405                 410

GCT GGA TGT CAA TTC CGT TTC GAC TGG ATG GGT GGC GCG GAT AAC CCC          624
Ala Gly Cys Gln Phe Arg Phe Asp Trp Met Gly Gly Ala Asp Asn Pro
415                 420                 425                 430

AAC GTC ACC TTC CGA CCT GTG ACC TGC CCA GCG CAG CTC ACT AAT ATC          672
Asn Val Thr Phe Arg Pro Val Thr Cys Pro Ala Gln Leu Thr Asn Ile
                435                 440                 445

TCG GGC TGT GTT CGT AAA CCC TCC AGC AGC ACC AGC TCT CCG GTC AAC          720
Ser Gly Cys Val Arg Lys Pro Ser Ser Ser Thr Ser Ser Pro Val Asn
                450                 455                 460

CAG CCT ACC AGC ACC AGC ACC ACG TCC ACC TCC ACC ACC TCG AGC CCG          768
Gln Pro Thr Ser Thr Ser Thr Thr Ser Thr Ser Thr Thr Ser Ser Pro
                465                 470                 475

CCA GTC CAG CCT ACG ACT CCC AGC GGC TGC ACT GCT GAG AGG TGG GCT          816
Pro Val Gln Pro Thr Thr Pro Ser Gly Cys Thr Ala Glu Arg Trp Ala
480                 485                 490

CAG TGC GGC GGC AAT GGC TGG AGC GGC TGC ACC ACC TGC GTC GCT GGC          864
Gln Cys Gly Gly Asn Gly Trp Ser Gly Cys Thr Thr Cys Val Ala Gly
495                 500                 505                 510

AGC ACT TGC ACG AAG ATT AAT GAC TGG TAC CAT CAG TGC CTG                  906
Ser Thr Cys Thr Lys Ile Asn Asp Trp Tyr His Gln Cys Leu
                515                 520

TAGACGCAGG GCAGCTTGAG GGCCTTACTG GTGGCGCAAC GAAATGACAC TCCCAATCAC        966

TGTATTAGTT CTTGTACATA ATTTCGTCAT CCCTCCAGGG ATTGTCACAT AAATGCAATG       1026

AGGAACAATG AGTACAGAAT TC                                                1048
```

(2) INFORMATION FOR SEQ ID NO: 18:

(i) SEQUENCE CHARACTERISTICS:
    (A) LENGTH: 298 amino acids
    (B) TYPE: amino acid
    (D) TOPOLOGY: linear (ii) MOLECULE TYPE: protein (xi) SEQUENCE DESCRIPTION: SEQ ID NO: 18:

```
Met Val His Pro Asn Met Leu Lys Thr Leu Ala Pro Leu Ile Ile Leu
 1               5                  10                  15

Ala Ala Ser Val Thr Ala Gln Thr Ala Gly Val Thr Thr Arg Tyr Trp
             20                  25                  30

Asp Cys Cys Lys Pro Ser Cys Gly Trp Ser Gly Lys Ala Ser Val Ser
             35                  40                  45

Ala Pro Val Arg Thr Cys Asp Arg Asn Gly Asn Thr Leu Gly Pro Asp
 50                  55                  60

Val Lys Ser Gly Cys Asp Ser Gly Gly Thr Ser Phe Thr Cys Ala Asn
 65                  70                  75                  80

Asn Gly Pro Phe Ala Ile Asp Asn Asn Thr Ala Tyr Gly Phe Ala Ala
             85                  90                  95

Ala His Leu Ala Gly Ser Ser Glu Ala Ala Trp Cys Cys Gln Cys Tyr
            100                 105                 110

Glu Leu Thr Phe Thr Ser Gly Pro Val Val Gly Lys Lys Leu Thr Val
            115                 120                 125

Gln Val Thr Asn Thr Gly Gly Asp Leu Gly Asn Asn His Phe Asp Leu
            130                 135                 140

Met Ile Pro Gly Gly Gly Val Gly Leu Phe Thr Gln Gly Cys Pro Ala
145                 150                 155                 160

Gln Phe Gly Ser Trp Asn Gly Gly Ala Gln Tyr Gly Gly Val Ser Ser
            165                 170                 175

Arg Asp Gln Cys Ser Gln Leu Pro Ala Ala Val Gln Ala Gly Cys Gln
            180                 185                 190

Phe Arg Phe Asp Trp Met Gly Gly Ala Asp Asn Pro Asn Val Thr Phe
            195                 200                 205

Arg Pro Val Thr Cys Pro Ala Gln Leu Thr Asn Ile Ser Gly Cys Val
210                 215                 220

Arg Lys Pro Ser Ser Ser Thr Ser Ser Pro Val Asn Gln Pro Thr Ser
225                 230                 235                 240

Thr Ser Thr Thr Ser Thr Ser Thr Ser Ser Pro Pro Val Gln Pro
            245                 250                 255

Thr Thr Pro Ser Gly Cys Thr Ala Glu Arg Trp Ala Gln Cys Gly Gly
            260                 265                 270

Asn Gly Trp Ser Gly Cys Thr Thr Cys Val Ala Gly Ser Thr Cys Thr
            275                 280                 285

Lys Ile Asn Asp Trp Tyr His Gln Cys Leu
290                 295
```

(2) INFORMATION FOR SEQ ID NO: 19:

(i) SEQUENCE CHARACTERISTICS:
    (A) LENGTH: 1031 base pairs
    (B) TYPE: nucleic acid
    (C) STRANDEDNESS: single
    (D) TOPOLOGY: linear (ii) MOLECULE TYPE: cDNA (ix) FEATURE:

(A) NAME/KEY: CDS
         (B) LOCATION: 11..889

(xi) SEQUENCE DESCRIPTION: SEQ ID NO: 19:

CCATCCAAAC ATG CTT AAA ACG CTC GCT CCA TTG ATC ATC TTG GCC GCC         49
           Met Leu Lys Thr Leu Ala Pro Leu Ile Ile Leu Ala Ala
               300                 305                 310

TCG GTC ACA GCG CAA ACA GCA GGA GTT ACG ACC CGT TAC TGG GAC TGC        97
Ser Val Thr Ala Gln Thr Ala Gly Val Thr Thr Arg Tyr Trp Asp Cys
                315                 320                 325

TGC AAG CCA AGC TGT GGA TGG AGT GGA AAG GCT TCT GTT TCT GCT CCA       145
Cys Lys Pro Ser Cys Gly Trp Ser Gly Lys Ala Ser Val Ser Ala Pro
        330                 335                 340

GTC AGA ACT TGC GAT CGT AAT GGA AAT ACA CTT GGC CCA GAC GTG AAA       193
Val Arg Thr Cys Asp Arg Asn Gly Asn Thr Leu Gly Pro Asp Val Lys
    345                 350                 355

AGC GGA TGT GAT AGC GGT GGA ACG TCA TTC ACT TGC GCG AAC AAT GGT       241
Ser Gly Cys Asp Ser Gly Gly Thr Ser Phe Thr Cys Ala Asn Asn Gly
360                 365                 370                 375

CCA TTT GCG ATT GAC AAT AAC ACT GCA TAT GGT TTT GCT GCA GCC CAC       289
Pro Phe Ala Ile Asp Asn Asn Thr Ala Tyr Gly Phe Ala Ala Ala His
                380                 385                 390

TTA GCG GGC TCT AGC GAA GCA GCC TGG TGT TGC CAG TGC TAC GAA TTG       337
Leu Ala Gly Ser Ser Glu Ala Ala Trp Cys Cys Gln Cys Tyr Glu Leu
                395                 400                 405

ACG TTT ACG AGT GGA CCC GTA GTT GGG AAG AAA CTG ACC GTT CAA GTC       385
Thr Phe Thr Ser Gly Pro Val Val Gly Lys Lys Leu Thr Val Gln Val
        410                 415                 420

ACA AAC ACG GGA GGT GAC CTC GGA AAT AAT CAC TTT GAC CTG ATG ATC       433
Thr Asn Thr Gly Gly Asp Leu Gly Asn Asn His Phe Asp Leu Met Ile
    425                 430                 435

CCC GGT GGA GGT GTT GGC CTC TTC ACA CAA GGA TGT CCT GCT CAG TTT       481
Pro Gly Gly Gly Val Gly Leu Phe Thr Gln Gly Cys Pro Ala Gln Phe
440                 445                 450                 455

GGG AGC TGG AAC GGG GGT GCT CAA TAC GGG GGT GTG TCC AGC CGT GAC       529
Gly Ser Trp Asn Gly Gly Ala Gln Tyr Gly Gly Val Ser Ser Arg Asp
                460                 465                 470

CAA TGC TCC CAA CTT CCA GCA GCT GTG CAA GCT GGA TGT CAA TTC CGT       577
Gln Cys Ser Gln Leu Pro Ala Ala Val Gln Ala Gly Cys Gln Phe Arg
                475                 480                 485

TTC GAC TGG ATG GGT GGC GCG GAT AAC CCC AAC GTC ACC TTC CGA CCT       625
Phe Asp Trp Met Gly Gly Ala Asp Asn Pro Asn Val Thr Phe Arg Pro
        490                 495                 500

GTG ACC TGC CCA GCG CAG CTC ACT AAT ATC TCG GGC TGT GTT CGT AAA       673
Val Thr Cys Pro Ala Gln Leu Thr Asn Ile Ser Gly Cys Val Arg Lys
    505                 510                 515

CCC TCC AGC AGC ACC AGC TCT CCG GTC AAC CAG CCT ACC AGC ACC AGC       721
Pro Ser Ser Ser Thr Ser Ser Pro Val Asn Gln Pro Thr Ser Thr Ser
520                 525                 530                 535

ACC ACG TCC ACC TCC ACC ACC TCG AGC CCG CCA GTC CAG CCT ACG ACT       769
Thr Thr Ser Thr Ser Thr Thr Ser Ser Pro Pro Val Gln Pro Thr Thr
                540                 545                 550

CCC AGC GGC TGC ACT GCT GAG AGG TGG GCT CAG TGC GGC GGC AAT GGC       817
Pro Ser Gly Cys Thr Ala Glu Arg Trp Ala Gln Cys Gly Gly Asn Gly
                555                 560                 565

TGG AGC GGC TGC ACC ACC TGC GTC GCT GGC AGC ACT TGC ACG AAG ATT       865
Trp Ser Gly Cys Thr Thr Cys Val Ala Gly Ser Thr Cys Thr Lys Ile
        570                 575                 580

AAT GAC TGG TAC CAT CAG TGC CTG TAGACGCAGG GCAGCTTGAG GGCCTTACTG      919
Asn Asp Trp Tyr His Gln Cys Leu

```
                    585                      590
GTGGCGCAAC GAAATGACAC TCCCAATCAC TGTATTAGTT CTTGTACATA ATTTCGTCAT      979

CCCTCCAGGG ATTGTCACAT AAATGCAATG AGGAACAATG AGTACAGAAT TC             1031
```

(2) INFORMATION FOR SEQ ID NO: 20:

(i) SEQUENCE CHARACTERISTICS:
        (A) LENGTH: 293 amino acids
        (B) TYPE: amino acid
        (D) TOPOLOGY: linear (ii) MOLECULE TYPE: protein (xi) SEQUENCE DESCRIPTION: SEQ ID NO: 20:

```
Met Leu Lys Thr Leu Ala Pro Leu Ile Ile Leu Ala Ala Ser Val Thr
 1               5                  10                  15

Ala Gln Thr Ala Gly Val Thr Thr Arg Tyr Trp Asp Cys Cys Lys Pro
                20                  25                  30

Ser Cys Gly Trp Ser Gly Lys Ala Ser Val Ser Ala Pro Val Arg Thr
            35                  40                  45

Cys Asp Arg Asn Gly Asn Thr Leu Gly Pro Asp Val Lys Ser Gly Cys
        50                  55                  60

Asp Ser Gly Gly Thr Ser Phe Thr Cys Ala Asn Asn Gly Pro Phe Ala
65                  70                  75                  80

Ile Asp Asn Asn Thr Ala Tyr Gly Phe Ala Ala Ala His Leu Ala Gly
                85                  90                  95

Ser Ser Glu Ala Ala Trp Cys Cys Gln Cys Tyr Glu Leu Thr Phe Thr
                100                 105                 110

Ser Gly Pro Val Val Gly Lys Lys Leu Thr Val Gln Val Thr Asn Thr
            115                 120                 125

Gly Gly Asp Leu Gly Asn Asn His Phe Asp Leu Met Ile Pro Gly Gly
        130                 135                 140

Gly Val Gly Leu Phe Thr Gln Gly Cys Pro Ala Gln Phe Gly Ser Trp
145                 150                 155                 160

Asn Gly Gly Ala Gln Tyr Gly Gly Val Ser Ser Arg Asp Gln Cys Ser
                165                 170                 175

Gln Leu Pro Ala Ala Val Gln Ala Gly Cys Gln Phe Arg Phe Asp Trp
            180                 185                 190

Met Gly Gly Ala Asp Asn Pro Asn Val Thr Phe Arg Pro Val Thr Cys
        195                 200                 205

Pro Ala Gln Leu Thr Asn Ile Ser Gly Cys Val Arg Lys Pro Ser Ser
        210                 215                 220

Ser Thr Ser Ser Pro Val Asn Gln Pro Thr Ser Thr Ser Thr Thr Ser
225                 230                 235                 240

Thr Ser Thr Thr Ser Ser Pro Val Gln Pro Thr Thr Pro Ser Gly
                245                 250                 255

Cys Thr Ala Glu Arg Trp Ala Gln Cys Gly Gly Asn Gly Trp Ser Gly
            260                 265                 270

Cys Thr Thr Cys Val Ala Gly Ser Thr Cys Thr Lys Ile Asn Asp Trp
        275                 280                 285

Tyr His Gln Cys Leu
    290
```

(2) INFORMATION FOR SEQ ID NO: 21:

(i) SEQUENCE CHARACTERISTICS:

(A) LENGTH: 1132 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 42..971

(xi) SEQUENCE DESCRIPTION: SEQ ID NO: 21:

| | | |
|---|---|---|
| CAACAGTTCA AACACCTACA AGGTCCCGTG CCCTGTAGAC C ATG CGT TCC TCT<br>                                                                                                                                            Met Arg Ser Ser<br>                                                                                                                                            295 | 53 |
| GCA GTC CTC ATC GGC CTC GTG GCC GGT GTG GCC GCC CAG TCC TCT GGC<br>Ala Val Leu Ile Gly Leu Val Ala Gly Val Ala Ala Gln Ser Ser Gly<br>             300                 305                  310 | 101 |
| ACC GGC CGC ACC ACC AGA TAC TGG GAC TGC TGC AAG CCG TCC TGC GGG<br>Thr Gly Arg Thr Thr Arg Tyr Trp Asp Cys Cys Lys Pro Ser Cys Gly<br>315                         320                        325 | 149 |
| TGG GAC GAA AAG GCC TCC GTC AGC CAG CCC GTC AAG ACG TGC GAT AGG<br>Trp Asp Glu Lys Ala Ser Val Ser Gln Pro Val Lys Thr Cys Asp Arg<br>330                 335                    340                  345 | 197 |
| AAC AAC AAC CCT CTC GCG TCC ACG GCC AGG AGC GGC TGC GAT TCC AAC<br>Asn Asn Asn Pro Leu Ala Ser Thr Ala Arg Ser Gly Cys Asp Ser Asn<br>             350                 355                  360 | 245 |
| GGC GTC GCC TAC ACG TGC AAC GAT AAC CAG CCG TGG GCT GTC AAC GAT<br>Gly Val Ala Tyr Thr Cys Asn Asp Asn Gln Pro Trp Ala Val Asn Asp<br>           365                    370                  375 | 293 |
| AAC CTG GCC TAT GGT TTT GCT GCC ACG GCT TTC AGT GGT GGA TCG GAG<br>Asn Leu Ala Tyr Gly Phe Ala Ala Thr Ala Phe Ser Gly Gly Ser Glu<br>           380                    385                  390 | 341 |
| GCC AGC TGG TGC TGT GCC TGC TAT GCC CTT CAG TTC ACC TCC GGC CCT<br>Ala Ser Trp Cys Cys Ala Cys Tyr Ala Leu Gln Phe Thr Ser Gly Pro<br>395                        400                    405 | 389 |
| GTT GCG GGA AAG ACC ATG GTC GTC CAG TCG ACA AAC ACC GGC GGC GAC<br>Val Ala Gly Lys Thr Met Val Val Gln Ser Thr Asn Thr Gly Gly Asp<br>410                     415                    420                425 | 437 |
| CTC AGC GGC AAC CAC TTT GAC ATC CTC ATG CCC GGC GGC GGC CTG GGC<br>Leu Ser Gly Asn His Phe Asp Ile Leu Met Pro Gly Gly Gly Leu Gly<br>             430                 435                  440 | 485 |
| ATC TTC GAC GGC TGC ACC CCG CAA TGG GGC GTC AGC TTC CCC GGA AAC<br>Ile Phe Asp Gly Cys Thr Pro Gln Trp Gly Val Ser Phe Pro Gly Asn<br>           445                    450                  455 | 533 |
| CGC TAC GGC GGC ACC ACC AGC CGC AGC CAG TGC TCC CAA ATC CCC TCG<br>Arg Tyr Gly Gly Thr Thr Ser Arg Ser Gln Cys Ser Gln Ile Pro Ser<br>           460                    465                  470 | 581 |
| GCC CTG CAG CCC GGC TGC AAC TGG CGG TAC GAC TGG TTC AAC GAC GCC<br>Ala Leu Gln Pro Gly Cys Asn Trp Arg Tyr Asp Trp Phe Asn Asp Ala<br>475                        480                    485 | 629 |
| GAC AAC CCC GAC GTC TCG TGG CGC CGC GTC CAG TGC CCC GCC GCA CTC<br>Asp Asn Pro Asp Val Ser Trp Arg Arg Val Gln Cys Pro Ala Ala Leu<br>490                     495                    500                505 | 677 |
| ACC GAC CGC ACC GGC TGC CGC CGC TCC GAT GAC GGG AAC TAT CCC GTC<br>Thr Asp Arg Thr Gly Cys Arg Arg Ser Asp Asp Gly Asn Tyr Pro Val<br>             510                 515                  520 | 725 |
| TTC CAG CCC GGT CCG CCC CCG GCC ACG ACG ATC AGG ACA TCG ACT ACC<br>Phe Gln Pro Gly Pro Pro Pro Ala Thr Thr Ile Arg Thr Ser Thr Thr<br>           525                    530                  535 | 773 |
| ATC ACA GCC TCA TCG TCG TCT TCG TCT TCG TCG TCG TCG ACT ACG GCT<br>Ile Thr Ala Ser Ser Ser Ser Ser Ser Ser Ser Ser Ser Thr Thr Ala | 821 |

```
                540                 545                 550
GGT AGC CCG CCT GTG CCG ACT GGT GGT GGT AGT GGG CCA ACG TCG CCT      869
Gly Ser Pro Pro Val Pro Thr Gly Gly Gly Ser Gly Pro Thr Ser Pro
    555                 560                 565

GTC TGG GGA CAG TGC GGC GGT CAG GGA TGG AGT GGT CCT ACG CGT TGT      917
Val Trp Gly Gln Cys Gly Gly Gln Gly Trp Ser Gly Pro Thr Arg Cys
570                 575                 580                 585

GTT GCT GGG TCG ACA TGC AGT GTG GTC AAC CCG TGG TAC TCG CAG TGT      965
Val Ala Gly Ser Thr Cys Ser Val Val Asn Pro Trp Tyr Ser Gln Cys
                590                 595                 600

TTT CCT TAAGGAGCCT CTGGCTGAGC AGATCCTTTC GAAGAGGAGG GTCTCTCTGC      1021
Phe Pro

TCTTTCAGTC TGTTCAGGGA ACGGCCGTCT CGGCTACATT GTACATATCC CACCTCGTAT   1081

ATAGCTAGCT CATCTACACT TGTGATCTCC AAAAAAAAAA AAAAAAAAAA A            1132

(2) INFORMATION FOR SEQ ID NO: 22:

(i) SEQUENCE CHARACTERISTICS:
        (A) LENGTH: 310 amino acids
        (B) TYPE: amino acid
        (D) TOPOLOGY: linear (ii) MOLECULE TYPE: protein (xi) SEQUENCE DESCRIPTION: SEQ ID NO: 22:

Met Arg Ser Ser Ala Val Leu Ile Gly Leu Val Ala Gly Val Ala Ala
1               5                  10                  15

Gln Ser Ser Gly Thr Gly Arg Thr Thr Arg Tyr Trp Asp Cys Cys Lys
            20                  25                  30

Pro Ser Cys Gly Trp Asp Glu Lys Ala Ser Val Ser Gln Pro Val Lys
        35                  40                  45

Thr Cys Asp Arg Asn Asn Asn Pro Leu Ala Ser Thr Ala Arg Ser Gly
    50                  55                  60

Cys Asp Ser Asn Gly Val Ala Tyr Thr Cys Asn Asp Asn Gln Pro Trp
65                  70                  75                  80

Ala Val Asn Asp Asn Leu Ala Tyr Gly Phe Ala Ala Thr Ala Phe Ser
                85                  90                  95

Gly Gly Ser Glu Ala Ser Trp Cys Cys Ala Cys Tyr Ala Leu Gln Phe
            100                 105                 110

Thr Ser Gly Pro Val Ala Gly Lys Thr Met Val Val Gln Ser Thr Asn
        115                 120                 125

Thr Gly Gly Asp Leu Ser Gly Asn His Phe Asp Ile Leu Met Pro Gly
    130                 135                 140

Gly Gly Leu Gly Ile Phe Asp Gly Cys Thr Pro Gln Trp Gly Val Ser
145                 150                 155                 160

Phe Pro Gly Asn Arg Tyr Gly Gly Thr Thr Ser Arg Ser Gln Cys Ser
                165                 170                 175

Gln Ile Pro Ser Ala Leu Gln Pro Gly Cys Asn Trp Arg Tyr Asp Trp
            180                 185                 190

Phe Asn Asp Ala Asp Asn Pro Asp Val Ser Trp Arg Arg Val Gln Cys
        195                 200                 205

Pro Ala Ala Leu Thr Asp Arg Thr Gly Cys Arg Arg Ser Asp Asp Gly
    210                 215                 220

Asn Tyr Pro Val Phe Gln Pro Gly Pro Pro Ala Thr Thr Ile Arg
225                 230                 235                 240

Thr Ser Thr Thr Ile Thr Ala Ser Ser Ser Ser Ser Ser Ser Ser
```

```
                      245                 250                 255
Ser Thr Thr Ala Gly Ser Pro Val Pro Thr Gly Gly Ser Gly
            260                 265                 270

Pro Thr Ser Pro Val Trp Gly Gln Cys Gly Gln Gly Trp Ser Gly
            275                 280                 285

Pro Thr Arg Cys Val Ala Gly Ser Thr Cys Ser Val Val Asn Pro Trp
            290                 295                 300

Tyr Ser Gln Cys Phe Pro
305                 310

(2) INFORMATION FOR SEQ ID NO: 23:

(i) SEQUENCE CHARACTERISTICS:
        (A) LENGTH: 885 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..882

(xi) SEQUENCE DESCRIPTION: SEQ ID NO: 23:
```

| | |
|---|---|
| ATG TTC TCT CCG CTC TGG GCC CTG TCG GCT CTG CTC CTA TTT CCT GCC<br>Met Phe Ser Pro Leu Trp Ala Leu Ser Ala Leu Leu Leu Phe Pro Ala<br>                315                 320                 325 | 48 |
| ACT GAA GCC ACT AGC GGC GTG ACA ACC AGG TAC TGG GAC TGC TGC AAG<br>Thr Glu Ala Thr Ser Gly Val Thr Thr Arg Tyr Trp Asp Cys Cys Lys<br>            330                 335                 340 | 96 |
| CCG TCT TGT GCT TGG ACG GGC AAA GCA TCC GTC TCC AAG CCC GTC GGA<br>Pro Ser Cys Ala Trp Thr Gly Lys Ala Ser Val Ser Lys Pro Val Gly<br>            345                 350                 355 | 144 |
| ACC TGC GAC ATC AAC GAC AAC GCC CAG ACG CCG AGC GAT CTG CTC AAG<br>Thr Cys Asp Ile Asn Asp Asn Ala Gln Thr Pro Ser Asp Leu Leu Lys<br>            360                 365                 370 | 192 |
| TCG TCC TGT GAT GGC GGC AGC GCC TAC TAC TGC AGC AAC CAG GGC CCA<br>Ser Ser Cys Asp Gly Gly Ser Ala Tyr Tyr Cys Ser Asn Gln Gly Pro<br>375                 380                 385                 390 | 240 |
| TGG GCC GTG AAC GAC AGC CTT TCC TAC GGC TTC GCT GCC GCC AAG CTG<br>Trp Ala Val Asn Asp Ser Leu Ser Tyr Gly Phe Ala Ala Ala Lys Leu<br>            395                 400                 405 | 288 |
| TCC GGA AAG CAG GAG ACT GAT TGG TGC TGT GGC TGC TAC AAG CTC ACA<br>Ser Gly Lys Gln Glu Thr Asp Trp Cys Cys Gly Cys Tyr Lys Leu Thr<br>            410                 415                 420 | 336 |
| TTC ACC TCC ACC GCC GTT TCC GGC AAG CAA ATG ATC GTG CAA ATC ACG<br>Phe Thr Ser Thr Ala Val Ser Gly Lys Gln Met Ile Val Gln Ile Thr<br>            425                 430                 435 | 384 |
| AAC ACG GGC GGC GAC CTC GGC AAC AAC CAC TTC GAC ATC GCC ATG CCG<br>Asn Thr Gly Gly Asp Leu Gly Asn Asn His Phe Asp Ile Ala Met Pro<br>            440                 445                 450 | 432 |
| GGC GGC GGC GTC GGC ATC TTC AAC GGG TGC TCC AAG CAA TGG AAC GGC<br>Gly Gly Gly Val Gly Ile Phe Asn Gly Cys Ser Lys Gln Trp Asn Gly<br>455                 460                 465                 470 | 480 |
| ATC AAT CTG GGC AAC CAG TAT GGC GGC TTC ACT GAC CGC TCG CAA TGT<br>Ile Asn Leu Gly Asn Gln Tyr Gly Gly Phe Thr Asp Arg Ser Gln Cys<br>                475                 480                 485 | 528 |
| GCG ACG CTC CCG TCC AAG TGG CAG GCC AGC TGC AAC TGG CGC TTC GAC<br>Ala Thr Leu Pro Ser Lys Trp Gln Ala Ser Cys Asn Trp Arg Phe Asp<br>            490                 495                 500 | 576 |

```
TGG TTC GAG AAT GCC GAC AAC CCC ACC GTC GAT TGG GAG CCT GTC ACT      624
Trp Phe Glu Asn Ala Asp Asn Pro Thr Val Asp Trp Glu Pro Val Thr
        505                 510                 515

TGC CCA CAG GAA TTG GTC GCC CGG ACT GGC TGT TCC CGT ACC CCC TCC      672
Cys Pro Gln Glu Leu Val Ala Arg Thr Gly Cys Ser Arg Thr Pro Ser
520                 525                 530

AGC AGC ACC AGC TCT CCG GTC AAC CAG CCT ACC AGC ACC AGC ACC ACG      720
Ser Ser Thr Ser Ser Pro Val Asn Gln Pro Thr Ser Thr Ser Thr Thr
535                 540                 545                 550

TCC ACC TCC ACC ACC TCG AGC CCG CCA GTC CAG CCT ACG ACT CCC AGC      768
Ser Thr Ser Thr Thr Ser Ser Pro Pro Val Gln Pro Thr Thr Pro Ser
            555                 560                 565

GGC TGC ACT GCT GAG AGG TGG GCT CAG TGC GGC GGC AAT GGC TGG AGC      816
Gly Cys Thr Ala Glu Arg Trp Ala Gln Cys Gly Gly Asn Gly Trp Ser
        570                 575                 580

GGC TGC ACC ACC TGC GTC GCT GGC AGC ACT TGC ACG AAG ATT AAT GAC      864
Gly Cys Thr Thr Cys Val Ala Gly Ser Thr Cys Thr Lys Ile Asn Asp
585                 590                 595

TGG TAC CAT CAG TGC CTG TAG                                          885
Trp Tyr His Gln Cys Leu
    600
```

(2) INFORMATION FOR SEQ ID NO: 24:

(i) SEQUENCE CHARACTERISTICS:
        (A) LENGTH: 294 amino acids
        (B) TYPE: amino acid
        (D) TOPOLOGY: linear (ii) MOLECULE TYPE: protein (xi) SEQUENCE DESCRIPTION: SEQ ID NO: 24:

```
Met Phe Ser Pro Leu Trp Ala Leu Ser Ala Leu Leu Phe Pro Ala
  1               5                  10                  15

Thr Glu Ala Thr Ser Gly Val Thr Thr Arg Tyr Trp Asp Cys Cys Lys
                20                  25                  30

Pro Ser Cys Ala Trp Thr Gly Lys Ala Ser Val Ser Lys Pro Val Gly
            35                  40                  45

Thr Cys Asp Ile Asn Asp Asn Ala Gln Thr Pro Ser Asp Leu Leu Lys
        50                  55                  60

Ser Ser Cys Asp Gly Gly Ser Ala Tyr Tyr Cys Ser Asn Gln Gly Pro
65                  70                  75                  80

Trp Ala Val Asn Asp Ser Leu Ser Tyr Gly Phe Ala Ala Lys Leu
                85                  90                  95

Ser Gly Lys Gln Glu Thr Asp Trp Cys Cys Gly Cys Tyr Lys Leu Thr
            100                 105                 110

Phe Thr Ser Thr Ala Val Ser Gly Lys Gln Met Ile Val Gln Ile Thr
        115                 120                 125

Asn Thr Gly Gly Asp Leu Gly Asn Asn His Phe Asp Ile Ala Met Pro
    130                 135                 140

Gly Gly Gly Val Gly Ile Phe Asn Gly Cys Ser Lys Gln Trp Asn Gly
145                 150                 155                 160

Ile Asn Leu Gly Asn Gln Tyr Gly Gly Phe Thr Asp Arg Ser Gln Cys
                165                 170                 175

Ala Thr Leu Pro Ser Lys Trp Gln Ala Ser Cys Asn Trp Arg Phe Asp
            180                 185                 190

Trp Phe Glu Asn Ala Asp Asn Pro Thr Val Asp Trp Glu Pro Val Thr
        195                 200                 205
```

```
Cys Pro Gln Glu Leu Val Ala Arg Thr Gly Cys Ser Arg Thr Pro Ser
    210                 215                 220

Ser Ser Thr Ser Ser Pro Val Asn Gln Pro Thr Ser Thr Ser Thr Thr
225             230                 235                 240

Ser Thr Ser Thr Thr Ser Ser Pro Pro Val Gln Pro Thr Thr Pro Ser
            245                 250                 255

Gly Cys Thr Ala Glu Arg Trp Ala Gln Cys Gly Asn Gly Trp Ser
        260                 265                 270

Gly Cys Thr Thr Cys Val Ala Gly Ser Thr Cys Thr Lys Ile Asn Asp
        275                 280                 285

Trp Tyr His Gln Cys Leu
    290
```

(2) INFORMATION FOR SEQ ID NO: 25:

(i) SEQUENCE CHARACTERISTICS:
        (A) LENGTH: 425 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 12..425

(xi) SEQUENCE DESCRIPTION: SEQ ID NO: 25:

```
CAAGATACAA T ATG CGT TCC TCC ACT ATT TTG CAA ACC GGC CTG GTG GCC        50
             Met Arg Ser Ser Thr Ile Leu Gln Thr Gly Leu Val Ala
             295                 300                 305

GTT CTC CCC TTC GCC GTC CAG GCC GCC TCA GGA TCC GGC AAG TCC ACC         98
Val Leu Pro Phe Ala Val Gln Ala Ala Ser Gly Ser Gly Lys Ser Thr
        310                 315                 320

AGA TAT TGG GAC TGC TGC AAA CCA TCT TGT GCC TGG TCC GGC AAG GCT        146
Arg Tyr Trp Asp Cys Cys Lys Pro Ser Cys Ala Trp Ser Gly Lys Ala
325                 330                 335

TCT GTC AAC CGC CCT GTT CTC GCC TGC AAC GCA AAC AAC AAC CCG CTG        194
Ser Val Asn Arg Pro Val Leu Ala Cys Asn Ala Asn Asn Asn Pro Leu
340                 345                 350                 355

AAC GAC GCC AAC GTC AAG TCA GGA TGT GAT GGC GGT TCT GCA TAC ACC        242
Asn Asp Ala Asn Val Lys Ser Gly Cys Asp Gly Gly Ser Ala Tyr Thr
            360                 365                 370

TGT GCC AAC AAC TCT CCC TGG GCA GTG AAT GAC AAT CTG GCC TAC GGC        290
Cys Ala Asn Asn Ser Pro Trp Ala Val Asn Asp Asn Leu Ala Tyr Gly
        375                 380                 385

TTC GCG GCC ACA AAA CTC AGC GGG GGG ACC GAG TCA TCT TGG TGC TGC        338
Phe Ala Ala Thr Lys Leu Ser Gly Gly Thr Glu Ser Ser Trp Cys Cys
        390                 395                 400

GCC TGT TAT GCC CTC ACA TTC ACA TCG GGT CCT GTT TCT GGC AAA ACC        386
Ala Cys Tyr Ala Leu Thr Phe Thr Ser Gly Pro Val Ser Gly Lys Thr
405                 410                 415

TTG GTT GTC CAG TCT ACC AGT ACC GGT GGT GAT CTT GGC                    425
Leu Val Val Gln Ser Thr Ser Thr Gly Gly Asp Leu Gly
420                 425                 430
```

(2) INFORMATION FOR SEQ ID NO: 26:

(i) SEQUENCE CHARACTERISTICS:
        (A) LENGTH: 138 amino acids
        (B) TYPE: amino acid
        (D) TOPOLOGY: linear

```
     (ii) MOLECULE TYPE: protein (xi) SEQUENCE DESCRIPTION: SEQ ID NO: 26:

Met Arg Ser Ser Thr Ile Leu Gln Thr Gly Leu Val Ala Val Leu Pro
 1               5                  10                  15

Phe Ala Val Gln Ala Ala Ser Gly Ser Gly Lys Ser Thr Arg Tyr Trp
                 20                  25                  30

Asp Cys Cys Lys Pro Ser Cys Ala Trp Ser Gly Lys Ala Ser Val Asn
             35                  40                  45

Arg Pro Val Leu Ala Cys Asn Ala Asn Asn Pro Leu Asn Asp Ala
         50                  55                  60

Asn Val Lys Ser Gly Cys Asp Gly Gly Ser Ala Tyr Thr Cys Ala Asn
 65                  70                  75                  80

Asn Ser Pro Trp Ala Val Asn Asp Asn Leu Ala Tyr Gly Phe Ala Ala
                 85                  90                  95

Thr Lys Leu Ser Gly Gly Thr Glu Ser Ser Trp Cys Cys Ala Cys Tyr
                100                 105                 110

Ala Leu Thr Phe Thr Ser Gly Pro Val Ser Gly Lys Thr Leu Val Val
            115                 120                 125

Gln Ser Thr Ser Thr Gly Gly Asp Leu Gly
            130                 135

(2) INFORMATION FOR SEQ ID NO: 27:

(i) SEQUENCE CHARACTERISTICS:
         (A) LENGTH: 108 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: CDS
         (B) LOCATION: 1..108

(xi) SEQUENCE DESCRIPTION: SEQ ID NO: 27:

TCG GCT TGC GAT AAC GGT GGT GGC ACT GCA TAC ATG TGT GCC AGC CAG      48
Ser Ala Cys Asp Asn Gly Gly Gly Thr Ala Tyr Met Cys Ala Ser Gln
140                 145                 150

GAG CCG TGG GCA GTG AGC TCC AAC GTC GCG TAC GGC TTT GCT GCA GTT      96
Glu Pro Trp Ala Val Ser Ser Asn Val Ala Tyr Gly Phe Ala Ala Val
155                 160                 165                 170

AGA ATC AGC GGA                                                     108
Arg Ile Ser Gly (2) INFORMATION FOR SEQ ID NO: 28:

(i) SEQUENCE CHARACTERISTICS:
         (A) LENGTH: 36 amino acids
         (B) TYPE: amino acid
         (D) TOPOLOGY: linear (ii) MOLECULE TYPE: protein (xi) SEQUENCE DESCRIPTION: SEQ ID NO: 28:

Ser Ala Cys Asp Asn Gly Gly Gly Thr Ala Tyr Met Cys Ala Ser Gln
 1               5                  10                  15

Glu Pro Trp Ala Val Ser Ser Asn Val Ala Tyr Gly Phe Ala Ala Val
                 20                  25                  30

Arg Ile Ser Gly
            35
```

(2) INFORMATION FOR SEQ ID NO: 29:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..99

(xi) SEQUENCE DESCRIPTION: SEQ ID NO: 29:

```
GCC TGC AAC GCA AAC TTC CAG CGC ATC AGT GAC CCC AAC GCC AAG TCG      48
Ala Cys Asn Ala Asn Phe Gln Arg Ile Ser Asp Pro Asn Ala Lys Ser
            40                  45                  50

GGC TGC GAT GGT GGC TCG GCC TTC TCT TGC GCC AAA CAA ACC CCT TGG      96
Gly Cys Asp Gly Gly Ser Ala Phe Ser Cys Ala Lys Gln Thr Pro Trp
        55                  60                  65

GCC                                                                  99
Ala
```

(2) INFORMATION FOR SEQ ID NO: 30:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO: 30:

```
Ala Cys Asn Ala Asn Phe Gln Arg Ile Ser Asp Pro Asn Ala Lys Ser
 1               5                  10                  15

Gly Cys Asp Gly Gly Ser Ala Phe Ser Cys Ala Lys Gln Thr Pro Trp
            20                  25                  30

Ala
```

(2) INFORMATION FOR SEQ ID NO: 31:

(i) SEQUENCE CHARACTERISTICS:
        (A) LENGTH: 225 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..225

(xi) SEQUENCE DESCRIPTION: SEQ ID NO: 31:

```
GAC CAG CCG CTC GGC GGA CAA CGG ACG CGA CCA AGG AGC GCG TGC GAC      48
Asp Gln Pro Leu Gly Gly Gln Arg Thr Arg Pro Arg Ser Ala Cys Asp
        35                  40                  45

AAT GGC GGC TCT GCA TAC ATG TGC AGC AAC CAG AGC CCG TGG GCC GTC      96
Asn Gly Gly Ser Ala Tyr Met Cys Ser Asn Gln Ser Pro Trp Ala Val
 50                  55                  60                  65

GAC GAT TCT CTC AGT TAC GGA TGG GCT GCC GTT AGG ATC TAT GGA CAT     144
Asp Asp Ser Leu Ser Tyr Gly Trp Ala Ala Val Arg Ile Tyr Gly His
            70                  75                  80

ACC GAA ACT ACT TGG TGC TGC GCT TGC TAC GAG TTG ACT TTT ACC AGC     192
```

```
Thr Glu Thr Thr Trp Cys Cys Ala Cys Tyr Glu Leu Thr Phe Thr Ser
            85                  90                  95

GGT CCG GTT AGC GGC AAG AAG ATG ATT GTT CAG                              225
Gly Pro Val Ser Gly Lys Lys Met Ile Val Gln
            100                 105
```

(2) INFORMATION FOR SEQ ID NO: 32:

(i) SEQUENCE CHARACTERISTICS:
        (A) LENGTH: 75 amino acids
        (B) TYPE: amino acid
        (D) TOPOLOGY: linear (ii) MOLECULE TYPE: protein (xi) SEQUENCE DESCRIPTION: SEQ ID NO: 32:

```
Asp Gln Pro Leu Gly Gly Gln Arg Thr Arg Pro Arg Ser Ala Cys Asp
 1               5                  10                  15

Asn Gly Gly Ser Ala Tyr Met Cys Ser Asn Gln Ser Pro Trp Ala Val
            20                  25                  30

Asp Asp Ser Leu Ser Tyr Gly Trp Ala Ala Val Arg Ile Tyr Gly His
            35                  40                  45

Thr Glu Thr Thr Trp Cys Cys Ala Cys Tyr Glu Leu Thr Phe Thr Ser
        50                  55                  60

Gly Pro Val Ser Gly Lys Lys Met Ile Val Gln
65                  70                  75
```

(2) INFORMATION FOR SEQ ID NO: 33:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..177

(xi) SEQUENCE DESCRIPTION: SEQ ID NO: 33:

```
AGA AAC GAC AAC CCC ATC TCC AAC ACC AAC GCT GTC AAC GGT TGT GAG         48
Arg Asn Asp Asn Pro Ile Ser Asn Thr Asn Ala Val Asn Gly Cys Glu
                    80                  85                  90

GGT GGT GGT TCT GCT TAT GCT TGC ACC AAC TAC TCT CCC TGG GCT GTC         96
Gly Gly Gly Ser Ala Tyr Ala Cys Thr Asn Tyr Ser Pro Trp Ala Val
            95                  100                 105

AAC GAT GAG CTT GCC TAC GGT TTC GCT GCT ACC AAG ATC TCC GGT GGC        144
Asn Asp Glu Leu Ala Tyr Gly Phe Ala Ala Thr Lys Ile Ser Gly Gly
            110                 115                 120

TCC GAG GCC AGC TGG TGC TGT GCC TGC TAT CTA                            177
Ser Glu Ala Ser Trp Cys Cys Ala Cys Tyr Leu
            125                 130
```

(2) INFORMATION FOR SEQ ID NO: 34:

(i) SEQUENCE CHARACTERISTICS:
        (A) LENGTH: 59 amino acids
        (B) TYPE: amino acid
        (D) TOPOLOGY: linear (ii) MOLECULE TYPE: protein (xi) SEQUENCE DESCRIPTION: SEQ ID NO: 34:

```
Arg Asn Asp Asn Pro Ile Ser Asn Thr Asn Ala Val Asn Gly Cys Glu
 1               5                  10                  15

Gly Gly Gly Ser Ala Tyr Ala Cys Thr Asn Tyr Ser Pro Trp Ala Val
                 20                  25                  30

Asn Asp Glu Leu Ala Tyr Gly Phe Ala Ala Thr Lys Ile Ser Gly Gly
             35                  40                  45

Ser Glu Ala Ser Trp Cys Cys Ala Cys Tyr Leu
             50                  55
```

(2) INFORMATION FOR SEQ ID NO: 35:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..63

(xi) SEQUENCE DESCRIPTION: SEQ ID NO: 35:

```
AGC GGC TGT GAC GGT GGT TCT GCC TAC GCC TGT GCA AAC AAC TCC CCT        48
Ser Gly Cys Asp Gly Gly Ser Ala Tyr Ala Cys Ala Asn Asn Ser Pro
 60                  65                  70                  75

TGG GCT GTC AAC GAT                                                    63
Trp Ala Val Asn Asp
             80
```

(2) INFORMATION FOR SEQ ID NO: 36:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO: 36:

```
Ser Gly Cys Asp Gly Gly Ser Ala Tyr Ala Cys Ala Asn Asn Ser Pro
 1               5                  10                  15

Trp Ala Val Asn Asp
             20
```

(2) INFORMATION FOR SEQ ID NO: 37:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..177

(xi) SEQUENCE DESCRIPTION: SEQ ID NO: 37:

```
AAC CAG CCT GTC TTC ACT TGC GAC GCC AAA TTC CAG CGC ATC ACC GAC        48
Asn Gln Pro Val Phe Thr Cys Asp Ala Lys Phe Gln Arg Ile Thr Asp
             25                  30                  35

CCC AAT ACC AAG TCG GGC TGC GAT GGC GGC TCG GCC TTT TCG TGT GCT        96
Pro Asn Thr Lys Ser Gly Cys Asp Gly Gly Ser Ala Phe Ser Cys Ala
             40                  45                  50
```

```
GAC CAA ACC CCC TGG GCT CTG AAC GAC GAT TTC GCC TAT GGC TTC GCT    144
Asp Gln Thr Pro Trp Ala Leu Asn Asp Asp Phe Ala Tyr Gly Phe Ala
        55                  60                  65

GCC ACG GCT ATT TCG GGT GGA TCG GAA GCC TCG                        177
Ala Thr Ala Ile Ser Gly Gly Ser Glu Ala Ser
 70                  75                  80

(2) INFORMATION FOR SEQ ID NO: 38:

(i) SEQUENCE CHARACTERISTICS:
        (A) LENGTH: 59 amino acids
        (B) TYPE: amino acid
        (D) TOPOLOGY: linear (ii) MOLECULE TYPE: protein (xi) SEQUENCE DESCRIPTION: SEQ ID NO: 38:

Asn Gln Pro Val Phe Thr Cys Asp Ala Lys Phe Gln Arg Ile Thr Asp
 1               5                  10                  15

Pro Asn Thr Lys Ser Gly Cys Asp Gly Gly Ser Ala Phe Ser Cys Ala
                20                  25                  30

Asp Gln Thr Pro Trp Ala Leu Asn Asp Asp Phe Ala Tyr Gly Phe Ala
        35                  40                  45

Ala Thr Ala Ile Ser Gly Gly Ser Glu Ala Ser
 50                  55

(2) INFORMATION FOR SEQ ID NO: 39:

(i) SEQUENCE CHARACTERISTICS:
        (A) LENGTH: 153 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..153

(xi) SEQUENCE DESCRIPTION: SEQ ID NO: 39:

GTC TAC GCC TGC AAC GCA AAC TTC CAG CGC ATC ACC GAC GCC AAC GCC    48
Val Tyr Ala Cys Asn Ala Asn Phe Gln Arg Ile Thr Asp Ala Asn Ala
 60                  65                  70                  75

AAG TCC GGC TGC GAT GGC GGC TCC GCC TTC TCG TGC GCC AAC CAG ACC    96
Lys Ser Gly Cys Asp Gly Gly Ser Ala Phe Ser Cys Ala Asn Gln Thr
                 80                  85                  90

CCG TGG GCC GTG AGC GAC GAC TTT GCC TAC GGT TTC GCG GCT ACG GCG    144
Pro Trp Ala Val Ser Asp Asp Phe Ala Tyr Gly Phe Ala Ala Thr Ala
                 95                 100                 105

CTC GCC GGC                                                        153
Leu Ala Gly
        110

(2) INFORMATION FOR SEQ ID NO: 40:

(i) SEQUENCE CHARACTERISTICS:
        (A) LENGTH: 51 amino acids
        (B) TYPE: amino acid
        (D) TOPOLOGY: linear (ii) MOLECULE TYPE: protein (xi) SEQUENCE DESCRIPTION: SEQ ID NO: 40:

Val Tyr Ala Cys Asn Ala Asn Phe Gln Arg Ile Thr Asp Ala Asn Ala
```

```
              1               5                  10                  15
         Lys Ser Gly Cys Asp Gly Gly Ser Ala Phe Ser Cys Ala Asn Gln Thr
                         20                  25                  30

Pro Trp Ala Val Ser Asp Asp Phe Ala Tyr Gly Phe Ala Ala Thr Ala
                     35                  40                  45

Leu Ala Gly
             50
```

(2) INFORMATION FOR SEQ ID NO: 41:

(i) SEQUENCE CHARACTERISTICS:
        (A) LENGTH: 180 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..180

(xi) SEQUENCE DESCRIPTION: SEQ ID NO: 41:

```
GTC AAC CGC CCT GTC CTC GCC TGC GAC GCA AAC AAC AAC CCT CTG ACC      48
Val Asn Arg Pro Val Leu Ala Cys Asp Ala Asn Asn Asn Pro Leu Thr
             55                  60                  65

GAC GCC GGC GTC AAG TCC GGA TGT GAT GGC GGT TCT GCA TAC ACC TGT      96
Asp Ala Gly Val Lys Ser Gly Cys Asp Gly Gly Ser Ala Tyr Thr Cys
             70                  75                  80

GCC AAC AAC TCC CCA TGG GCA GTG AAC GAC CAG CTC GCC TAC GGC TTT     144
Ala Asn Asn Ser Pro Trp Ala Val Asn Asp Gln Leu Ala Tyr Gly Phe
             85                  90                  95

GCC GCC ACC AAA CTG AGC GGC GGA ACT GAG TCG TCA                     180
Ala Ala Thr Lys Leu Ser Gly Gly Thr Glu Ser Ser
100                 105                 110
```

(2) INFORMATION FOR SEQ ID NO: 42:

(i) SEQUENCE CHARACTERISTICS:
        (A) LENGTH: 60 amino acids
        (B) TYPE: amino acid
        (D) TOPOLOGY: linear (ii) MOLECULE TYPE: protein (xi) SEQUENCE DESCRIPTION: SEQ ID NO: 42:

```
Val Asn Arg Pro Val Leu Ala Cys Asp Ala Asn Asn Asn Pro Leu Thr
  1               5                  10                  15

Asp Ala Gly Val Lys Ser Gly Cys Asp Gly Gly Ser Ala Tyr Thr Cys
             20                  25                  30

Ala Asn Asn Ser Pro Trp Ala Val Asn Asp Gln Leu Ala Tyr Gly Phe
             35                  40                  45

Ala Ala Thr Lys Leu Ser Gly Gly Thr Glu Ser Ser
             50                  55                  60
```

(2) INFORMATION FOR SEQ ID NO: 43:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: cDNA

```
    (ix) FEATURE:
         (A) NAME/KEY: CDS
         (B) LOCATION: 1..63

(xi) SEQUENCE DESCRIPTION: SEQ ID NO: 43:

GGC TGC GAC GGC GGC AGC GCC TTC ACC TGC TCC AAC AAC TCT CCA TGG        48
Gly Cys Asp Gly Gly Ser Ala Phe Thr Cys Ser Asn Asn Ser Pro Trp
                    65                  70                  75

GCT GTG AAC GAA GAT                                                    63
Ala Val Asn Glu Asp
            80

(2) INFORMATION FOR SEQ ID NO: 44:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO: 44:

Gly Cys Asp Gly Gly Ser Ala Phe Thr Cys Ser Asn Asn Ser Pro Trp
 1               5                  10                  15

Ala Val Asn Glu Asp
            20

(2) INFORMATION FOR SEQ ID NO: 45:

(i) SEQUENCE CHARACTERISTICS:
        (A) LENGTH: 153 base pairs
        (B) TYPE: nucleic acid
        (C) STRANDEDNESS: single
        (D) TOPOLOGY: linear (ii) MOLECULE TYPE: cDNA (ix) FEATURE:
         (A) NAME/KEY: CDS
         (B) LOCATION: 1..153

(xi) SEQUENCE DESCRIPTION: SEQ ID NO: 45:

ACA AGA AAC GAC GGG CCC CTG TCC AGC CCC GAT GCC GCC TCC GGC TGT        48
Thr Arg Asn Asp Gly Pro Leu Ser Ser Pro Asp Ala Ala Ser Gly Cys
                    25                  30                  35

GAT GGC GGC GAA GCC TTT GCC TGT TCT AAT ACC TCG CCT TGG GCC GTC        96
Asp Gly Gly Glu Ala Phe Ala Cys Ser Asn Thr Ser Pro Trp Ala Val
            40                  45                  50

AGC GAC CAG CTC GCG TAC GGA TAC GTC GCC ACG TCC ATC TCC GGC GGC       144
Ser Asp Gln Leu Ala Tyr Gly Tyr Val Ala Thr Ser Ile Ser Gly Gly
        55                  60                  65

ACC GAG TCA                                                           153
Thr Glu Ser
 70

(2) INFORMATION FOR SEQ ID NO: 46:

(i) SEQUENCE CHARACTERISTICS:
        (A) LENGTH: 51 amino acids
        (B) TYPE: amino acid
        (D) TOPOLOGY: linear (ii) MOLECULE TYPE: protein (xi) SEQUENCE DESCRIPTION: SEQ ID NO: 46:

Thr Arg Asn Asp Gly Pro Leu Ser Ser Pro Asp Ala Ala Ser Gly Cys
 1               5                  10                  15
```

```
Asp Gly Gly Glu Ala Phe Ala Cys Ser Asn Thr Ser Pro Trp Ala Val
            20                  25                  30

Ser Asp Gln Leu Ala Tyr Gly Tyr Val Ala Thr Ser Ile Ser Gly Gly
        35                  40                  45

Thr Glu Ser
    50

(2) INFORMATION FOR SEQ ID NO: 47:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..159

(xi) SEQUENCE DESCRIPTION: SEQ ID NO: 47:

GTC CGA ACG TGT AGT GCC AAC GAC TCG CCC TTG TCC GAC CCA AAT GCC     48
Val Arg Thr Cys Ser Ala Asn Asp Ser Pro Leu Ser Asp Pro Asn Ala
            55                  60                  65

CCA AGT GGG TGT GAC GGT GGT AGC GCC TTC ACT TGT TCC AAC AAC TCC     96
Pro Ser Gly Cys Asp Gly Gly Ser Ala Phe Thr Cys Ser Asn Asn Ser
        70                  75                  80

CCG TGG GCA GTC GAT GAC CAG ACA GCT TAT GGC TTT GCG GCA ACA GCC    144
Pro Trp Ala Val Asp Asp Gln Thr Ala Tyr Gly Phe Ala Ala Thr Ala
        85                  90                  95

ATC AGT GGC CAG TCC                                                 159
Ile Ser Gly Gln Ser
100

(2) INFORMATION FOR SEQ ID NO: 48:

(i) SEQUENCE CHARACTERISTICS:
        (A) LENGTH: 53 amino acids
        (B) TYPE: amino acid
        (D) TOPOLOGY: linear (ii) MOLECULE TYPE: protein (xi) SEQUENCE DESCRIPTION: SEQ ID NO: 48:

Val Arg Thr Cys Ser Ala Asn Asp Ser Pro Leu Ser Asp Pro Asn Ala
1               5                   10                  15

Pro Ser Gly Cys Asp Gly Gly Ser Ala Phe Thr Cys Ser Asn Asn Ser
            20                  25                  30

Pro Trp Ala Val Asp Asp Gln Thr Ala Tyr Gly Phe Ala Ala Thr Ala
        35                  40                  45

Ile Ser Gly Gln Ser
    50

(2) INFORMATION FOR SEQ ID NO: 49:

(i) SEQUENCE CHARACTERISTICS:
        (A) LENGTH: 153 base pairs
        (B) TYPE: nucleic acid
        (C) STRANDEDNESS: single
        (D) TOPOLOGY: linear (ii) MOLECULE TYPE: cDNA (ix) FEATURE:
```

```
            (A) NAME/KEY: CDS
            (B) LOCATION: 1..153

(xi) SEQUENCE DESCRIPTION: SEQ ID NO: 49:

TGT GAG AAG AAC GAC AAC CCC TTA GCT GAC TTC AGC ACG AAA TCC GGG        48
Cys Glu Lys Asn Asp Asn Pro Leu Ala Asp Phe Ser Thr Lys Ser Gly
     55                  60                  65

TGT GAA AGC GGA GGT TCG GCT TAT ACG TGT AAC AAC CAA TCA CCA TGG        96
Cys Glu Ser Gly Gly Ser Ala Tyr Thr Cys Asn Asn Gln Ser Pro Trp
 70              75                  80                      85

GCC GTC AAT GAC TTG GTG TCG TAT GGC TTC GCC GCC ACA GCG ATC AAT       144
Ala Val Asn Asp Leu Val Ser Tyr Gly Phe Ala Ala Thr Ala Ile Asn
                 90                  95                 100

GGT GGC AAT                                                           153
Gly Gly Asn (2) INFORMATION FOR SEQ ID NO: 50:

(i) SEQUENCE CHARACTERISTICS:
            (A) LENGTH: 51 amino acids
            (B) TYPE: amino acid
            (D) TOPOLOGY: linear (ii) MOLECULE TYPE: protein (xi) SEQUENCE DESCRIPTION: SEQ ID NO: 50:

Cys Glu Lys Asn Asp Asn Pro Leu Ala Asp Phe Ser Thr Lys Ser Gly
 1               5                  10                  15

Cys Glu Ser Gly Gly Ser Ala Tyr Thr Cys Asn Asn Gln Ser Pro Trp
             20                  25                  30

Ala Val Asn Asp Leu Val Ser Tyr Gly Phe Ala Ala Thr Ala Ile Asn
             35                  40                  45

Gly Gly Asn
     50

(2) INFORMATION FOR SEQ ID NO: 51:

(i) SEQUENCE CHARACTERISTICS:
            (A) LENGTH: 171 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 1..171

(xi) SEQUENCE DESCRIPTION: SEQ ID NO: 51:

AGC CGC CCC GTC GGA ACC TGC AAG AGG AAC GAC AAC CCC CTC TCC GAC        48
Ser Arg Pro Val Gly Thr Cys Lys Arg Asn Asp Asn Pro Leu Ser Asp
             55                  60                  65

CCC GAT GCC AAG TCC GGC TGC GAC GGC GGC GGC GCC TTC ATG TGC TCC        96
Pro Asp Ala Lys Ser Gly Cys Asp Gly Gly Gly Ala Phe Met Cys Ser
         70                  75                  80

ACC CAG CAG CCG TGG GCC GTC AAC GAC AAT CTG GCA TAT GGC TTC GCC       144
Thr Gln Gln Pro Trp Ala Val Asn Asp Asn Leu Ala Tyr Gly Phe Ala
     85                  90                  95

GCC ACG GCC ATC AGC GGC GGC AAC GAG                                   171
Ala Thr Ala Ile Ser Gly Gly Asn Glu
100             105

(2) INFORMATION FOR SEQ ID NO: 52:
```

(i) SEQUENCE CHARACTERISTICS:
    (A) LENGTH: 57 amino acids
    (B) TYPE: amino acid
    (D) TOPOLOGY: linear (ii) MOLECULE TYPE: protein (xi) SEQUENCE DESCRIPTION: SEQ ID NO: 52:

```
Ser Arg Pro Val Gly Thr Cys Lys Arg Asn Asp Asn Pro Leu Ser Asp
 1               5                  10                  15

Pro Asp Ala Lys Ser Gly Cys Asp Gly Gly Ala Phe Met Cys Ser
             20                  25                  30

Thr Gln Gln Pro Trp Ala Val Asn Asp Asn Leu Ala Tyr Gly Phe Ala
         35                  40                  45

Ala Thr Ala Ile Ser Gly Gly Asn Glu
     50                  55
```

(2) INFORMATION FOR SEQ ID NO: 53:

(i) SEQUENCE CHARACTERISTICS:
      (A) LENGTH: 159 base pairs
      (B) TYPE: nucleic acid
      (C) STRANDEDNESS: single
      (D) TOPOLOGY: linear (ii) MOLECULE TYPE: cDNA (ix) FEATURE:
       (A) NAME/KEY: CDS
       (B) LOCATION: 1..159

(xi) SEQUENCE DESCRIPTION: SEQ ID NO: 53:

```
ACT TGC AAC AAG AAC GAC GGG CCC CTG TCC AGC CCC GAT GCC GCC TCC    48
Thr Cys Asn Lys Asn Asp Gly Pro Leu Ser Ser Pro Asp Ala Ala Ser
             60                  65                  70

GGC TGT GAT GGC GGC GAA GCC TTT GCC TGT TCT AAT ACC TCG CCT TGG    96
Gly Cys Asp Gly Gly Glu Ala Phe Ala Cys Ser Asn Thr Ser Pro Trp
     75                  80                  85

GCC GTC AGC GAC CAG CTC GCG TAC GGA TAC CTC GCC ACG TCC ATC TCC   144
Ala Val Ser Asp Gln Leu Ala Tyr Gly Tyr Leu Ala Thr Ser Ile Ser
 90                  95                 100                 105

GGC GGC ACC GAG TCG                                                159
Gly Gly Thr Glu Ser
             110
```

(2) INFORMATION FOR SEQ ID NO: 54:

(i) SEQUENCE CHARACTERISTICS:
      (A) LENGTH: 53 amino acids
      (B) TYPE: amino acid
      (D) TOPOLOGY: linear (ii) MOLECULE TYPE: protein (xi) SEQUENCE DESCRIPTION: SEQ ID NO: 54:

```
Thr Cys Asn Lys Asn Asp Gly Pro Leu Ser Ser Pro Asp Ala Ala Ser
 1               5                  10                  15

Gly Cys Asp Gly Gly Glu Ala Phe Ala Cys Ser Asn Thr Ser Pro Trp
             20                  25                  30

Ala Val Ser Asp Gln Leu Ala Tyr Gly Tyr Leu Ala Thr Ser Ile Ser
         35                  40                  45

Gly Gly Thr Glu Ser
     50
```

(2) INFORMATION FOR SEQ ID NO: 55:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..84

(xi) SEQUENCE DESCRIPTION: SEQ ID NO: 55:

```
CCA GTT TTC TCC TGT GAC AAG TAC GAC AAC CCT CTA CCT GAC GCC AAT    48
Pro Val Phe Ser Cys Asp Lys Tyr Asp Asn Pro Leu Pro Asp Ala Asn
 55                  60                  65

GCT GTG TCC GGG TGT GAC CCC GGA GGT ACT GCC TTC                    84
Ala Val Ser Gly Cys Asp Pro Gly Gly Thr Ala Phe
 70                  75                  80
```

(2) INFORMATION FOR SEQ ID NO: 56:

(i) SEQUENCE CHARACTERISTICS:
        (A) LENGTH: 28 amino acids
        (B) TYPE: amino acid
        (D) TOPOLOGY: linear (ii) MOLECULE TYPE: protein (xi) SEQUENCE DESCRIPTION: SEQ ID NO: 56:

```
Pro Val Phe Ser Cys Asp Lys Tyr Asp Asn Pro Leu Pro Asp Ala Asn
  1               5                  10                  15

Ala Val Ser Gly Cys Asp Pro Gly Gly Thr Ala Phe
                 20                  25
```

(2) INFORMATION FOR SEQ ID NO: 57:

(i) SEQUENCE CHARACTERISTICS:
        (A) LENGTH: 147 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..147

(xi) SEQUENCE DESCRIPTION: SEQ ID NO: 57:

```
ACC TGC GAC GCC TGC GAC AGC CCC CTC AGC GAC TAC GAC GCC AAG TCC    48
Thr Cys Asp Ala Cys Asp Ser Pro Leu Ser Asp Tyr Asp Ala Lys Ser
 30                  35                  40

GGC TGC GAC GGC GGT AGC GCA TAC ACC TGC ACC TAC TCT ACC CCC TGG    96
Gly Cys Asp Gly Gly Ser Ala Tyr Thr Cys Thr Tyr Ser Thr Pro Trp
 45                  50                  55                  60

GCC GTC GAC GAC AAC CTC TCC TAC GGT TTC GCC GCC GCC AAG CTG AGC   144
Ala Val Asp Asp Asn Leu Ser Tyr Gly Phe Ala Ala Ala Lys Leu Ser
                 65                  70                  75

GGA                                                               147
Gly
```

(2) INFORMATION FOR SEQ ID NO: 58:

(i) SEQUENCE CHARACTERISTICS:

(A) LENGTH: 49 amino acids
        (B) TYPE: amino acid
        (D) TOPOLOGY: linear (ii) MOLECULE TYPE: protein (xi) SEQUENCE DESCRIPTION: SEQ ID NO: 58:

Thr Cys Asp Ala Cys Asp Ser Pro Leu Ser Asp Tyr Asp Ala Lys Ser
 1               5                  10                  15

Gly Cys Asp Gly Gly Ser Ala Tyr Thr Cys Thr Tyr Ser Thr Pro Trp
                20                  25                  30

Ala Val Asp Asp Asn Leu Ser Tyr Gly Phe Ala Ala Ala Lys Leu Ser
            35                  40                  45

Gly (2) INFORMATION FOR SEQ ID NO: 59:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..135

(xi) SEQUENCE DESCRIPTION: SEQ ID NO: 59:

CCA CTA GCA GAT TTC ACC GGT GGA ACC GGC TGT AAT GGC GGT TCG ACA        48
Pro Leu Ala Asp Phe Thr Gly Gly Thr Gly Cys Asn Gly Gly Ser Thr
 50                  55                  60                  65

TTC TCA TGC TCA AAC CAA CAA CCA TGG GCG GTC AAC GAC ACA TTC TCG        96
Phe Ser Cys Ser Asn Gln Gln Pro Trp Ala Val Asn Asp Thr Phe Ser
                 70                  75                  80

TAC GGC TTT GCG GGC ATC TTT ATC ACA GGC CAT GTC GAG                   135
Tyr Gly Phe Ala Gly Ile Phe Ile Thr Gly His Val Glu
             85                  90

(2) INFORMATION FOR SEQ ID NO: 60:

(i) SEQUENCE CHARACTERISTICS:
        (A) LENGTH: 45 amino acids
        (B) TYPE: amino acid
        (D) TOPOLOGY: linear (ii) MOLECULE TYPE: protein (xi) SEQUENCE DESCRIPTION: SEQ ID NO: 60:

Pro Leu Ala Asp Phe Thr Gly Gly Thr Gly Cys Asn Gly Gly Ser Thr
 1               5                  10                  15

Phe Ser Cys Ser Asn Gln Gln Pro Trp Ala Val Asn Asp Thr Phe Ser
                20                  25                  30

Tyr Gly Phe Ala Gly Ile Phe Ile Thr Gly His Val Glu
            35                  40                  45

(2) INFORMATION FOR SEQ ID NO: 61:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (ii) MOLECULE TYPE: cDNA

```
      (ix) FEATURE:
           (A) NAME/KEY: CDS
           (B) LOCATION: 1..114

(xi) SEQUENCE DESCRIPTION: SEQ ID NO: 61:

GCC AAA TCT GGA TGT GAT GCT GGT GGA GGT CAA GCC TAC ATG TGC TCC        48
Ala Lys Ser Gly Cys Asp Ala Gly Gly Gly Gln Ala Tyr Met Cys Ser
            50                  55                  60

AAC CAA CAA CCT TGG GTA GTC AAC GAC AAC CTC GCC TAC GGT TTC GCC        96
Asn Gln Gln Pro Trp Val Val Asn Asp Asn Leu Ala Tyr Gly Phe Ala
            65                  70                  75

GCA GTC AAC ATT GCC GGC                                               114
Ala Val Asn Ile Ala Gly
        80

(2) INFORMATION FOR SEQ ID NO: 62:

(i) SEQUENCE CHARACTERISTICS:
           (A) LENGTH: 38 amino acids
           (B) TYPE: amino acid
           (D) TOPOLOGY: linear (ii) MOLECULE TYPE: protein (xi) SEQUENCE DESCRIPTION: SEQ ID NO: 62:

Ala Lys Ser Gly Cys Asp Ala Gly Gly Gly Gln Ala Tyr Met Cys Ser
 1               5                  10                  15

Asn Gln Gln Pro Trp Val Val Asn Asp Asn Leu Ala Tyr Gly Phe Ala
            20                  25                  30

Ala Val Asn Ile Ala Gly
        35

(2) INFORMATION FOR SEQ ID NO: 63:

(i) SEQUENCE CHARACTERISTICS:
           (A) LENGTH: 113 base pairs
           (B) TYPE: nucleic acid
           (C) STRANDEDNESS: single
           (D) TOPOLOGY: linear (ii) MOLECULE TYPE: cDNA (ix) FEATURE:
           (A) NAME/KEY: CDS
           (B) LOCATION: 2..112

(xi) SEQUENCE DESCRIPTION: SEQ ID NO: 63:

T TCG ACG TCC GGG TGC GAC AAT GGC GGC AGC GCC TTC ATG TGC TCT          46
  Ser Thr Ser Gly Cys Asp Asn Gly Gly Ser Ala Phe Met Cys Ser
      40                  45                  50

AAC CAA AGC CCC TGG GCC GTC AAC GAC GAT CTG GCC TAC GGC TGG GCC        94
Asn Gln Ser Pro Trp Ala Val Asn Asp Asp Leu Ala Tyr Gly Trp Ala
            55                  60                  65

GCC GTC TCA ATC GCG GGC C                                             113
Ala Val Ser Ile Ala Gly
 70              75

(2) INFORMATION FOR SEQ ID NO: 64:

(i) SEQUENCE CHARACTERISTICS:
           (A) LENGTH: 37 amino acids
           (B) TYPE: amino acid
           (D) TOPOLOGY: linear (ii) MOLECULE TYPE: protein
```

(xi) SEQUENCE DESCRIPTION: SEQ ID NO: 64:

Ser Thr Ser Gly Cys Asp Asn Gly Gly Ser Ala Phe Met Cys Ser Asn
 1               5                  10                  15

Gln Ser Pro Trp Ala Val Asn Asp Asp Leu Ala Tyr Gly Trp Ala Ala
                20                  25                  30

Val Ser Ile Ala Gly
            35

(2) INFORMATION FOR SEQ ID NO: 65:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..177

(xi) SEQUENCE DESCRIPTION: SEQ ID NO: 65:

TCA ACA CCG GTG CAG ACG TGC GAC CGC AAC GAC AAC CCG CTC TAC GAC      48
Ser Thr Pro Val Gln Thr Cys Asp Arg Asn Asp Asn Pro Leu Tyr Asp
            40                  45                  50

GGC GGG TCG ACG CGG TCC GGC TGC GAC GCC GGC GGC GGC GCC TAC ATG      96
Gly Gly Ser Thr Arg Ser Gly Cys Asp Ala Gly Gly Gly Ala Tyr Met
        55                  60                  65

TGC TCG TCG CAC AGC CCG TGG GCC GTC AGC GAC AGC CTC TCG TAC GGC     144
Cys Ser Ser His Ser Pro Trp Ala Val Ser Asp Ser Leu Ser Tyr Gly
 70              75                  80                  85

TGG GCG GCC GTC CGC ATC GCC GGC CAG TCC GAG                         177
Trp Ala Ala Val Arg Ile Ala Gly Gln Ser Glu
                90                  95

(2) INFORMATION FOR SEQ ID NO: 66:

(i) SEQUENCE CHARACTERISTICS:
        (A) LENGTH: 59 amino acids
        (B) TYPE: amino acid
        (D) TOPOLOGY: linear (ii) MOLECULE TYPE: protein (xi) SEQUENCE DESCRIPTION: SEQ ID NO: 66:

Ser Thr Pro Val Gln Thr Cys Asp Arg Asn Asp Asn Pro Leu Tyr Asp
 1               5                  10                  15

Gly Gly Ser Thr Arg Ser Gly Cys Asp Ala Gly Gly Gly Ala Tyr Met
                20                  25                  30

Cys Ser Ser His Ser Pro Trp Ala Val Ser Asp Ser Leu Ser Tyr Gly
            35                  40                  45

Trp Ala Ala Val Arg Ile Ala Gly Gln Ser Glu
        50                  55

(2) INFORMATION FOR SEQ ID NO: 67:

(i) SEQUENCE CHARACTERISTICS:
        (A) LENGTH: 150 base pairs
        (B) TYPE: nucleic acid
        (C) STRANDEDNESS: single
        (D) TOPOLOGY: linear (ii) MOLECULE TYPE: cDNA

```
    (ix) FEATURE:
         (A) NAME/KEY: CDS
         (B) LOCATION: 1..150

(xi) SEQUENCE DESCRIPTION: SEQ ID NO: 67:

AAC GAC AAC CCC ATC TCC AAC ACC AAC GCT GTC AAC GGT TGT GAG GGT    48
Asn Asp Asn Pro Ile Ser Asn Thr Asn Ala Val Asn Gly Cys Glu Gly
 60              65                  70                  75

GGT GGT TCT GCT TAC GCT TGC TCC AAC TAC TCT CCC TGG GCT GTC AAC    96
Gly Gly Ser Ala Tyr Ala Cys Ser Asn Tyr Ser Pro Trp Ala Val Asn
             80                  85                  90

GAT GAC CTT GCC TAC GGT TTC GCT GTT ACC AAG ATC TCC GGT GGC TCC   144
Asp Asp Leu Ala Tyr Gly Phe Ala Val Thr Lys Ile Ser Gly Gly Ser
         95                 100                 105

GAG GCC                                                           150
Glu Ala (2) INFORMATION FOR SEQ ID NO: 68:

(i) SEQUENCE CHARACTERISTICS:
         (A) LENGTH: 50 amino acids
         (B) TYPE: amino acid
         (D) TOPOLOGY: linear (ii) MOLECULE TYPE: protein (xi) SEQUENCE DESCRIPTION: SEQ ID NO: 68:

Asn Asp Asn Pro Ile Ser Asn Thr Asn Ala Val Asn Gly Cys Glu Gly
 1               5                  10                  15

Gly Gly Ser Ala Tyr Ala Cys Ser Asn Tyr Ser Pro Trp Ala Val Asn
             20                  25                  30

Asp Asp Leu Ala Tyr Gly Phe Ala Val Thr Lys Ile Ser Gly Gly Ser
         35                  40                  45

Glu Ala
     50

(2) INFORMATION FOR SEQ ID NO: 69:

(i) SEQUENCE CHARACTERISTICS:
         (A) LENGTH: 180 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: CDS
         (B) LOCATION: 1..180

(xi) SEQUENCE DESCRIPTION: SEQ ID NO: 69:

GTC AAT CAG CCC ATC CGA ACG TGT AGT GCC AAC GAC TCG CCC TTG TCC    48
Val Asn Gln Pro Ile Arg Thr Cys Ser Ala Asn Asp Ser Pro Leu Ser
                 55                  60                  65

GAC CCA AAT ACC CCA AGT GGC TGT GAC GGT GGT AGC GCC TTC ACT TGT    96
Asp Pro Asn Thr Pro Ser Gly Cys Asp Gly Gly Ser Ala Phe Thr Cys
             70                  75                  80

TCC AAC AAC TCC CCG TGG GCA GTC GAT GAC CAG ACA GCT TAT GGC TTT   144
Ser Asn Asn Ser Pro Trp Ala Val Asp Asp Gln Thr Ala Tyr Gly Phe
         85                  90                  95

GCG GCA ACA GCC ATC AGT GGC CAG TCC GAG AGC AGC                   180
Ala Ala Thr Ala Ile Ser Gly Gln Ser Glu Ser Ser
        100                 105                 110
```

(2) INFORMATION FOR SEQ ID NO: 70:

(i) SEQUENCE CHARACTERISTICS:
        (A) LENGTH: 60 amino acids
        (B) TYPE: amino acid
        (D) TOPOLOGY: linear (ii) MOLECULE TYPE: protein (xi) SEQUENCE DESCRIPTION: SEQ ID NO: 70:

```
Val Asn Gln Pro Ile Arg Thr Cys Ser Ala Asn Asp Ser Pro Leu Ser
 1               5                  10                  15

Asp Pro Asn Thr Pro Ser Gly Cys Asp Gly Ser Ala Phe Thr Cys
             20                  25                  30

Ser Asn Asn Ser Pro Trp Ala Val Asp Asp Gln Thr Ala Tyr Gly Phe
             35                  40                  45

Ala Ala Thr Ala Ile Ser Gly Gln Ser Glu Ser Ser
         50                  55              60
```

(2) INFORMATION FOR SEQ ID NO: 71:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..159

(xi) SEQUENCE DESCRIPTION: SEQ ID NO: 71:

```
ACC TGC GAC AAG AAG GAC AAC CCC ATC TCT GAT GCC AAC GCC AAG AGC      48
Thr Cys Asp Lys Lys Asp Asn Pro Ile Ser Asp Ala Asn Ala Lys Ser
             65                  70                  75

GGC TGT GAT GGC GGT TCT GCT TTC GCC TGC ACC AAC TAC TCT CCC TTC      96
Gly Cys Asp Gly Gly Ser Ala Phe Ala Cys Thr Asn Tyr Ser Pro Phe
             80                  85                  90

GCC GTC AAC GAC AAC CTC GCC TAC GGT TTC GCT GCC ACC AAG CTT GCT     144
Ala Val Asn Asp Asn Leu Ala Tyr Gly Phe Ala Ala Thr Lys Leu Ala
             95                 100                 105

GGA GGC TCC GAG GCT                                                  159
Gly Gly Ser Glu Ala
110
```

(2) INFORMATION FOR SEQ ID NO: 72:

(i) SEQUENCE CHARACTERISTICS:
        (A) LENGTH: 53 amino acids
        (B) TYPE: amino acid
        (D) TOPOLOGY: linear (ii) MOLECULE TYPE: protein (xi) SEQUENCE DESCRIPTION: SEQ ID NO: 72:

```
Thr Cys Asp Lys Lys Asp Asn Pro Ile Ser Asp Ala Asn Ala Lys Ser
 1               5                  10                  15

Gly Cys Asp Gly Gly Ser Ala Phe Ala Cys Thr Asn Tyr Ser Pro Phe
             20                  25                  30

Ala Val Asn Asp Asn Leu Ala Tyr Gly Phe Ala Ala Thr Lys Leu Ala
             35                  40                  45

Gly Gly Ser Glu Ala
         50
```

(2) INFORMATION FOR SEQ ID NO: 73:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..81

(xi) SEQUENCE DESCRIPTION: SEQ ID NO: 73:

```
ACC TGC TAC GCC AAT GAC CAG CGC ATC GCC GAC CGC AGC ACC AAG TCC         48
Thr Cys Tyr Ala Asn Asp Gln Arg Ile Ala Asp Arg Ser Thr Lys Ser
    55                  60                  65

GGC TGC GAC GGC GGC TCG GCC TAC TCC TGT TCT                             81
Gly Cys Asp Gly Gly Ser Ala Tyr Ser Cys Ser
 70                  75                  80
```

(2) INFORMATION FOR SEQ ID NO: 74:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO: 74:

```
Thr Cys Tyr Ala Asn Asp Gln Arg Ile Ala Asp Arg Ser Thr Lys Ser
 1               5                  10                  15

Gly Cys Asp Gly Gly Ser Ala Tyr Ser Cys Ser
            20                  25
```

(2) INFORMATION FOR SEQ ID NO: 75:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..159

(xi) SEQUENCE DESCRIPTION: SEQ ID NO: 75:

```
ACC TGT GAC AAG AAG GAC AAC CCC ATC TCA AAC TTG AAC GCT GTC AAC         48
Thr Cys Asp Lys Lys Asp Asn Pro Ile Ser Asn Leu Asn Ala Val Asn
            30                  35                  40

GGT TGT GAG GGT GGT GGT TCT GCC TTC GCC TGC ACC AAC TAC TCT CCT         96
Gly Cys Glu Gly Gly Gly Ser Ala Phe Ala Cys Thr Asn Tyr Ser Pro
        45                  50                  55

TGG GCG GTC AAT GAC AAC CTT GCC TAC GGC TTC GCT GCA ACC AAG CTT        144
Trp Ala Val Asn Asp Asn Leu Ala Tyr Gly Phe Ala Ala Thr Lys Leu
 60                  65                  70                  75

GCC GGT GGC TCC GAG G                                                  160
Ala Gly Gly Ser Glu
                80
```

(2) INFORMATION FOR SEQ ID NO: 76:

(i) SEQUENCE CHARACTERISTICS:
        (A) LENGTH: 53 amino acids
        (B) TYPE: amino acid
        (D) TOPOLOGY: linear (ii) MOLECULE TYPE: protein (xi) SEQUENCE DESCRIPTION: SEQ ID NO: 76:

Thr Cys Asp Lys Lys Asp Asn Pro Ile Ser Asn Leu Asn Ala Val Asn
 1               5                  10                  15

Gly Cys Glu Gly Gly Gly Ser Ala Phe Ala Cys Thr Asn Tyr Ser Pro
            20                  25                  30

Trp Ala Val Asn Asp Asn Leu Ala Tyr Gly Phe Ala Ala Thr Lys Leu
        35                  40                  45

Ala Gly Gly Ser Glu
    50

(2) INFORMATION FOR SEQ ID NO: 77:

(i) SEQUENCE CHARACTERISTICS:
        (A) LENGTH: 165 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..165

(xi) SEQUENCE DESCRIPTION: SEQ ID NO: 77:

CCA GTA GGC ACC TGC GAC GCC GGC AAC AGC CCC CTC GGC GAC CCC CTG      48
Pro Val Gly Thr Cys Asp Ala Gly Asn Ser Pro Leu Gly Asp Pro Leu
 55                  60                  65

GCC AAG TCT GGC TGC GAG GGC GGC CCG TCG TAC ACG TGC GCC AAC TAC      96
Ala Lys Ser Gly Cys Glu Gly Gly Pro Ser Tyr Thr Cys Ala Asn Tyr
        70                  75                  80              85

CAG CCG TGG GCG GTC AAC GAC CAG CTG GCC TAC GGC TTC GCG GCC ACG     144
Gln Pro Trp Ala Val Asn Asp Gln Leu Ala Tyr Gly Phe Ala Ala Thr
                90                  95                 100

GCC ATC AAC GGC GGC ACC GAG                                         165
Ala Ile Asn Gly Gly Thr Glu
            105

(2) INFORMATION FOR SEQ ID NO: 78:

(i) SEQUENCE CHARACTERISTICS:
        (A) LENGTH: 55 amino acids
        (B) TYPE: amino acid
        (D) TOPOLOGY: linear (ii) MOLECULE TYPE: protein (xi) SEQUENCE DESCRIPTION: SEQ ID NO: 78:

Pro Val Gly Thr Cys Asp Ala Gly Asn Ser Pro Leu Gly Asp Pro Leu
 1               5                  10                  15

Ala Lys Ser Gly Cys Glu Gly Gly Pro Ser Tyr Thr Cys Ala Asn Tyr
            20                  25                  30

Gln Pro Trp Ala Val Asn Asp Gln Leu Ala Tyr Gly Phe Ala Ala Thr
        35                  40                  45

Ala Ile Asn Gly Gly Thr Glu
    50                  55

```
(2) INFORMATION FOR SEQ ID NO: 79:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 79:

Thr Arg Xaa Xaa Asp Cys Cys Xaa Xaa Xaa Cys Xaa Trp Xaa
1               5                   10

(2) INFORMATION FOR SEQ ID NO: 80:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 80:

Trp Cys Cys Xaa Cys
1               5

(2) INFORMATION FOR SEQ ID NO: 81:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 81:

Trp Cys Cys Xaa Cys Tyr
1               5

(2) INFORMATION FOR SEQ ID NO: 82:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 82:

Xaa Pro Gly Gly Gly Xaa Gly Xaa Phe
1               5

(2) INFORMATION FOR SEQ ID NO: 83:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 83:

Gly Cys Xaa Xaa Arg Xaa Asp Trp Xaa
1               5
```

(2) INFORMATION FOR SEQ ID NO: 84:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 84:

CCCCAAGCTT ACNMGNTAYT GGGAYTGYTG YAARMC                              36

(2) INFORMATION FOR SEQ ID NO: 85:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 85:

CTAGTCTAGA TARCANGCRC ARCACC                                        26

(2) INFORMATION FOR SEQ ID NO: 86:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 86:

CTAGTCTAGA AANADNCCNA VNCCNCCNCC NGG                                 33

(2) INFORMATION FOR SEQ ID NO: 87:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 87:

CTAGTCTAGA NAACCARTCA RWANCKCC                                      28

(2) INFORMATION FOR SEQ ID NO: 88:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 88:

CGGAGCTCAC GTCCAAGAGC GGCTGCTCCC GTCCCTCCAG CAGCACCAGC TCTCCGG       57

(2) INFORMATION FOR SEQ ID NO: 89:

(i) SEQUENCE CHARACTERISTICS:
          (A) LENGTH: 57 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 89:

CCGGAGAGCT GGTGCTGCTG GAGGGACGGG AGCAGCCGCT CTTGGACGTG AGCTCCG          57

(2) INFORMATION FOR SEQ ID NO: 90:

(i) SEQUENCE CHARACTERISTICS:
          (A) LENGTH: 57 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 90:

CGGAGCTCAC GTCCAAGAGC GGCTGCTCCC GTAACGACGA CGGCAACTTC CCTGCCG          57

(2) INFORMATION FOR SEQ ID NO: 91:

(i) SEQUENCE CHARACTERISTICS:
          (A) LENGTH: 57 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 91:

CGGCAGGGAA GTTGCCGTCG TCGTTACGGG AGCAGCCGCT CTTGGACGTG AGCTCCG          57

(2) INFORMATION FOR SEQ ID NO: 92:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 92:

CAACATCACA TCAAGCTCTC C                                                 21

(2) INFORMATION FOR SEQ ID NO: 93:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 93:

CCCCATCCTT TAACTATAGC G                                                 21

(2) INFORMATION FOR SEQ ID NO: 94:

(i) SEQUENCE CHARACTERISTICS:
          (A) LENGTH: 53 base pairs
          (B) TYPE: nucleic acid
          (C) STRANDEDNESS: single (D) TOPOLOGY: linear (ii) MOLECULE TYPE: cDNA (xi) SEQUENCE DESCRIPTION: SEQ ID NO: 94:

GGTCGCCCGG ACTGGCTGTT CCCGTACCCC CTCCAGCAGC ACCAGCTCTC CGG          53

(2) INFORMATION FOR SEQ ID NO: 95:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 95:

CCGGAGAGCT GGTGCTGCTG GAGGGGTAC GGGAACAGCC AGTCCGGGCG ACC           53

(2) INFORMATION FOR SEQ ID NO: 96:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 96:

CGGACTACTA GCAGCTGTAA TACG                                         24

(2) INFORMATION FOR SEQ ID NO: 97:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 97:

GACCGGAGAG CTGGTGCTGC TGGAGGGTTT ACGAACACAG CCCGAGATAT TAGTG       55

(2) INFORMATION FOR SEQ ID NO: 98:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 98:

CCCCAAGCTT GACTTGGAAC CAATGGTCCA TCC                               33

(2) INFORMATION FOR SEQ ID NO: 99:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 99:

CCCCAAGCTT CCATCCAAAC ATGCTTAAAA CGCTCG                                    36

(2) INFORMATION FOR SEQ ID NO: 100:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 100:

CACTAATATC TCGGGCTGTG TTCGTAAACC CTCCAGCAGC ACCAGCTCTC CGGTC              55

(2) INFORMATION FOR SEQ ID NO: 101:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 101:

GGGCGTGAAT GTAAGCGTGA CATA                                                24

(2) INFORMATION FOR SEQ ID NO: 102:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 102:

Thr Arg Tyr Trp Asp Cys Cys Lys Pro Ser Cys Ala Trp
1               5                   10

(2) INFORMATION FOR SEQ ID NO: 103:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 103:

Thr Arg Tyr Trp Asp Cys Cys Lys Thr Ser Cys Ala Trp
1               5                   10

(2) INFORMATION FOR SEQ ID NO: 104:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 104:

```
Thr Arg Tyr Trp Asp Cys Cys Lys Pro Ser Cys Gly Trp
1               5                   10
```

(2) INFORMATION FOR SEQ ID NO: 105:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 105:

```
Xaa Thr Arg Xaa Phe Asp Xaa
1               5
```

(2) INFORMATION FOR SEQ ID NO: 106:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 106:

```
Xaa Thr Arg Xaa Tyr Asp Xaa
1               5
```

(2) INFORMATION FOR SEQ ID NO: 107:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 107:

```
Xaa Thr Arg Xaa Trp Asp Xaa
1               5
```

(2) INFORMATION FOR SEQ ID NO: 108:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 108:

```
Thr Arg Xaa Xaa Asp Cys Cys Xaa Xaa Xaa Cys Xaa Trp
1               5                   10
```

(2) INFORMATION FOR SEQ ID NO: 109:

(i) SEQUENCE CHARACTERISTICS:
        (A) LENGTH: 5 amino acids
        (B) TYPE: amino acid
        (C) STRANDEDNESS: single
        (D) TOPOLOGY: linear -continued (ii) MOLECULE TYPE: peptide (xi) SEQUENCE DESCRIPTION: SEQ ID NO: 109:

Trp Cys Cys Xaa Cys
 1               5

ENDOGLUCANASES

This application is a divisional of application Ser. No. 08/651,136 filed on May 21, 1996 now U.S. Pat. No. 6,001,639 and claims priority under 35 U.S.C. 119 of Danish application Ser. Nos. 0272/95 filed Mar. 17, 1995, 0888/95 filed Aug. 8, 1995, 0887/95 filed Aug. 8, 1995, 0886/95 filed Aug. 8, 1995, 0885/95 filed Aug. 8, 1995 and 0137/96 filed Feb. 12, 1996, the contents of which are fully incorporated herein by reference.

FIELD OF THE INVENTION

The present invention relates to novel enzyme preparations comprising an enzyme exhibiting endoglucanase activity which performs very good in industrial applications such as laundry compositions, for biopolishing of newly manufactured textiles, for providing an abraded look of cellulosic fabric or garment, and for treatment of paper pulp. Further, the invention relates to DNA constructs encoding such enzymes, a method for providing a gene encoding for such enzymes, a method of producing the enzymes, enzyme preparations containing such enzymes, and the use of these enzymes for a number of industrial applications.

BACKGROUND OF THE INVENTION

Cellulases or cellulloytic enzymes are enzymes involved in hydrolyses of cellulose. In the hydrolysis of native cellulose, it is known that there are three major types of cellulase enzymes involved, namely cellobiohydrolase (1,4-β-D-glucan cellobiohydrolase, EC 3.2.1.91), endo-β-1,4-glucanase (endo-1,4-β-D-glucan 4-glucanohydrolase, EC 3.2.1.4) and β-glucosidase (EC 3.2.1.21).

Cellulases are synthesized by a large number of microorganisms which include fungi, actinomycetes, myxobacteria and true bacteria but also by plants. Especially endoglucanases of a wide variety of specificities have been identified.

A very important industrial use of cellulytic enzymes is the use for treatment of cellulosic textile or fabric, e.g. as ingredients in detergent compositions or fabric softener compositions, for bio-polishing of new fabric (garment finishing), and for obtaining a "stone-washed" look of cellulose-containing fabric, especially denim, and several methods for such treatment have been suggested, e.g. in GB-A-1 368 599, EP-A-0 307 564 and EP-A-0 435 876, WO 91/17243, WO 91/10732, WO 91/17244, PCT/DK95/000108 and PCT/DK95/00132.

Another important industrial use of cellulytic enzymes is the use for treatment of paper pulp, e.g. for improving the drainage or for deinking of recycled paper.

Especially the endoglucanases (EC No. 3.2.1.4) constitute an interesting group of hydrolases for the mentioned industrial uses. Endoglucanases catalyses endo hydrolysis of 1,4-β-D-glycosidic linkages in cellulose, cellulose derivatives (such as carboxy methyl cellulose and hydroxy ethyl cellulose), lichenin, β-1,4 bonds in mixed β-1,3 glucans such as cereal β-D-glucans or xyloglucans and other plant material containing cellulosic parts. The authorized name is endo-1,4-β-D-glucan 4-glucano hydrolase, but the abbreviated term endoglucanase is used in the present specification. Reference can be made to T.-M. Enveri, "Microbial Cellulases" in W. M. Fogarty, Microbial Enzymes and Biotechnology, Applied Science Publishers, p. 183–224 (1983); Methods in Enzymology, (1988) Vol. 160, p. 200–391 (edited by Wood, W. A. and Kellogg, S. T.); Béguin, P., "Molecular Biology of Cellulose Degradation", Annu. Rev. Microbiol. (1990), Vol. 44, pp. 219–248; Béguin, P. and Aubert, J-P., "The biological degradation of cellulose", FEMS Microbiology Reviews 13 (1994) p.25–58; Henrissat, B., "Cellulases and their interaction with cellulose", Cellulose (1994), Vol. 1, pp. 169–196.

Fungal endoglucanases have been described in numerous publications, especially those derived from species as e.g. *Fusarium oxysporum, Trichoderma reesei, Trichoderma longibrachiatum, Aspergillus aculeatus, Neocallimastix patriciarum*, and e.g. from species of the genera Piromyces, Humicola, Myceliophthora, Geotricum, Penicillium, Irpex, Coprinus.

For example, fungal endoglucanases have been described by Sheppard, P. O., et al., "The use of conserved cellulase family-specific sequences to clone Cellulase homologue cDNAs from *Fusarium oxysporum*, Gene, (1994), Vol. 15, pp. 163–167, Saloheimo, A., et al., "A novel, small endoglucanase gene, egI5, from *Trichoderma reesei* isolated by expression in yeast", Molecular Microbiology (1994), Vol. 13(2), pp. 219–228; van Arsdell, J. N. et al., (1987), Cloning, characterization, and expression in *Saccharomyces cerevisiae* of endoglucanase I from *Trichoderma reesei*, Bio/Technology 5: 60–64; Penttilä, M. et al., (1986), "Homology between cellulase genes of *Trichoderma reesei*: complete nucleotide sequence of the endoglucanase I gene", Gene 45:253–263; Saloheimo, M. et al, (1988), "EGIII, a new endoglucanase from *Trichoderma reesei*: the characterization of both gene and enzyme", Gene 63:11–21; Gonzáles, R., et al., "Cloning, sequence analysis and yeast expression of the egl1 gene from *Trichoderma longibrachiatum*", Appl. Microbiol. Biotechnol., (1992), Vol. 38, pp. 370–375; Ooi, T. et al. "Cloning and sequence analysis of a cDNA for cellulase (FI-CMCase) from *Aspergillus aculeatus*", Curr. Genet., (1990), Vol. 18, pp. 217–222; Ooi, T. et al, "Complete nucleotide sequence of a gene coding for *Aspergillus aculeatus* cellulase (FI-CMCase)", Nucleic Acids Research, (1990), Vol. 18, No. 19, p. 5884; Xue, G. et al., "Cloning and expression of multiple cellulase cDNAs from the anaerobic rumen fungus *Neocallimastix patriciarum* in *E. coli*", J. Gen. Microbiol., (1992), Vol. 138, pp. 1413–1420; Xue, G. et al., "A novel polysaccharide hydrolase cDNA (celD) from *Neocallimastix patriciarum* encoding three multi-functional catalytical domains with high endoglucanase, cellobiohydrolase and xylanase activities", J. Gen. Microbiol., (1992), Vol. 138, pp. 2397–2403; Zhou, L. et al., "Intronless celB from the anaerobic fungus *Neocallimastix patriciarum* encodes a modular family A endoglucanase", Biochem. J., (1994), Vol. 297, pp. 359–364; Dalbøge, H. and Heldt-Hansen, H. P., "A novel method for efficient expression cloning of fungal enzyme genes", Mol. Gen. Genet., (1994), Vol. 243, pp. 253–260; Ali, B. R. S. et al., "Cellulases and hemicellulases of the anaerobic fungus *Piromyces constitute* a multiprotein cellulose-binding complex and are encoded by multigene families", FEMS Microbiol. Lett., (1995), Vol. 125, No. 1, pp. 15–21. Further, the DNA Data Bank of Japan (DDBJ database publicly available at Internet) comprises two DNA sequences cloned from *Penicillium janthinellum* encoding endoglucanases (cloned by A. Koch and G. Mernitz, respectively) and a DNA sequence cloned from *Humicola grisea* var. thermoidea encoding an endoglucanase (cloned by T. Uozumi). Two endoglucanases from *Macrophomina phaseolina* have been cloned and sequenced, see Wang, H. Y. and Jones, R. W.: "Cloning, characterization and functional expression of an endoglucanase-encoding gene from the phytopathogenic fungus *Macrophomina phaseolina*" in Gene, 158:125–128, 1995, and Wang, H. Y. and Jones, R. W.: "A unique endoglucanase-encoding gene cloned from the phytopathogenic fungus *Macrophomina phaseolina*" in Applied And Environmental Microbiology, 61:2004–2006, 1995. One of these endoglucanases shows high homology to the egl3 endoglucanase from the fungus *Trichoderma reesei*, the other shows homology to the egl1 from the microbial phytopathogen *Pseudomonas solanacearum* indicating that both endoglucanases belong to family 5 of glycosyl hydrolases (B. Henrissat, Biochem J 280:309–316 (1991)). Filament-specific expression of a cellulase gene in the dimorphic fungus *Ustilago maydis* is disclosed in Schauwecker, F. et al. (1995).

WO 91/17243 (Novo Nordisk A/S) discloses a cellulase preparation consisting of a homogenous endoglucanase component immunoreactive with an antibody raised against a highly purified 43 kDa endoglucanase derived from *Humicola insolens*, DSM 1800; WO 91/17244 (Novo Nordisk A/S) discloses a new (hemi)cellulose degrading enzyme, such as an endoglucanase, a cellobiohydrolase or a β-glucosidase, which may be derived from fungi other than Trichoderma and Phanerochaete; WO 93/20193 discloses an endoglucanase derivable from *Aspergillus aculeatus*; WO 94/21801 (Genencor Inc.) concerns a cellulase system isolated from *Trichoderma longibrachiatum* exhibiting endoglucanase activity; WO 94/26880 (Gist Brocades N.V.) discloses an isolated mixture of cellulose degrading enzymes, which preferable are obtained from Trichoderma, Aspergillus or Disporotrichum, comprising endoglucanase, cellobiohydrolase, and xyloglucanase activity; and WO 95/02043 (Novo Nordisk A/S) describes an enzyme with endoglucanase activity derived from *Trichoderma harzianum*, which can be used for a number of purposes including e.g. degradation or modification of plant cell walls.

It is also known that cellulases may or may not have a cellulose binding domain (a CBD). The CBD enhances the binding of the enzyme to a cellulose-containing fiber and increases the efficacy of the catalytic active part of the enzyme.

There is an ever existing need for providing novel cellulase enzyme preparations which may be used for applications where cellulase, preferably an endoglucanase, activity is desirable.

The object of the present invention is to provide novel enzyme preparations having substantial cellulytic activity at acid, neutral or alkaline conditions and improved performance in paper pulp processing, textile treatment, laundry processes or in animal feed; preferably novel cellulases, more preferably well-performing endoglucanases, which are contemplated to be producible or produced by recombinant techniques.

SUMMARY OF THE INVENTION

Surprisingly, it has been found that a group of endoglucanases having certain unique characteristics perform very good in those industrial applications for which endoglucanases are conventionally used. These unique characteristics can be described in terms of conserved regions of the amino acid sequence of the enzyme protein and the inventors have found that cellulytic enzymes, i.e. enzymes exhibiting cellulytic activity, having certain conserved regions are very effective e.g. in the treatment of laundry, in the treatment of newly manufactured textile, in the treatment of papermaking pulp.

Accordingly, in its first aspect the present invention relates to an enzyme preparation consisting essentially of an enzyme having cellulytic activity and comprising a first amino acid sequence consisting of 14 amino acid residues having the following sequence

```
                                         (SEQ ID NO:79)
Arg Xaa Xaa Asp Cys Cys Xaa Xaa Xaa Cys Xaa
 1   2   3   4   5   6   7   8   9  10  11  12
Trp Xaa
13  14
``` and a second amino acid sequence consisting of 5 amino acid residues having the following sequence

```
      Trp Cys Cys Xaa Cys   (SEQ ID NO:80)
       1   2   3   4   5
``` wherein,
in position 3 of the first sequence, the amino acid is Trp, Tyr or Phe;
in position 4 of the first sequence, the amino acid is Trp, Tyr or Phe;
in position 8 of the first sequence, the amino acid is Arg, Lys or His;
in position 9, 10, 12 and 14, respectively, of the first sequence, and in position 4 of the second sequence, the amino acid is any of the 20 naturally occurring amino acid residues with the provisos that, in the first amino acid sequence, (i) when the amino residue in position 12 is Ser, then the amino acid residue in position 14 is not Ser, and (ii) when the amino acid residue in position 12 is Gly, then the amino acid residue in position 14 is not Ala.

This surprising finding of clearly recognisable conserved regions, in spite of rather prominent variations found within well-performing endoglucanase enzymes, is a result of studies of a number of fungal DNA sequences encoding for specific amino acid sequences of enzymes having significant cellulytic, especially endoglucanase, activities.

Based on this finding, a novel molecular method taylored to screen specifically for genomic DNA or cDNA characterised by encoding the enzymes of the invention has been developed. As tools for this three sets of degenerated primers were constructed. Accordingly, in its second aspect, the invention relates to a method for providing a gene encoding for cellulytic enzymes having the above conserved regions.

By using this method, i.e. the set of primers for a PCR screening on genomic DNA, it was surprisingly found that DNA encoding for said enzymes can be found from a broad range of fungi, belonging to taxonomically very different organisms and inhabiting ecologically very different niches.

Further, by using this method it has been possible to find DNA sequences encoding for the core regions (catalytically active regions or domains) of said enzymes without any attached cellulose binding domain (CBD) which core regions of enzymes would not have been selected by using conventional performance based screening approaches. The inventors have verified experimentally that the linking of a CBD region to a core region enzyme (comprising the catalytically active region or domain of the enzyme) of the present invention results in a significantly improved performance, e.g. a fifty times higher performance, of the multiple domain enzyme.

Accordingly, the present invention provides novel cellulases, especially endoglucanases, having improved performance in industial applications, either in their native form, or homo- or heterologously produced.

In further aspects, the present invention relates to novel cellulytic enzyme preparations which are derivable from taxonomically specific phyli, classes, orders, families, genera, and species; e.g. from Basidiomycotous Hymenomycetes, Zygomycota, Chytridiomycota; or from the classes Discomycetes, Loculoascomycetes, Plectomycetes; Archaeascomycetes, Hemiascomycetes or from the orders Diaportales, Xylariales, Trichosphaeriales, Phyllachorales; or from the families Nectriaeae, Sordariaceae, Chaetomiaceae, Ceratostomaceae, Lasiosphaeriaceae; or from the genera Cylindrocarpon, Gliocladium, Volutella, Scytalidium, Acremonium, or from the species *Fusarium lycopersici, Fusarium passiflora, Fusarium solani, Fusarium anguioides, Fusarium poae, Humicola nigrescens, Humicola grisea*, especially such consisting essentially of an enzyme comprising an amino acid sequence selected from the group consisting of the sequences (SEQ ID NOS:105–107)

```
Xaa Thr Arg Xaa Phe Asp Xaa
 1   2   3   4   5   6   7;

Xaa Thr Arg Xaa Tyr Asp Xaa
 1   2   3   4   5   6   7; and

Xaa Thr Arg Xaa Trp Asp Xaa
 1   2   3   4   5   6   7
``` wherein, in position 4, Xaa is Trp, Tyr or Phe; and in position 1 and 7, Xaa is any of the 20 naturally occurring amino acid residues.

More specifically, the enzyme preparation of the invention is preferably obtainable from the taxonomically specific phyli, classes, orders, families, genera, and species mentioned above which all produce endoglucanases comprising a first peptide consisting of 13 amino acid residues having the following sequence (SEQ ID NO:108)

```
Thr Arg Xaa Xaa Asp Cys Cys Xaa Xaa Xaa Cys Xaa
 1   2   3   4   5   6   7   8   9  10  11  12

Trp
13
``` and a second peptide consisting of 5 amino acid residues having the following sequence (SEQ ID NO:80)

```
Trp Cys Cys Xaa Cys
 1   2   3   4   5
``` wherein, in position 3 of the first sequence, the amino acid is Trp, Tyr or Phe; in position 4 of the first sequence, the amino acid is Trp, Tyr or Phe; in position 8 of the first sequence, the amino acid is Arg, Lys or His; in position 9, 10, and 12, respectively, of the first sequence, and in position 4 of the second sequence, the amino acid is any of the 20 naturally occurring amino acid residues.

In yet further aspects, the present invention provides DNA constructs comprising a DNA sequence encoding an enzyme exhibiting endoglucanase activity, which DNA sequence comprises the DNA sequence shown in SEQ ID No. 1, 7, 9, 11, 13, 15, 21, and 25, respectively, or analogues thereof.

The present invention also relates to a recombinant expression vector comprising a DNA construct of the invention; to a cell comprising a DNA construct or a recombinant expression vector of the invention; to a method of producing an enzyme, e.g. a recombinant enzyme, of the invention; to a method of providing colour clarification of laundry by using the enzyme of the invention; to a laundry composition comprising the enzyme of the invention; to uses of the enzyme of the invention for degradation or modification of plant material, e.g. cell walls, for treatment of fabric, textile or garment, for treatment of paper pulp; and to an enzyme preparation which is enriched in an enzyme of the present invention.

THE DRAWINGS

Figure 1A:
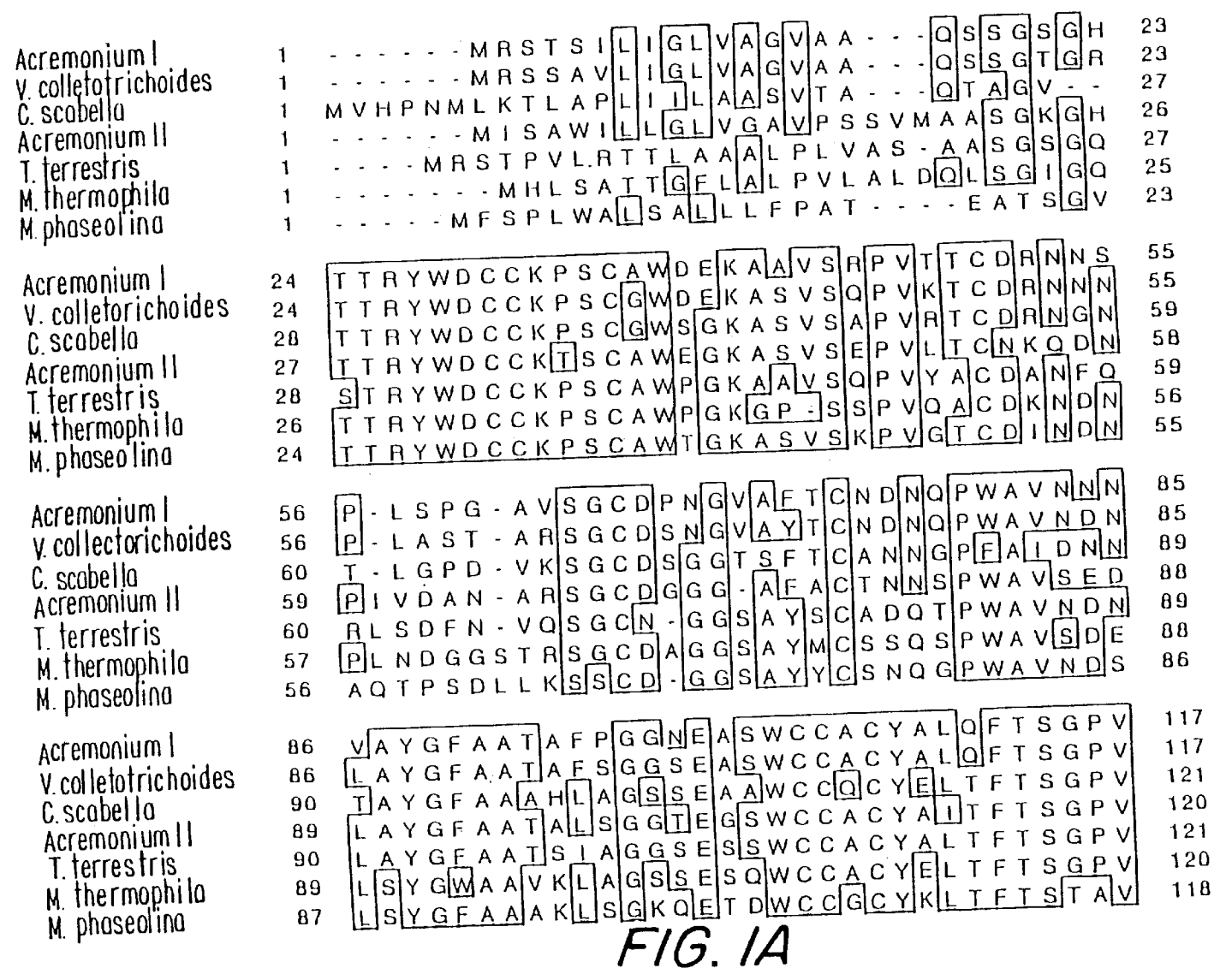
Figure 1B:
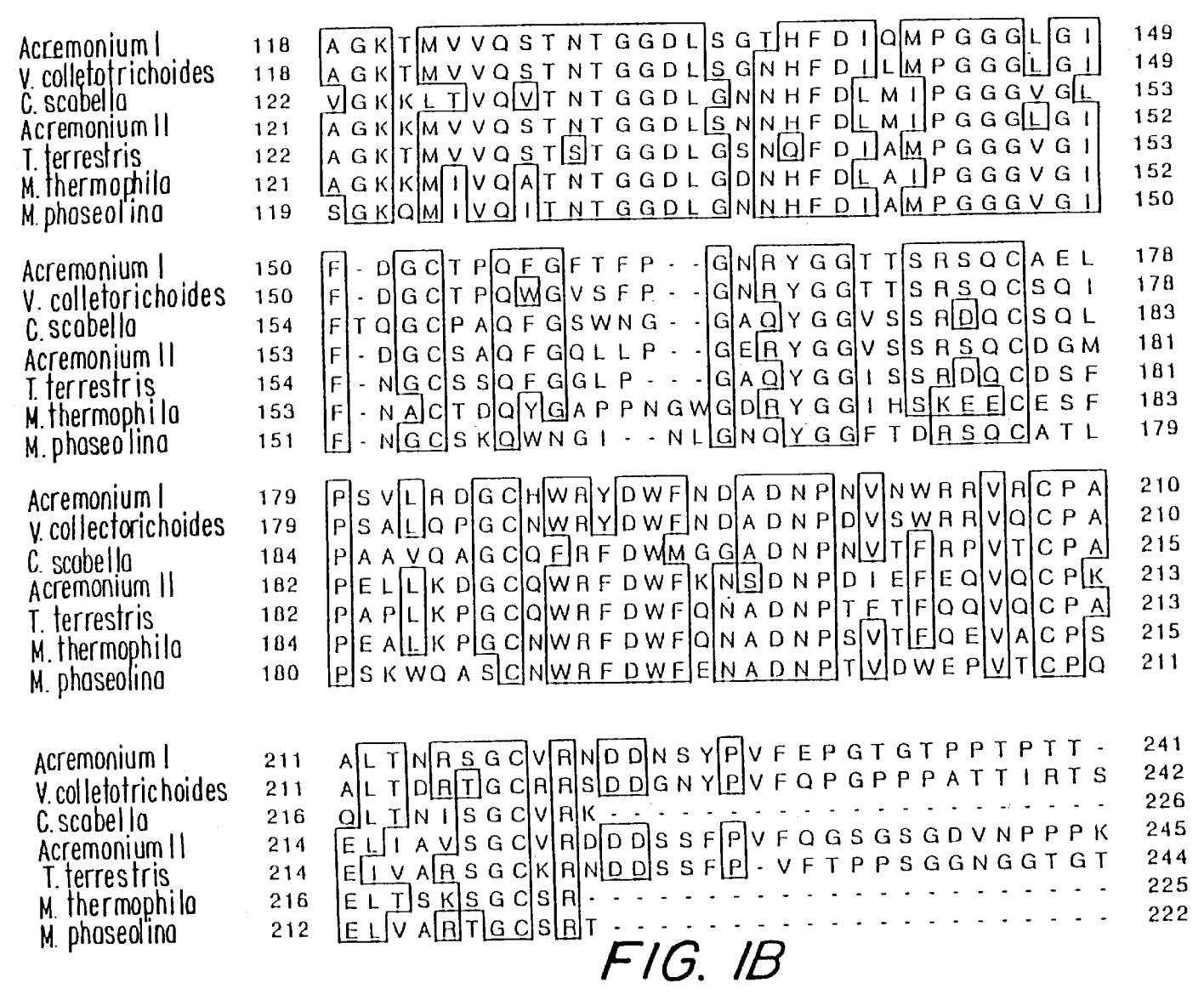

FIGS. 1(A, B, C) is an alignment of the deduced encoded amino acid sequences of Acremonium sp. (I), *Volutella colletotrichoides, Crinipellis scabella*, Acremonium sp. (II), *Myceliophthora thermophila, Thielavia terrestris, Macrophomina phaseolina*. The Pileup program (Feng and Doolittle, 1987) (GCG package, version 8.0) was used to create the best alignment. Identical residues in at least four sequences (boxed) are indicated around the corresponding amino acids.

Figure 2B:
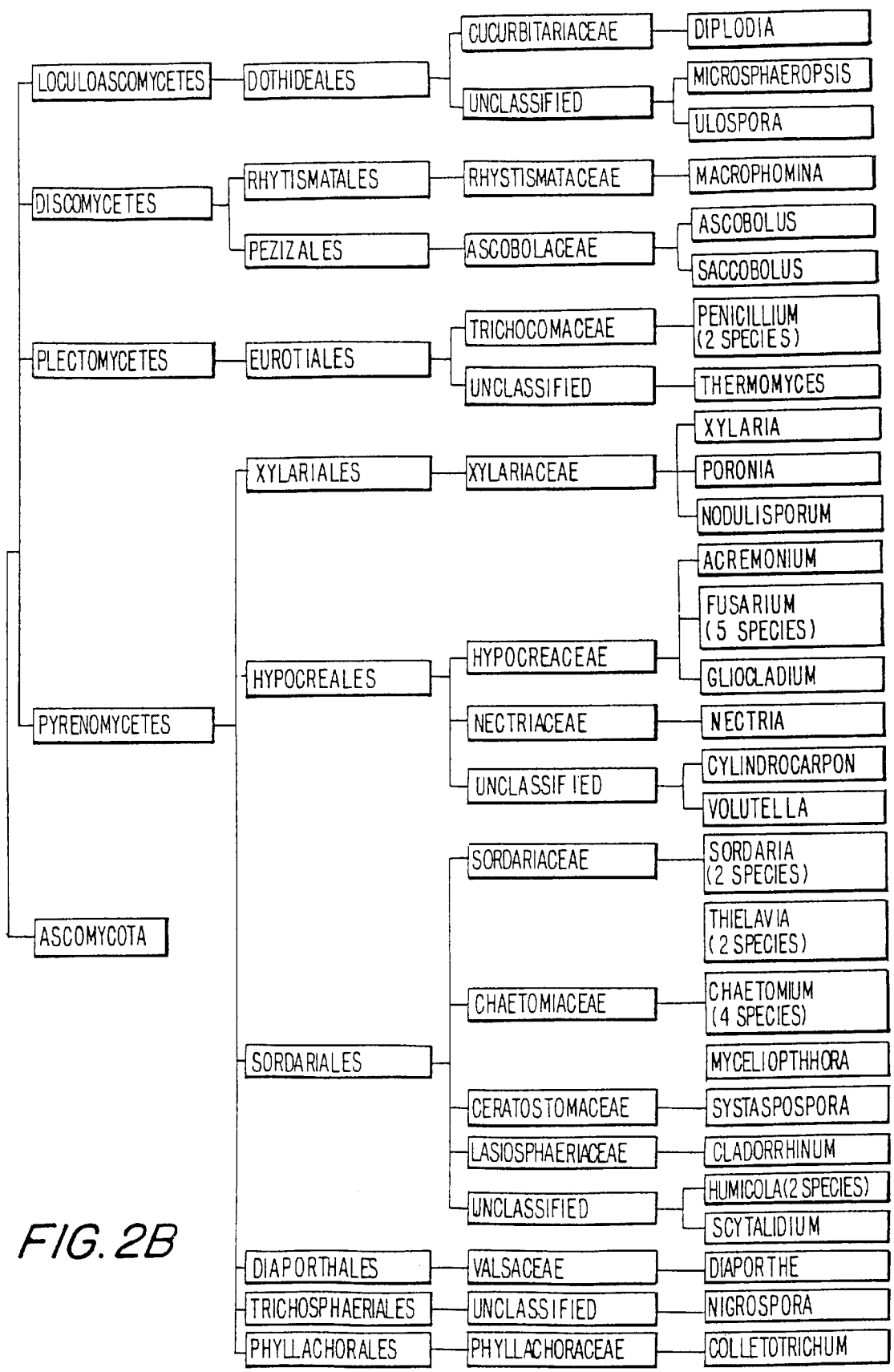
Figure 2C:
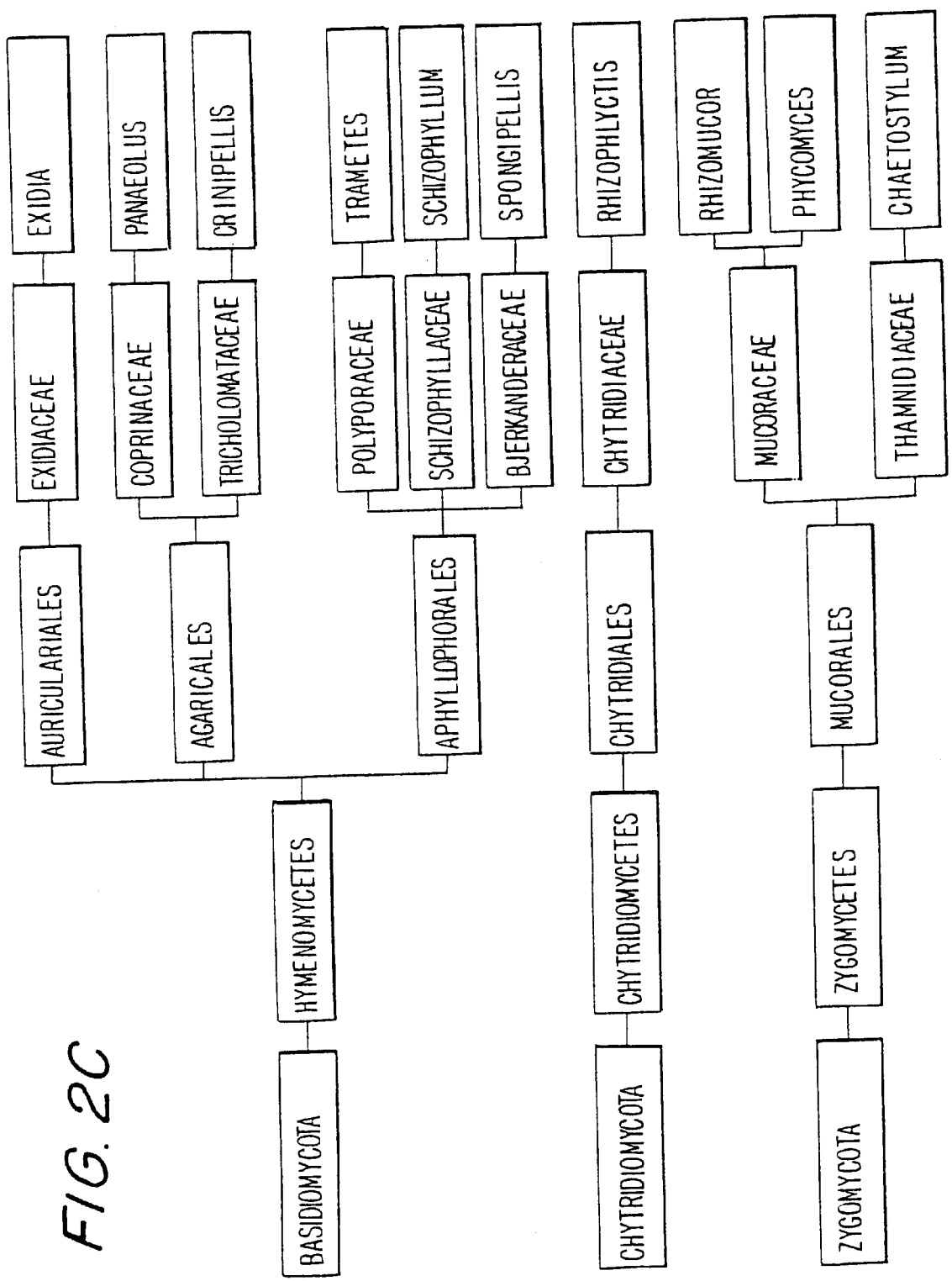

FIGS. 2(*a, b, c*) illustrates the taxonomic classification within the Fungal Kingdom of all the microorganisms disclosed herein as being capable of producing said enzyme preparations and enzymes of the invention.

The taxonomic classification used herein builds primarily on the system used in the :NIH Data Base (Entrez, version spring 1996) available on World Wide Web: (http://www3.ncbi.nlm.nih.gov/htbin/ef/entrezTAX).

Regarding classification of organisms which are not included in the Entrez data base the following generally available and world wide accepted reference books have been used:

For Ascomycetes: Eriksson, O. E. & Hawksworth, D. L.: Systema Ascomycetum vol 12 (1993).

For Basidiomycetes: Jülich, W.: Higher Taxa of Basidiomycetes, Bibliotheca Mycologia 85, 485pp (1981).

For Zygomycetes. O'Donnell, K.: Zygomycetes in culture, University of Georgia, US, 257pp (1979).

General mycological reference books: Hawksworth, D. L., Kirk, P. M., Sutton, B. C. and Pegler, D. N.: Dictionary of the fungi, International Mycological Institute, 616pp (1995); Von Arx, J. A.: The genera of fungi sporulating in culture, 424pp (1981).

The taxonomic implacement of the genus Humicola has untill recently remained unclear. However, studies of 18SRNA of a wide selection of Sordariales has given strong indications of referring Humicola to the order Sordariales (Taylor, Clausen & Oxenbøll, unpublished). Further these data suggests Humicola along with Scytalidium to be only rather distantly related to the families Sordariaceae, Chaetomiaceae, Ceratostomataceae, and Lasiosphaeriaceae. In accordance with the above Humicola and Scytalidium are here placed within the order Sordariales, with unclassified Family.

Figure 3A:
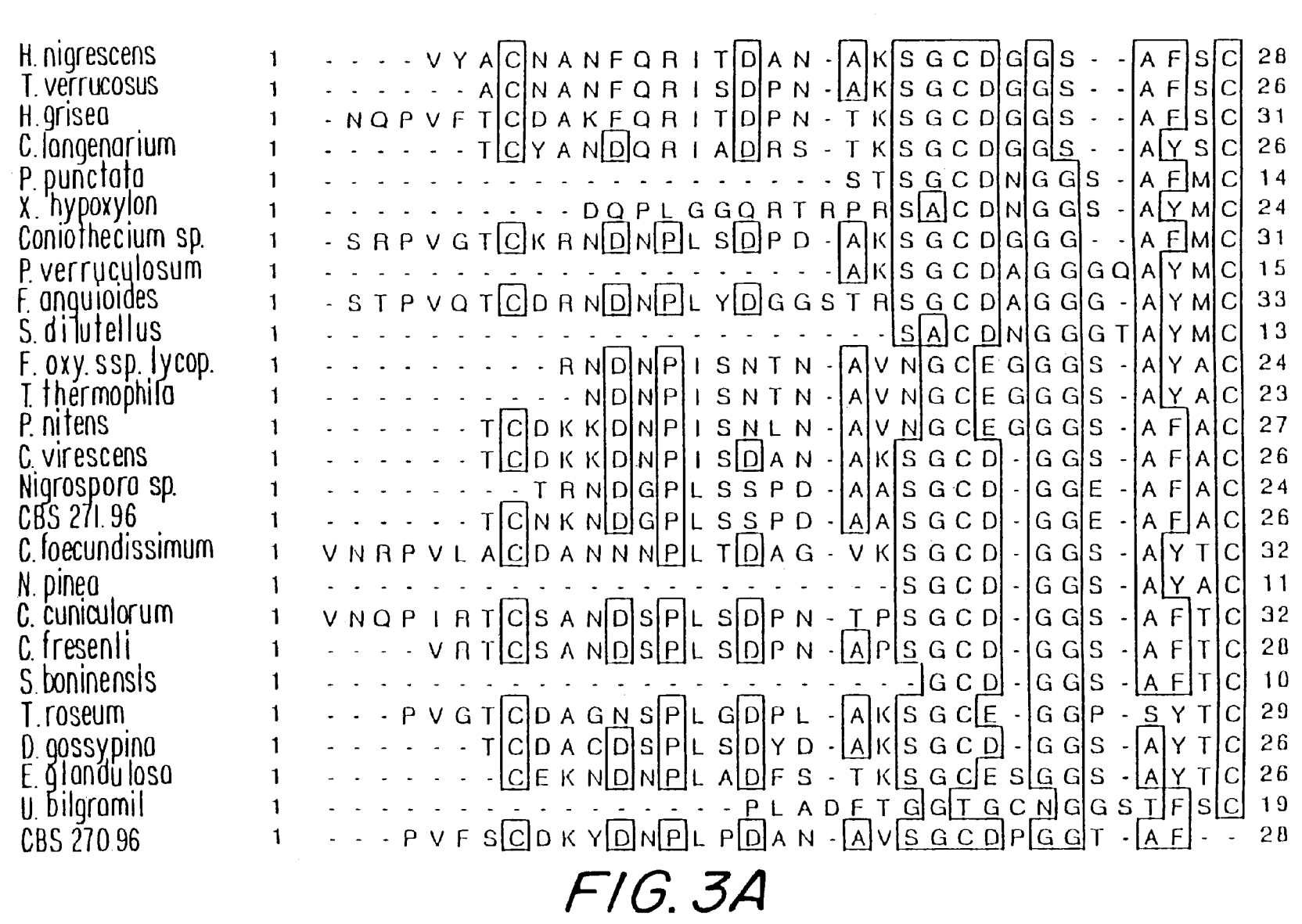

FIGS. 3(A, B) is an alignment of the deduced partial amino acid sequences derived from a selection of 26 of the 46 microorganisms described in Example 5.

DETAILED DESCRIPTION OF THE INVENTION

In the present context, the term "the 20 naturally occuring amino acid residues" denotes the 20 amino acid residues usually found in proteins and conventionally known as alanine (Ala or A), valine (Val or V), leucine (Leu or L), isoleucine (Ile or I), proline (Pro or P), phenylalanine (Phe or F), tryptophan (Trp or W), methionine (Met or M), glycine (Gly or G), serine (Ser or S), threonine (Thr or T), cysteine (Cys or C), tyrosine (Tyr or Y), asparagine (Asn or N), glutamine (Gln or Q), aspartic acid (Asp or D), glutamic acid (Glu or E), lysine (Lys or K), arginine (Arg or R), and histidine (His or H).

According to the present invention there is provided novel well-performing endoglucanases comprising conserved amino acid sequence regions, especially a first amino acid sequence consisting of 14 amino acid residues having the following sequence

```
                                            (SEQ ID NO:79)
Thr Arg Xaa Xaa Asp Cys Cys Xaa Xaa Xaa Cys Xaa
 1   2   3   4   5   6   7   8   9   10  11  12

Trp Xaa
13  14
``` and a second amino acid sequence consisting of 5 amino acid residues having the following sequence

```
         Trp Cys Cys Xaa Cys (SEQ ID NO:80)
          1   2   3   4   5
``` wherein,
in position 3 of the first sequence, the amino acid is Trp, Tyr or Phe;
in position 4 of the first sequence, the amino acid is Trp, Tyr or Phe;
in position 8 of the first sequence, the amino acid is Arg, Lys or His;
in position 9, 10, 12 and 14, respectively, of the first sequence, and in position 4 of the second sequence, the amino acid is any of the 20 naturally occurring amino acid residues with the provisos that, in the first amino acid sequence, (i) when the amino residue in position 12 is Ser, then the amino acid residue in position 14 is not Ser, and (ii) when the amino residue in position 12 is Gly, then the amino acid residue in position 14 is not Ala.

Preferably, the enzyme of the invention is of microbial origin, i.e. obtainable from a microorganism such as a fungus.

In a preferred embodiment, the amino acid residue in position 9 of the first sequence is selected from the group consisting of proline, threonine, valine, alanine, leucine, isoleucine, phenylalanine, glycine, cysteine, asparagine, glutamine, tyrosine, serine, methionine and tryptophan, preferably from the group consisting of proline and threonine.

In another preferred embodiment, the amino acid residue in position 10 of the first sequence is selected from the group consisting of proline, threonine, valine, alanine, leucine, isoleucine, phenylalanine, glycine, cysteine, asparagine, glutamine, tyrosine, serine, methionine and tryptophan, preferably serine.

In yet another preferred embodiment, the amino acid residue in position 12 of the first sequence is selected from the group consisting of proline, threonine, valine, alanine, leucine, isoleucine, phenylalanine, glycine, cysteine, asparagine, glutamine, tyrosine, serine, methionine and tryptophan, preferably from the group consisting of alanine and glycine.

In yet another preferred embodiment, the amino acid residue in position 14 of the first sequence is selected from the group consisting of proline, threonine, valine, alanine, leucine, isoleucine, phenylalanine, glycine, cysteine, asparagine, glutamine, tyrosine, serine, methionine, tryptophan, glutamic acid and aspartic acid, preferably from the group consisting of proline, threonine, serine, alanine, glutamic acid and aspartic acid.

Preferably, the amino acid residue in position 4 of the second sequence is selected from the group consisting of proline, threonine, valine, alanine, leucine, isoleucine, phenylalanine, glycine, cysteine, asparagine, glutamine, tyrosine, serine, methionine, tryptophan, glutamic acid and aspartic acid, more preferably from the group consisting of alanine, glycine, and glutamine.

Examples of more preferred embodiments are such wherein, in the first sequence, the amino acid residue in position 3 is tyrosine; or the amino acid residue in position 4 is tryptophan; or the amino acid residue in position 8 is lysine.

In an especially preferred embodiment, the enzyme of the invention has a first sequence comprising the amino acid sequence

```
                                            (SEQ ID NO:79)
Thr Arg Tyr Trp Asp Cys Cys Lys Pro Ser Cys Ala
 1   2   3   4   5   6   7   8   9   10  11  12

Trp
13,
``` or the amino acid sequence

```
                                            (SEQ ID NO:79)
Thr Arg Tyr Trp Asp Cys Cys Lys Pro Ser Cys Ala
 1   2   3   4   5   6   7   8   9   10  11  12

Trp
13,
``` or the amino acid sequence

```
                                            (SEQ ID NO:79)
Thr Arg Tyr Trp Asp Cys Cys Lys Pro Ser Cys Ala
 1   2   3   4   5   6   7   8   9   10  11  12

Trp
13.
```

In a second aspect, the present invention provides a method for providing a microbial strain comprising a gene encoding such an enzyme which method comprises hybridization, e.g. PCR amplification, under standard conditions with an oligonucleotide derived from any of the conserved regions, illustrated in FIG. 1.

A useful oligonucleotide comprises a nucleotide sequence encoding at least a pentapeptide comprised in a peptide selected from the group consisting of a.

```
                                            (SEQ ID NO:79)
Thr Arg Xaa Xaa Asp Cys Cys Xaa Xaa Xaa Cys Xaa
 1   2   3   4   5   6   7   8   9   10  11  12

Trp Xaa
13  14
``` the amino acid in position 3 or 4 being Trp, Tyr or Phe;
the amino acid in postion 8 being Arg, Lys or His;
the amino acid in position 9, 10, 12 and 14, respectively, being any of the 20 naturally occurring amino acid residues; and b.

```
Trp Cys Cys Xaa Cys Tyr (SEQ ID NO:81)
 1   2   3   4   5   6
``` the amino acid in position 4 being any of the 20 naturally occurring amino acid residues; and c.

```
Xaa Pro Gly Gly Gly Xaa Gly Xaa Phe (SEQ ID
NO:82)
 1   2   3   4   5   6   7   8   9
``` the amino acid in position 1 being Met or Ile;
the amino acid in position 6 and 8, respectively, being Leu, Ile or Val; and d.

```
Gly Cys Xaa Xaa Arg Xaa Asp Trp Xaa (SEQ ID
NO:83)
 1   2   3   4   5   6   7   8   9
``` the amino acid in position 3 being any of the 20 naturally occurring amino acid residues;
the amino acid in position 4 and 6, respectively, being Trp, Tyr or Phe; and
the amino acid in position 9 being Phe or Met;

The useful oligonucleotides also comprises nucleotide sequences complementary to the sequences mentioned.

In a preferred embodiment of the method of the invention, the oligonucleotide corresponds to a PCR primer selected from the PCR primers sense:

5'-CCCCMGCTTACI$^A/_C$GITA$^C/_T$TGGGA$^C/_T$TG$^C/_T$TG$^C/_T$AA$^A/_G$$^A/_C$C-3' (SEQ ID NO:84) antisense 1:

5'-CTAGTCTAGATA$^A/_G$CAIGC$^A/_G$CA$^A/_G$CACC-3' (SEQ ID NO:85); antisense 2:

CTAGTCTAGAAAIA$^A/_G$/$^T$ICCIA$^A/^C$/$^G$ICCICCICCIGG-3' (SEQ ID NO:86); and antisense 3:

5'-CTAGTCTAGAIAACCA$^A/_G$TCA$^A/_G$$^A/_T$AIC$^G/_T$CC-3 (SEQ ID NO:87).

In a third aspect, the present invention provides an enzyme preparation which essentially consists of an enzyme having cellulytic activity and having the conserved regions found by the inventors, i.e. which comprises a peptide consisting of 7 amino acid residues having the following sequence (SEQ ID NOS: 105–107)

```
Xaa Thr Arg Xaa Phe Asp Xaa
 1   2   3   4   5   6   7;

Xaa Thr Arg Xaa Tyr Asp Xaa
 1   2   3   4   5   6   7; and

Xaa Thr Arg Xaa Trp Asp Xaa
 1   2   3   4   5   6   7
``` wherein, in position 4, Xaa is Trp, Tyr or Phe; and in position 1 and 7, Xaa is any of the 20 naturally occurring amino acid residues.

This enzyme is obtainable from a strain belonging to Basidiomycotous Hymenomycetes (see FIG. 2), more preferably to the group consisting of the orders Agaricales, Auriculariales, and Aphyllophorales, even more preferably to the group consisting of the families Exidiaceae, Tricholomataceae, Coprinaceae, Schizophyllaceae, Bjerkanderaceae and Polyporaceae, especially to the group consisting of the genera Exidia, Crinipellis, Fomes, Panaeolus, Trametes, Schizophyllum, and Spongipellis.

Specific examples are endoglucanases obtainable from a strain belonging to the group consisting of the species *Exidia glandulosa, Crinipellis scabella, Fomes fomentarius*, and Spongipellis sp., more specific examples being *Exidia glandulosa*, CBS 277.96, *Crinipellis scabella*, CBS 280.96, *Fomes fomentarius*, CBS 276.96, and Spongipellis sp., CBS 283.96.

*Exidia glandulosa* was deposited at Centraalbureau voor Schimmelcultures, Oosterstraat 1, Postbus 273, NL-3740 AG Baarn, the Netherlands, on Mar. 12, 1996, under the deposition number CBS 277.96; Crinipellis scabella was deposited at Centraalbureau voor Schimmelcultures on Mar. 12, 1996, under the deposition number CBS 280.96, *Fomes fomentarius* was deposited at Centraalbureau voor Schimmelcultures on Mar. 12, 1996, under the deposition number CBS 276.96, and Spongipellis sp. was deposited at Centraalbureau voor Schimmelcultures on Mar. 12, 1996, under the deposition number CBS 283.96; all deposited under the Budapest Treaty.

The enzyme preparation of the invention is also obtainable from a strain belonging to Chytridiomycota, preferably from a strain belonging to the class of Chytridiomycetes, more preferably belonging to the group consisting of the order Spizellomycetales, even more preferably to the family Spizellomycetaceae, especially belonging to the genus Rhizophlyctis. A specific example is a strain belonging to the species *Rhizophlyctis rosea*, more specifically to *Rhizophlyctis rosea*, CBS 282.96.

*Rhizophlyctis rosea* was deposited at Centraalbureau voor Schimmelcultures on Mar. 12, 1996, under the deposition number CBS 282.96; under the Budapest Treaty.

The enzyme preparation of the invention is also obtainable from a strain belonging to Zygomycota, preferably belonging to the class Zygomycetes, more preferably to the order Mucorales, even more preferably to the group of families consisting of Mucoraceae and Thamnidiaceae, especially belonging to the group consisting of the genera Rhizomucor, Phycomyces and Chaetostylum. Specific examples are strains belonging to the genera *Rhizomucor pusillus, Phycomyces nitens*, and *Chaetostylum fresenii* more specifically to *Rhizomucor pusillus*, IFO 4578, and *Phycomyces nitens*, IFO 4814 and *Chaetostylum fresenii*, NRRL 2305.

Further, the enzyme preparation of the invention is also obtainable from a strain belonging to the group consisting of Archaeascomycetes, Discomycetes, Hemiascomycetes, Loculoascomycetes, and Plectomycetes, preferably belonging to the group consisting of the orders Pezizales, Rhytismatales, Dothideales, and Eurotiales. Especially, the enzyme is obtainable from a strain belonging the the group consisting of the families Cucurbitariaceae, Ascobolaceae, Rhytismataceae, and Trichocomaceae, preferably belonging the the group consisting of the genera Diplodia, Microsphaeropsis, Ulospora, Macrophomina, Ascobolus, Saccobolus, Penicillium, and Thermomyces. Specific examples are enzymes obtainable from a strain belonging the the group consisting of the species *Diplodia gossypina*, Microsphaeropsis sp., *Ulospora bilgramii*, Aureobasidium sp., *Macrophomina phaseolina, Ascobolus stictoides, Saccobolus dilutellus*, Peziza, *Penicillium verruculosum, Penicillium chrysogenum*, and *Thermomyces verrucosus*; more specifically *Diplodia gossypina*, CBS 274.96, *Ulospora bilgramii*, NKBC 1444, *Macrophomina phaseolina*, CBS 281.96, *Saccobolus dilutellus*, CBS 275.96, *Penicillium verruculosum*, ATCC 62396, *Penicillium chrysogenum*, ATCC 9480, and *Thermomyces verrucosus*, CBS 285.96.

*Diplodia gossypina* was deposited at Centraalbureau voor Schimmelcultures on Mar. 12, 1996, under the deposition number CBS 274.96, *Macrophomina phaseolina* was deposited at Centraalbureau voor Schimmelcultures on Mar. 12, 1996, under the deposition number CBS 281.96, *Saccobolus dilutellus* was deposited at Centraalbureau voor Schimmelcultures on Mar. 12, 1996, under the deposition number CBS 275.96; *Thermomyces verrucosus* was deposited at Centraalbureau voor Schimmelcultures on Mar. 12, 1996, under the deposition number CBS 285.96; all under the Budapest Treaty.

Yet further, the enzyme is obtainable from a strain belonging to the group consisting of the orders Diaportales, Xylariales, Trichosphaeriales and Phyllachorales, preferably from a strain belonging to the group consisting of the families Xylariaceae, Valsaceae, and Phyllachoraceae, more preferably belonging to the genera Diaporthe, Colletotrichum, Nigrospora, Xylaria, Nodulisporum and Poronia. Specific examples are the species *Diaporthe syngenesia, Colletotrichum lagenarium, Xylaria hypoxylon,* Nigrospora sp., Nodulisporum sp., and *Poronia punctata,* more specifically *Diaporthe syngenesia,* CBS 278.96, *Colletotrichum lagenarium,* ATCC 52609, Nigrospora sp., CBS 272.96, *Xylaria hypoxylon,* CBS 284.96.

*Diaporthe syngenesia* was deposited at Centraalbureau voor Schimmelcultures on Mar. 12, 1996, under the deposition number CBS 278.96, Nigrospora sp. was deposited at Centraalbureau voor Schimmelcultures on Mar. 12, 1996, under the deposition number CBS 272.96, *Xylaria hypoxylon* was deposited at Centraalbureau voor Schimmelcultures on Mar. 12, 1996, under the deposition number CBS 284.96; all under the Budapest Treaty.

The enzyme is also obtainable from the unidentified fungal, mitosporic, coleomycetous deposited at Centraalbureau voor Schimmelcultures on Mar. 12, 1996, under the deposition numbers CBS 270.96, CBS 271.96 and CBS 273.96, respectively, under the Budapest Treaty.

The enzyme is also obtainable from a strain belonging to the group consisting of the genera Cylindrocarpon, Gliocladium, Nectria, Volutella, Sordaria, Scytalidium, Thielavia, Syspastospora, Cladorrhinum, Chaetomium, Myceliphthora and Acremonium, especially from a strain belonging to the group consisting of the species Cylindrocarpon sp., *Nectria pinea, Volutella colletotrichoides, Sordaria fimicola, Sordaria macrospora, Thielavia terrestris, Thielavia thermophila, Syspastospora boninensis, Cladorrhinum foecundissimum, Chaetomium murorum, Chaetomium virescens, Chaetomium brasiliensis, Chaetomium cunicolorum, Myceliophthora thermophila, Gliocladium catenulatum, Scytalidium thermophila,* and Acremonium sp., more specifically from *Nectria pinea,* CBS 279.96, *Volutella colletotrichoides,* CBS 400.58, *Sordaria fimicola,* ATCC 52644, *Sordaria macrospora,* ATCC 60255, *Thielavia terrestris,* NRRL 8126, *Thielavia thermophila,* CCBS 174.70, *Chaetomium murorum,* CBS 163.52, *Chaetomium virescens,* CBS 547.75, *Chaetomium brasiliensis,* CBS 122.65, *Chaetomium cunicolorum,* CBS 799.83, *Syspastospora boninensis,* NKBC 1515, *Cladorrhinum foecundissimum,* ATCC 62373, *Myceliophthora thermophila,* CBS 117.65, *Scytalidium thermophila,* ATCC 28085, Gliocladium catenulatum, ATCC 10523, and Acremonium sp., CBS 478.94.

*Nectria pinea* was deposited at Centraalbureau voor Schimmelcultures on Mar. 12, 1996, under the deposition number CBS 279.96, and Acremonium sp. was deposited on Sep. 28, 1994 under the deposition number CBS 478.94, both according to the Budapest Treaty.

The enzyme is also obtainable from a strain belonging to the group consisting of the species *Fusarium solani, Fusarium anguioides, Fusarium poae, Fusarium oxysporum* ssp. *lycopersici, Fusarium oxysporum* ssp. *passiflora, Humicola nigrescens* and *Humicola grisea,* especially *Fusarium oxysporum* ssp *lycopersici,* CBS 645.78, *Fusarium oxysporum* ssp passiflora, CBS 744.79, *Fusarium solani,* IMI 107.511, *Fusarium anguioides,* IFO 4467, *Fusarium poae,* ATCC 60883, *Humicola nigrescens,* CBS 819.73 and *Humicola grisea,* ATCC 22726. It is to be noted that *Humicola grisea* is different from *Humicola grisea* var. thermoidea.

In a preferred embodiment, the enzyme preparation of the invention is derived from the disclosed classes, orders, families, genera and species and essentially consists of an enzyme comprising a first peptide consisting of 13 amino acid residues having the following sequence

```
                                        (SEQ ID NO:79)
Thr Arg Xaa Xaa Asp Cys Cys Xaa Xaa Xaa Cys Xaa
 1   2   3   4   5   6   7   8   9  10  11  12

Trp Xaa
13  14
``` and a second peptide consisting of 5 amino acid residues having the following sequence

```
    Trp Cys Cys Xaa Cys   (SEQ ID NO:80)
     1   2   3   4   5
``` wherein, in position 3 of the first sequence, the amino acid is Trp, Tyr or Phe; in position 4 of the first sequence, the amino acid is Trp, Tyr or Phe; in position 8 of the first sequence, the amino acid is Arg, Lys or His; in position 9, 10, and 12, respectively, of the first sequence, and in position 4 of the second sequence, the amino acid is any of the 20 naturally occurring amino acid residues.

Preferably, the amino acid residue in position 9 of the first sequence is selected from the group consisting of proline, threonine, valine, alanine, leucine, isoleucine, phenylalanine, glycine, cysteine, asparagine, glutamine, tyrosine, serine, methionine and tryptophan, more preferably from the group consisting of proline and threonine; the amino acid residue in position 10 of the first sequence which is selected from the group consisting of proline, threonine, valine, alanine, leucine, isoleucine, phenylalanine, glycine, cysteine, asparagine, glutamine, tyrosine, serine, methionine and tryptophan, preferably serine; the amino acid residue in position 12 of the first sequence is selected from the group consisting of proline, threonine, valine, alanine, leucine, isoleucine, phenylalanine, glycine, cysteine, asparagine, glutamine, tyrosine, serine, methionine and tryptophan, preferably from the group consisting of alanine and glycine; and the amino acid residue in position 4 of the second sequence is selected from the group consisting of proline, threonine, valine, alanine, leucine, isoleucine, phenylalanine, glycine, cysteine, asparagine, glutamine, tyrosine, serine, methionine, tryptophan, glutamic acid and aspartic acid, more preferably from the group consisting of alanine, glycine, and glutamine.

In further aspects, the present invention provides a DNA construct comprising a DNA sequence encoding an enzyme exhibiting endoglucanase activity, which DNA sequence comprises a) the DNA sequence shown in SEQ ID No. 1, 7, 9, 11, 13, 15, 21, or 25, respectively, or the DNA sequence obtainable from the plasmid in *Saccharomyces cerevi-*

*siae* DSM 9770, DSM 10082, DSM 10080, DSM 10081, *Escherichia coli*, DSM 10512, DSM 10511, DSM 10571, DSM 10576, respectively; or b) an analogue of the DNA sequence shown in SEQ ID No. 1, 7, 9, 11, 13, 15, 21, or 25, respectively, or the DNA sequence obtainable from the plasmid in *Saccharomyces cerevisiae* DSM 9770, DSM 10082, DSM 10080, DSM 10081, *Escherichia coli*, DSM 10512, DSM 10511, DSM 10571, DSM 10576, respectively, which i) is homologous with the DNA sequence shown in SEQ ID No. 1, 7, 9, 11, 13, 15, 21, or 25, respectively, or the DNA sequence obtainable from the plasmid in *Saccharomyces cerevisiae* DSM 9770, DSM 10082, DSM 10080, DSM 10081, *Escherichia coli*, DSM 10512, DSM 10511, DSM 10571, DSM 10576, respectively, ii) hybridizes with the same oligonucleotide probe as the DNA sequence shown in SEQ ID No. 1, 7, 9, 11, 13, 15, 21, or 25, respectively, or the DNA sequence obtainable from the plasmid in *Saccharomyces cerevisiae* DSM 9770, DSM 10082, DSM 10080, DSM 10081, *Escherichia coli*, DSM 10512, DSM 10511, DSM 10571, DSM 10576, respectively, iii) encodes a polypeptide which is homologous with the polypeptide encoded by a DNA sequence comprising the DNA sequence shown in SEQ ID No. 1, 7, 9, 11, 13, 15, 21, or 25, respectively, or the DNA sequence obtainable from the plasmid in *Saccharomyces cerevisiae* DSM 9770, DSM 10082, DSM 10080, DSM 10081, *Escherichia coli*, DSM 10512, DSM 10511, DSM 10571, DSM 10576, respectively, iv) encodes a polypeptide which is immunologically reactive with an antibody raised against the purified endoglucanase encoded by the DNA sequence shown in SEQ ID No 1, 7, 9, 11, 13, 15, 21, or 25, respectively, or the DNA sequence obtainable from the plasmid in *Saccharomyces cerevisiae* DSM 9770, DSM 10082, DSM 10080, DSM 10081, *Escherichia coli*, DSM 10512, DSM 10511, DSM 10571, DSM 10576, respectively.

*Escherichia coli* DSM 10512 was deposited under the Budapest Treaty on Feb. 2, 1996, at DSM (Deutsche Sammlung von Mikroorganismen und Zellkulturen GmbH, Mascheroder Weg 16, D-38124 Braunschweig, Germany).

*Escherichia coli* DSM 10511 was deposited under the Budapest Treaty on Feb. 2, 1996, at DSM (Deutsche Sammlung von Mikroorganismen und Zellkulturen GmbH, Mascheroder Weg 16, D-38124 Braunschweig, Germany).

*Escherichia coli* DSM 10571 was deposited under the Budapest Treaty on Mar. 6, 1996, at DSM (Deutsche Sammlung von Mikroorganismen und Zellkulturen GmbH, Mascheroder Weg 16, D-38124 Braunschweig, Germany).

*Escherichia coli* DSM 10576 was deposited under the Budapest Treaty on Mar. 12, 1996, at DSM (Deutsche Sammlung von Mikroorganismen und Zellkulturen GmbH, Mascheroder Weg 16, D-38124 Braunschweig, Germany).

*Escherichia coli* DSM 10583 was deposited under the Budapest Treaty on Mar. 13, 1996, at DSM (Deutsche Sammlung von Mikroorganismen und Zellkulturen GmbH, Mascheroder Weg 16, D-38124 Braunschweig, Germany).

*Escherichia coli* DSM 10584 was deposited under the Budapest Treaty on Mar. 13, 1996, at DSM (Deutsche Sammlung von Mikroorganismen und Zellkulturen GmbH, Mascheroder Weg 16, D-38124 Braunschweig, Germany).

*Escherichia coli* DSM 10585 was deposited under the Budapest Treaty on Mar. 13, 1996, at DSM (Deutsche Sammlung von Mikroorganismen und Zellkulturen GmbH, Mascheroder Weg 16, D-38124 Braunschweig, Germany).

*Escherichia coli* DSM 10586 was deposited under the Budapest Treaty on Mar. 13, 1996, at DSM (Deutsche Sammiung von Mikroorganismen und Zellkulturen GmbH, Mascheroder Weg 16, D-38124 Braunschweig, Germany).

*Escherichia coli* DSM 10587 was deposited under the Budapest Treaty on Mar. 13, 1996, at DSM (Deutsche Sammlung von Mikroorganismen und Zellkulturen GmbH, Mascheroder Weg 16, D-38124 Braunschweig, Germany).

*Escherichia coli* DSM 10588 was deposited under the Budapest Treaty on Mar. 13, 1996, at DSM (Deutsche Sammlung von Mikroorganismen und Zellkulturen GmbH, Mascheroder Weg 16, D-38124 Braunschweig, Germany).

*Saccharomyces cerevisiae* DSM 9770 was deposited under the Budapest Treaty on Feb. 24, 1995, at DSM (Deutsche Sammlung von Mikroorganismen und Zellkulturen GmbH, Mascheroder Weg 16, D-38124 Braunschweig, Germany).

*Saccharomyces cerevisiae* DSM 10082 was deposited under the Budapest Treaty on Jun. 30, 1995, at DSM (Deutsche Sammlung von Mikroorganismen und Zellkulturen GmbH, Mascheroder Weg 16, D-38124 Braunschweig, Germany).

*Saccharomyces cerevisiae* DSM 10080 was deposited under the Budapest Treaty on Jun. 30, 1995, at DSM (Deutsche Sammlung von Mikroorganismen und Zellkulturen GmbH, Mascheroder Weg 16, D-38124 Braunschweig, Germany).

*Saccharomyces cerevisiae* DSM 10081 was deposited under the Budapest Treaty on Jun. 30, 1995, at DSM (Deutsche Sammlung von Mikroorganismen und Zellkulturen GmbH, Mascheroder Weg 16, D-38124 Braunschweig, Germany).

The DNA construct of the invention relating to SEQ ID No. 1 can be isolated from or produced on the basis of a DNA library of a strain of Myceliophthora, in particular a strain of *M. thermophila*, especially *M. thermophila*, CBS 117.65.

The DNA constructs of the invention relating to SEQ ID Nos. 7 and 9 can be isolated from or produced on the basis of a DNA library of a strain of Acremonium, especially Acremonium sp., CBS 478.94.

The DNA construct of the invention relating to SEQ ID No. 11 can be isolated from or produced on the basis of a DNA library of a strain of Thielavia in particular a strain of *Thielavia terrestris*, especially *Thielavia terrestris*, NRRL 8126.

The DNA construct of the invention relating to SEQ ID No. 13 can be isolated from or produced on the basis of a DNA library of a strain of Macrophomina, in particular a strain of *M. phaseolina*, especially *M. phaseolina*, CBS 281.96.

The DNA construct of the invention relating to SEQ ID No. 15 can be isolated from or produced on the basis of a DNA library of a strain of Crinipellis, in particular a strain of *C. scabella*, especially *C. scabella*, CBS 280.96.

The DNA construct of the invention relating to SEQ ID No. 25 can be isolated from or produced on the basis of a DNA library of a strain of Sordaria, in particular a strain of *Sordaria fimicola*.

In the present context, the "analogue" of the DNA sequence shown in SEQ ID No. 1, 7, 9, 11, 13, 15, 21, or 25, respectively, is intended to include any DNA sequence encoding an enzyme exhibiting endoglucanase activity, which has any or all of the properties i)–iv). The analogous DNA sequence a) may be isolated from another or related (e.g. the same) organism producing the enzyme with endoglucanase activity on the basis of the DNA sequence shown in SEQ ID No. 1, 7, 9, 11, 13, 15, 21, or 25, respectively, e.g. using the procedures described herein; the homologue may be an allelic variant of the DNA sequence comprising the DNA sequences shown herein, i.e. an alternative form of a gene that arises through mutation; mutations can be silent (no change in the encoded enzyme) or may encode enzymes having altered amino acid sequence; the homologue of the present DNA sequence may also be a genus or species homologue, i.e. encoding an enzyme with a similar activity derived from another species, b) may be constructed on the basis of the DNA sequences shown in SEQ ID No. 1, 7, 9, 11, 13, 15, 21, or 25, respectively, e.g. by introduction of nucleotide substitutions which do not give rise to another amino acid sequence of the endoglucanase encoded by the DNA sequence, but which correspond to the codon usage of the host organism intended for production of the enzyme, or by introduction of nucleotide substitutions which may give rise to a different amino acid sequence. However, in the latter case amino acid changes are preferably of a minor nature, that is conservative amino acid substitutions that do not significantly affect the folding or activity of the protein, small deletions, typically of one to about 30 amino acids; small amino- or carboxyl-terminal extensions, such as an amino-terminal methionine residue, a small linker peptide of up to about 20–25 residues, or a small extension that facilitates purification, such as a poly-histidine tract, an antigenic epitope or a binding domain. See in general Ford et al., *Protein Expression and Purification* 2: 95–107, 1991. Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine).

It will be apparent to persons skilled in the art that such substitutions can be made outside the regions critical to the function of the molecule and still result in an active polypeptide. Amino acids essential to the activity of the polypeptide encoded by the DNA construct of the invention, and therefore preferably not subject to substitution, may be identified according to procedures known in the art, such as site-directed mutagenesis or alanine-scanning mutagenesis (Cunningham and Wells, *Science* 244, 1081–1085, 1989). In the latter technique mutations are introduced at every residue in the molecule, and the resultant mutant molecules are tested for biological (i.e. endoglucanase) activity to identify amino acid residues that are critical to the activity of the molecule. Sites of substrate-enzyme interaction can also be determined by analysis of crystal structure as determined by such techniques as nuclear magnetic resonance, crystallography or photoaffinity labeling. See, for example, de Vos et al., *Science* 255: 306–312, 1992; Smith et al., *J. Mol. Biol.* 224: 899–904, 1992; Wlodaver et al., *FEBS Lett.* 309: 59–64, 1992.

The endoglucanase encoded by the DNA sequence of the DNA construct of the invention may comprise a cellulose binding domain (CBD) existing as an integral part of the encoded enzyme, or a CBD from another origin may be introduced into the endoglucanase enzyme thus creating an enzyme hybrid. In this context, the term "cellulose-binding domain" is intended to be understood as defined by Peter Tomme et al. "Cellulose-Binding Domains: Classification and Properties" in "Enzymatic Degradation of Insoluble Carbohydrates", John N. Saddler and Michael H. Penner (Eds.), ACS Symposium Series, No. 618, 1996. This definition classifies more than 120 cellulose-binding domains (CBDs) into 10 families (I–X), and it demonstrates that CBDs are found in various enzymes such as cellulases, xylanases, mannanases, arabinofuranosidases, acetyl esterases and chitinases. CBDs have also been found in algae, e.g., the red alga *Porphyra purpurea* as a non-hydrolytic polysaccharide-binding protein, for reference see Peter Tomme et al., supra. However, most of the CBDs are from cellulases and xylanases. CBDs are found at the N or C termini of proteins or are internal. Enzyme hybrids are known in the art, see e.g. WO 90/00609 and WO 95/16782, and may be prepared by transforming into a host cell a DNA construct comprising at least a fragment of DNA encoding the cellulose-binding domain ligated, with or without a linker, to a DNA sequence encoding the enzyme of interest and growing the host cell to express the fused gene. Enzyme hybrids may be described by the following formula:

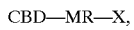

CBD—MR—X, wherein CBD is the N-terminal or the C-terminal region of an amino acid sequence corresponding to at least the cellulose-binding domain; MR is the middle region (the linker), and may be a bond, or a short linking group preferably of from about 2 to about 100 carbon atoms, more preferably of from 2 to 40 carbon atoms; or is preferably from about 2 to about 100 amino acids, more preferably of from 2 to 40 amino acids; and X is an N-terminal or C-terminal region of a polypeptide encoded by the DNA sequence of the invention.

The homology referred to in i) above is determined as the degree of identity between the two sequences indicating a derivation of the first sequence from the second. The homology may suitably be determined by means of computer programs known in the art such as GAP provided in the GCG program package (Needleman, S. B. and Wunsch, C. D., *Journal of Molecular Biology*, 48: 443–453, 1970). Using GAP with the following settings for DNA sequence comparison: GAP creation penalty of 5.0 and GAP extension penalty of 0.3, the coding region of the DNA sequence exhibits a degree of identity preferably of at least 60%, more preferably at least 65%, more preferably at least 70%, even more preferably at least 80%, especially at least 90%, with the coding region of the DNA sequence shown in SEQ ID No.1, 4, 6, 8, 10, 12, or 16, respectively, or the DNA sequence obtainable from the plasmid in *Saccharomyces cerevisiae*, DSM 9770, DSM 10082, DSM 10080, DSM 10081, *Escherichia coli*, DSM 10512, DSM 10511, DSM 10571, or DSM 10576, respectively.

The hybridization referred to in ii) above is intended to indicate that the analogous DNA sequence hybridizes to the same probe as the DNA sequence encoding the endoglucanase enzyme under certain specified conditions which are described in detail in the Materials and Methods section hereinafter. The oligonucleotide probe to be used is the DNA sequence corresponding to the endoglucanase encoding part of the DNA sequence shown in SEQ ID NO. 1, 7, 9, 11, 13, 15, or 21, respectively, or the DNA sequence obtainable from the plasmid in *Saccharomyces cerevisiae*, DSM 9770, DSM 10082, DSM 10080, DSM 10081, *Escherichia coli*, DSM 10512, DSM 10511, DSM 10571 or DSM 10576, respectively.

The homology referred to in iii) above is determined as the degree of identity between the two sequences indicating a derivation of the first sequence from the second. The homology may suitably be determined by means of computer programs known in the art such as GAP provided in the GCG program package (Needleman, S. B. and Wunsch, C. D., *Journal of Molecular Biology*, 48: 443–453, 1970). Using GAP with the following settings for polypeptide sequence comparison: GAP creation penalty of 3.0 and GAP extension penalty of 0.1, the polypeptide encoded by an analogous DNA sequence exhibits a degree of identity preferably of at least 55%, more preferably at least 60%, more preferably at least 65%, even more preferably at least 70%, more preferably at least 80%, especially at least 90%, with the enzyme encoded by a DNA construct comprising the DNA sequence shown in SEQ ID No. 1, 7, 9, 11, 13, 15, 21, or 25, respectively, or the DNA sequence obtainable from the plasmid in *Saccharomyces cerevisiae*, DSM 9770, DSM 10082, DSM 10080, DSM 10081, *Escherichia coli*, DSM 10512, DSM 10511, DSM 10571 or DSM 10576, respectively.

In connection with property iv) above it is intended to indicate an endoglucanase encoded by a DNA sequence isolated from strain *Saccharomyces cerevisiae*, DSM 9770, DSM 10082, DSM 10080, DSM 10081, *Escherichia coli*, DSM 10512, DSM 10511, DSM 10571 or DSM 10576, respectively, and produced in a host organism transformed with said DNA sequence or the corresponding endoglucanase naturally produced by *Myceliophthora thermophila*, Acremonium sp., *Thielavia terrestris, Macrophomina phaseolina, Crinipellis scabella, Volutella colletotrichoides*, or *Sordaria fimicola*, respectively. The immunological reactivity may be determined by the method described in the Materials and Methods section below.

In further aspects the invention relates to an expression vector harbouring a DNA construct of the invention, a cell comprising the DNA construct or expression vector and a method of producing an enzyme exhibiting endoglucanase activity which method comprises culturing said cell under conditions permitting the production of the enzyme, and recovering the enzyme from the culture.

In a still further aspect the invention relates to an enzyme exhibiting endoglucanase activity, which enzyme a) is encoded by a DNA construct of the invention b) produced by the method of the invention, and/or c) is immunologically reactive with an antibody raised against a purified endoglucanase encoded by the DNA sequence shown in SEQ ID No. 1, 7, 9, 11, 13, 15, or 21, respectively, or the DNA sequence obtainable from the plasmid in *Saccharomyces cerevisiae*, DSM 9770, DSM 10082, DSM 10080, DSM 10081, *Escherichia coli*, DSM 10512, DSM 10511, DSM 10571 or DSM 10576, respectively.

The endoglucanase mentioned in c) above may be encoded by the DNA sequence isolated from the strain *Saccharomyces cerevisiae*, DSM 9770, DSM 10082, DSM 10080, DSM 10081, *Escherichia coli*, DSM 10512, DSM 10511, DSM 10571 or DSM 10576, respectively, and produced in a host organism transformed with said DNA sequence or the corresponding endoglucanase naturally produced by *Myceliophthora thermophila*, Acremonium sp., *Thielavia terrestris, Macrophomina phaseolina, Crinipellis scabella, Volutella colletotrichoides* or *Sordaria fimicola*, respectively.

Generally, in the present context the term "enzyme" is understood to include a mature protein or a precursor form thereof as well to a functional fragment thereof which essentially has the activity of the full-length enzyme. Furthermore, the term "enzyme" is intended to include homologues of said enzyme.

Homologues of the present enzyme may have one or more amino acid substitutions, deletions or additions. These changes are preferably of a minor nature, that is conservative amino acid substitutions that do not significantly affect the folding or activity of the protein, small deletions, typically of one to about 30 amino acids; small amino- or carboxyl-terminal extensions, such as an amino-terminal methionine residue, a small linker peptide of up to about 20–25 residues, or a small extension that facilitates purification, such as a poly-histidine tract, an antigenic epitope or a binding domain. See in general Ford et al., *Protein Expression and Purification* 2: 95–107, 1991. Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine).

It will be apparent to persons skilled in the art that such substitutions can be made outside the regions critical to the function of the molecule and still result in an active enzyme. Amino acids essential to the activity of the enzyme of the invention, and therefore preferably not subject to substitution, may be identified according to procedures known in the art, such as site-directed mutagenesis or alanine-scanning mutagenesis (Cunningham, 1989). In the latter technique mutations are introduced at every residue in the molecule, and the resultant mutant molecules are tested for cellulytic activity to identify amino acid residues that are critical to the activity of the molecule. Sites of ligand-receptor interaction can also be determined by analysis of crystal structure as determined by such techniques as nuclear magnetic resonance, crystallography or photoaffinity labelling. See, for example, de Vos et al., 1992; Smith et al., 1992, Wlodaver et al., 1992.

The homologue may be an allelic variant, i.e. an alternative form of a gene that arises through mutation, or an altered enzyme encoded by the mutated gene, but having substantially the same activity as the enzyme of the invention. Hence mutations can be silent (no change in the encoded enzyme) or may encode enzymes having altered amino acid sequence.

The homologue of the present enzyme may also be a genus or species homologue, i.e. an enzyme with a similar activity derived from another species.

A homologue of the enzyme may be isolated by using the procedures described herein.

Molecular Screening and Cloning by Polymerase Chain Reaction (PCR)

Molecular screening for DNA sequences of the invention may be carried out by polymerase chain reaction (PCR) using genomic DNA or double-stranded cDNA isolated from a suitable source, such as any of the herein mentioned organisms, and synthetic oligonucleotide primers prepared on the basis of the DNA sequences or the amino acid sequences disclosed herein. For instance, suitable oligonucleotide primers may be the primers described in the Materials and Methods section.

In accordance with well-known procedures, the PCR fragment generated in the molecular screening may be isolated and subcloned into a suitable vector. The PCR fragment may be used for screening DNA libraries by e.g. colony or plaque hybridization.

Expression Cloning in Yeast

The DNA sequence of the invention encoding an enzyme exhibiting endoglucanase activity may be isolated by a general method involving cloning, in suitable vectors, a DNA library from a suitable source, such as any of the herein mentioned organisms transforming suitable yeast host cells with said vectors, culturing the host cells under suitable conditions to express any enzyme of interest encoded by a clone in the DNA library, screening for positive clones by determining any endoglucanase activity of the enzyme produced by such clones, and isolating the enzyme encoding DNA from such clones.

The general method is further disclosed in WO 94/14953 the contents of which are hereby incorporated by reference. A more detailed description of the screening method is given in Example 1 below.

The DNA sequence coding for the enzyme may for instance be isolated by screening a cDNA library of *Macrophomina phaseolina, Crinipellis scabella, Sordaria fimicola* or *Volutella colletotrichoides*, and selecting for clones expressing the appropriate enzyme activity (i.e. endoglucanase activity) or from *Escherichia coli* DSM 10512 deposited under the Budapest Treaty on Feb. 2, 1996, at DSM (Deutsche Sammlung von Mikroorganismen und Zellkulturen GmbH, Mascheroder Weg 16, D-38124 Braunschweig, Germany), or from *Escherichia coil* DSM 10511 deposited under the Budapest Treaty on Feb. 2, 1996, at DSM, or from *Escherichia coli* DSM 10576, deposited under the Budapest Treaty on Mar. 12, 1996, at DSM; or from *Escherichia coli* DSM 10571 deposited under the Budapest Treaty on Mar. 6, 1996, at DSM; or by screening a cDNA library of *Myceliphthora thermophila*, CBS 117.65, Acremonium sp., CBS 478.94, or *Thielavia terrestris*, NRRL 8126, and selecting for clones expressing the appropriate enzyme activity (i.e. endoglucanase activity) or from *Saccharomyces cerevisiae* DSM 9770 deposited under the Budapest Treaty on Feb. 24, 1995, at DSM (Deutsche Sammlung von Mikroorganismen und Zellkulturen GmbH, Mascheroder Weg 16, D-38124 Braunschweig, Germany), or from *Saccharomyces cerevisiae* DSM 10082 deposited under the Budapest Treaty on Jun. 30, 1995, at DSM, from *Saccharomyces cerevisiae* DSM 10080 deposited under the Budapest Treaty on Jun. 30, 1995, or from *Saccharomyces cerevisiae* DSM 10081 deposited under the Budapest Treaty on Jun. 30, 1995, at DSM. The appropriate DNA sequence may then be isolated from the clone by standard procedures, e.g. as described in Example 1.

Nucleic Acid Construct

As used herein the term "nucleic acid construct" is intended to indicate any nucleic acid molecule of cDNA, genomic DNA, synthetic DNA or RNA origin. The term "construct" is intended to indicate a nucleic acid segment which may be single- or double-stranded, and which may be based on a complete or partial naturally occurring nucleotide sequence encoding an enzyme of interest. The construct may optionally contain other nucleic acid segments.

The nucleic acid construct encoding the enzyme of the invention may suitably be of genomic or cDNA origin, for instance obtained by preparing a genomic or cDNA library and screening for DNA sequences coding for all or part of the enzyme by hybridization using synthetic oligonucleotide probes in accordance with standard techniques (cf. Sambrook et al., 1989).

The nucleic acid construct encoding the enzyme may also be prepared synthetically by established standard methods, e.g. the phosphoamidite method described by Beaucage and Caruthers, (1981), or the method described by Matthes et al., (1984). According to the phosphoamidite method, oligonucleotides are synthesized, e.g. in an automatic DNA synthesizer, purified, annealed, ligated and cloned in suitable vectors.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

The nucleic acid construct may also be prepared by polymerase chain reaction using specific primers, for instance as described in U.S. Pat. No. 4,683,202 or Saiki et al., (1988).

The nucleic acid construct is preferably a DNA construct which term will be used exclusively in this specification and claims.

Recombinant Vector

A recombinant vector comprising a DNA construct encoding the enzyme of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the enzyme of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the enzyme.

The promoter may be any DNA sequence which shows transcriptional activity in the host cell of choice and may be derived from genes encoding proteins either homologous or heterologous to the host cell.

Examples of suitable promoters for use in yeast host cells include promoters from yeast glycolytic genes (Hitzeman et al., *J. Biol. Chem.* 255 (1980), 12073–12080; Alber and Kawasaki, *J. Mol. Appl. Gen.* 1 (1982), 419–434) or alcohol dehydrogenase genes (Young et al., in *Genetic Engineering of Microorganisms for Chemicals* (Hollaender et al, eds.), Plenum Press, New York, 1982), or the TPI1 (U.S. Pat. No. 4,599,311) or ADH2-4c (Russell et al., *Nature* 304 (1983), 652–654) promoters.

Examples of suitable promoters for use in filamentous fungus host cells are, for instance, the ADH3 promoter (McKnight et al., *The EMBO J.* 4 (1985), 2093–2099) or the tpiA promoter. Examples of other useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* or *A.* awamori glucoamylase (gluA), *Rhizomucor miehei* lipase, *A. oryzae* alkaline protease, *A. oryzae* triose phosphate isomerase or *A. nidulans* acetamidase. Preferred are the TAKA-amylase and gluA promoters.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* BAN amylase gene, the *Bacillus subtilis* alkaline protease gen, or the *Bacillus pumilus* xylosidase gene, or by the phage Lambda $P_R$ or $P_L$ promoters or the *E. coli* lac, trp or tac promoters.

The DNA sequence encoding the enzyme of the invention may also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, such as the gene coding for dihydrofolate reductase (DHFR) or the *Schizosaccharomyces pombe* TPI gene (described by P. R. Russell, Gene 40, 1985, pp. 125–130). For filamentous fungi, selectable markers include amdS, pyrG, argB, niaD, sC.

To direct an enzyme of the present invention into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

For secretion from yeast cells, the secretory signal sequence may encode any signal peptide which ensures efficient direction of the expressed enzyme into the secretory pathway of the cell. The signal peptide may be naturally occurring signal peptide, or a functional part thereof, or it may be a synthetic peptide. Suitable signal peptides have been found to be the α-factor signal peptide (cf. U.S. Pat. No. 4,870,008), the signal peptide of mouse salivary amylase (cf. O. Hagenbuchle et al., *Nature* 289, 1981, pp. 643–646), a modified carboxypeptidase signal peptide (cf. L. A. Valls et al., *Cell* 48, 1987, pp. 887–897), the yeast BAR1 signal peptide (cf. WO 87/02670), or the yeast aspartic protease 3 (YAP3) signal peptide (cf. M. Egel-Mitani et al., *Yeast* 6, 1990, pp. 127–137).

For efficient secretion in yeast, a sequence encoding a leader peptide may also be inserted downstream of the signal sequence and upstream of the DNA sequence encoding the enzyme. The function of the leader peptide is to allow the expressed enzyme to be directed from the endoplasmic reticulum to the Golgi apparatus and further to a secretory vesicle for secretion into the culture medium (i.e. exportation of the enzyme across the cell wall or at least through the cellular membrane into the periplasmic space of the yeast cell). The leader peptide may be the yeast α-factor leader (the use of which is described in e.g. U.S. Pat. No. 4,546,082, EP 16 201, EP 123 294, EP 123 544 and EP 163 529). Alternatively, the leader peptide may be a synthetic leader peptide, which is to say a leader peptide not found in nature. Synthetic leader peptides may, for instance, be constructed as described in WO 89/02463 or WO 92/11378.

For use in filamentous fungi, the signal peptide may conveniently be derived from a gene encoding an *Aspergillus* sp. *amylase* or *glucoamylase*, a gene encoding a *Rhizomucor miehei* lipase or protease, a *Humicola lanuginosa* lipase. The signal peptide is preferably derived from a gene encoding *A. oryzae* TAKA amylase, *A. niger* neutral α-amylase, *A. niger* acid-stable amylase, or *A. niger* glucoamylase.

The procedures used to ligate the DNA sequences coding for the present enzyme, the promoter and optionally the terminator and/or secretory signal sequence, respectively, and to insert them into suitable vectors containing the information necessary for replication, are well known to persons skilled in the art (cf., for instance, Sambrook et al., op.cit.).

Host Cells

The DNA sequence encoding the present enzyme introduced into the host cell may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. The term "homologous" is intended to include a cDNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell which is capable of producing the present enzyme and includes bacteria, yeast, fungi and higher eukaryotic cells.

Examples of bacterial host cells which, on cultivation, are capable of producing the enzyme of the invention are gram-positive bacteria such as strains of Bacillus, such as strains of *B. subtilis, B. licheniformis, B. lentus, B. brevis, B. stearothermophilus, B. alkalophilus, B. amyloliquefaciens, B. coagulans, B. circulans, B. lautus, B. megatherium* or *B. thuringiensis*, or strains of Streptomyces, such as *S. lividans* or *S. murinus*, or gram-negative bacteria such as *Echerichia coli*. The transformation of the bacteria may be effected by protoplast transformation or by using competent cells in a manner known per se (cf. Sambrook et al., supra).

When expressing the enzyme in bacteria such as *E. coli*, the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

Examples of suitable yeasts cells include cells of Saccharomyces spp. or Schizosaccharomyces spp., in particular strains of *Saccharomyces cerevisiae* or *Saccharomyces kluyveri*. Methods for transforming yeast cells with heterologous DNA and producing heterologous enzymes therefrom are described, e.g. in U.S. Pat. No. 4,599,311, U.S. Pat. No. 4,931,373, U.S. Pat. Nos. 4,870,008, 5,037,743, and U.S. Pat. No. 4,845,075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931, 373. The DNA sequence encoding the enzyme of the invention may be preceded by a signal sequence and optionally a leader sequence, e.g. as described above. Further examples of suitable yeast cells are strains of Kluyveromyces, such as *K. lactis*, Hansenula, e.g. *H. polymorpha*, or Pichia, e.g. *P. pastoris* (cf. Gleeson et al., *J. Gen. Microbiol.* 132, 1986, pp. 3459–3465; U.S. Pat. No. 4,882,279).

Examples of other fungal cells are cells of filamentous fungi, e.g. Aspergillus spp., Neurospora spp., Fusarium spp. or Trichoderma spp., in particular strains of *A. oryzae, A. nidulans, A. niger*, or *Fusarium graminearum*. The use of Aspergillus spp. for the expression of proteins is described in, e.g., EP 272 277, EP 230 023. The transformation of *F. oxysporum* may, for instance, be carried out as described by Malardier et al., 1989, Gene 78: 147–156.

When a filamentous fungus is used as the host cell, it may be transformed with the DNA construct of the invention, conveniently by integrating the DNA construct in the host chromosome to obtain a recombinant host cell. This integration is generally considered to be an advantage as the DNA sequence is more likely to be stably maintained in the cell. Integration of the DNA constructs into the host chromosome may be performed according to conventional methods, e.g. by homologous or heterologous recombination.

The transformed or transfected host cell described above is then cultured in a suitable nutrient medium under conditions permitting the expression of the present enzyme, after which the resulting enzyme is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The enzyme produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of enzyme in question.

In a still further aspect, the present invention relates to a method of producing an enzyme according to the invention, wherein a suitable host cell transformed with a DNA sequence encoding the enzyme is cultured under conditions permitting the production of the enzyme, and the resulting enzyme is recovered from the culture.

Enzyme Screening Driven by Taxonomy as Well as Ecology

A powerful tool like the molecular screening disclosed herein, designed to detect and select said type of interesting enzymes, can still not stand on its own. In order to maximize the chances of making interesting discoveries the molecular screening approach was in the present investigation combined with careful selection of which fungi to screen. The selection was done through a thorough insight in the identification of fungi, in taxonomical classification and in phylogenetic relationships.

A taxonomic hot spot for production of cellulytic enzymes can further only be fully explored if also the ecological approach is included. Thorough knowledge about the adaptation to various substrates (especially saprotrophic, necrotrophic or biotrophic degradation of plant materials) are prerequisites for designing an intelligent screening and for managing a successful selection of strains and ecological niches to be searched.

Both the taxonomy and the ecological approach disclosed herein aim at maximizing discovery of said enzymes in the molecular screening program. However, still several hundreds (or if all preliminary work is included) several thousand fungi have been brought in culture in order to detect the 53 hits of said type of cellulytic enzyme here reported.

The screening and cloning may be carried out using the following:

MATERIALS AND METHODS

List of Organisms

*Saccharomyces cerevisiae*, DSM 9770, DSM 10082, DSM 10080, DSM 10081, or *Escherichia coli*, DSM 10512, DSM 10511, DSM 10571, DSM 10576, respectively, containing the plasmid comprising the full length DNA sequence, coding for the endoglucanase of the invention, in the shuttle vector pYES 2.0.

*Escherichia coli* DSM 10583, 10584, 10585, 10586, 10587, and 10588.

*Diplodia gossypina* Cooke

Deposit of Strain, Acc No: CBS 274.96

Classification: Ascomycota, Loculoascomycetes, Dothideales, Cucurbitariaceae

*Ulospora bilgramii* (Hawksw. et al.) Hawksw. et al.

Acc No of strain: NKBC 1444, Nippon University, (Prof. Tubaki collection)

Classification: Ascomycota, Loculoascomycetes, Dothideales, (family unclassified)

Microsphaeropsis sp.

Isolated from: Leaf of Camellia japonica (Theaceae, Guttiferales), grown in Kunming Botanical garden, Yunnan Province, China Classification: Ascomycota, Loculoascomycetes, Dothideales, (family unclassified)

*Macrophomina phaseolina* (Tassi) Goidannich

Syn: Rhizoctonia bataticola

Deposit of Strain, Acc No.:CBS 281.96

Isolated from seed of Glycine max (Leguminosa), cv CMM 60, grown in Thailand, 1990

Classification: Ascomycota, Discomycetes, Rhytismatales, Rhytismataceae

*Ascobolus stictoideus* Speg.

Isolated from goose dung, Svalbard, Norway

Classification: Ascomycota, Discomycetes, Pezizales, Ascobolaceae

*Saccobolus dilutellus* (Fuck.) Sacc.

Deposit of strain: Acc No CBS 275.96

Classification: Ascomycota, Discomycetes, Pezizales, Ascobolaceae

*Penicillium verruculosum* Peyronel

Ex on Acc No of species: ATCC 62396

Classification: Ascomycota, Plectomycetes, Eurotiales, Trichocomaceae

*Penicillium chrysogenum* Thom

Acc No of Strain: ATCC 9480
Classification: Ascomycota, Plectomycetes, Eurotiales, Trichocomaceae
*Thermomyces verrucosus* Pugh et al
Deposit of Strain, Acc No.: CBS 285.96
Classification: Ascomycota, Plectomycetes, Eurotiales, (family unclassified; affiliation based on 18S RNA, sequencing and homologies)
*Xylaria hypoxylon* L. ex Greville
Deposit of Strain, Acc No: CBS 284.96
Classification: Ascomycota, Pyrenomycetes, Xylariales, Xylariaceae
*Poronia punctata* (Fr. ex L.) Fr.
Classification: Ascomycota, Pyrenomycetes, Xylariales, Xylariaceae
Nodulisporum sp
Isolated from leaf of *Camellia reticulatá* (Theaceae, Guttiferales), grown in Kunming Botanical Garden, Yunnan Province, China
Classification: Ascomycota, Pyrenomycetes, Xylariales, Xylariaceae
Cylindrocarpon sp
Isolated from marine sample, the Bahamas
Classification: Ascomycota, Pyrenomycetes, Hypocreales (unclassified)
Acremonium sp
Deposit of Strain, Acc. No.: CBS 478.94
Classification: Ascomycota, Pyrenomycetes, Hypocreales, Hypocreaceae
*Fusarium anguioides* Sherbakoff
Acc No of strain: IFO 4467
Classification: Ascomycota, Pyrenomycetes, Hypocreales, Hypocreaceae
*Fusarium poae* (Peck) Wr.
Ex on Acc No of species: ATCC 60883
Classification: Ascomycota, Pyrenomycetes, Hypocreales, Hypocreaceae
*Fusarium solani* (Mart.)Sacc.emnd.Snyd & Hans.
Acc No of strain: IMI 107.511
Classification: Ascomycota, Pyrenomycetes, Hypocreales, Hypocreaceae
*Fusarium oxysporum* ssp *lycopersici* (Sacc.)Snyd. & Hans.
Acc No of strain: CBS 645.78
Classification: Ascomycota, Pyrenomycetes, Hypocreales, Hypocreaceae
*Fusarium oxysporum* ssp *passiflora*
Acc No of strain: CBS 744.79
Classification: Ascomycota, Pyrenomycetes, Hypocreales, Hypocreaceae
*Gliocladium catenulatum* Gillman & Abbott
Acc. No. of strain: CBS 227.48
Classification: Ascomycota, Pyrenomycetes, Hypocreales, Hypocreaceae
*Nectria pinea* Dingley
Deposit of Strain, Acc. No. CBS 279.96
Classification: Ascomycota, Pyrenomycetes, Hypocreales, Nectriaceae
*Volutella colletotrichoides*
Acc No of Strain: CBS 400.58
Classification: Ascomycota, Pyrenomycetes, Hypocreales (unclassified)

*Sordaria macrospora* Auerswald
Ex on Acc No of species: ATCC 60255
Classification: Ascomycota, Pyrenomycetes, Sordariales, Sordariaceae
*Sordaria fimicola* (Roberge) Cesati et De Notaris
Ex on Acc. No. for the species: ATCC 52644
Isolated from dung by H.Dissing, ISP, KU, Denmark
Classification: Ascomycota, Pyrenomycetes, Sordariales, Sordariaceae
*Humicola grisea* Traeen
ex on Acc No for the species: ATCC 22726
Source: Hatfield Polytechnic
Classification: Ascomycota, Pyrenomycetes, Sordariales, (fam. unclassified)
*Humicola nigrescens* Omvik
Acc No of strain: CBS 819.73
Classification: Ascomycota, Pyrenomycetes, Sordariales, (fam. unclassified)
*Scytalidium thermophilum* (Cooney et Emerson) Austwick
Acc No of strain: ATCC 28085
Classification: Ascomycota, Pyrenomycetes, Sordariales, (fam. unclassified)
*Thielavia thermophila* Fergus et Sinden
(syn Corynascus thermophilus)
Acc No of strain: CBS 174.70, IMI 145.136
Classification: Ascomycota, Pyrenomycetes, Sordariales, Chaetomiaceae
Isolated from Mushroom compost
*Thielavia terrestris* (Appinis) Malloch et Cain
Acc No of strain: NRRL8126
Classification: Ascomycota, Pyrenomycetes, Sordariales, Chaetomiaceae
*Cladorrhinum foecundissimum* Saccardo et Marchal
Ex on Acc No of species: ATCC 62373
Classification: Ascomycota, Pyrenomycetes, Sordariales, Lasiosphaeriaceae
Isolated from leaf of Selandin sp. (Compositaceae, Asterales), Dallas Mountain, Jamaica
*Syspastospora boninensis*
Acc No of strain: NKBC 1515 (Nippon University, profe Tubaki Collection)
Classification: Ascomycota, Pyrenomycetes, Sordariales, Cerastomataceae
*Chaetomium cuniculorum* Fuckel
Acc. No. of strain: CBS 799.83
Classification: Ascomycota, Pyrenomycetes, Sordariales, Chaetomiaceae
*Chaetomium brasiliense* Batista et Potual
Acc No of strain: CBS 122.65
Classification: Ascomycota, Pyrenomycetes, Sordariales, Chaetomiaceae
*Chaetomium murorum* Corda
Acc No of strain: CBS 163.52
Classification: Ascomycota, Pyrenomycetes, Sordariales, Chaetomiaceae
*Chaetomium virescens* (von Arx) Udagawa
Acc. No. of strain: CBS 547.75
Classification: Ascomycota, Pyrenomycetes, Sordariales, Chaetomiaceae
*Myceliophthora thermophila* (Apinis) Oorschot Deposit of Strain, Acc No:CBS 117.65
Classification: Ascomycota, Pyrenomycetes, Sordariales, Chaetomiaceae
*Nigrospora sp*
Deposit of strain, Acc No: CBS 272.96
Isolated from leaf of Artocarpus altilis, Moraceae, Urticales grown in Christiana, Jamaica
Classification: Ascomycota, Pyrenomycetes, Trichosphaeriales, (family unclassified)
*Nigrospora sp*
Isolated from leaf of Pinus yuannanensis, Botanical Garden, Kuning, Yunnan.
Classification: Ascomycota, Pyrenomycetes, Trichosphaeriales, Abietaceae, Pinales.
*Diaporthe syngenesia*
Deposit of strain, Acc No: CBS 278.96
Classification: Ascomycota, Pyrenomycetes, Diaporthales, Valsaceae
*Colletotrichum lagenarium* (Passerini) Ellis et Halsted
syn *Glomerella cingulata var orbiculare* Jenkins et Winstead
Ex on acc No of species: ATCC 52609
Classification: Ascomycota, Pyrenomycetes, Phyllachorales
*Exidia glandulosa* Fr.
Deposit of Strain, Acc No: CBS 277.96
Classification: Basidiomycota, Hymenomycetes, Auriculariales, Exidiaceae
*Crinipellis scabella* (Alb. & Schw.:Fr.)Murr
Deposit of strain: Acc No CBS 280.96
Classification: Basidiomycota, Hymenomycetes, Agaricales,
*Panaeolus retirugis* (Fr.) Gill.
Acc. No. of strain: CBS 275.47
Classification: Basidiomycota, Hymenomycetes, Agaricales, Coprinaceae
*Fomes fomentarius* (L.) Fr.
Deposit of strain: Acc No. CBS 276.96
Classification: Basidiomycota, Hymenomycetes, Aphyllophorales, Fomitaceae
*Spongipellis sp.*
Deposit of Strain: Acc No CBS 283.96
Classification: Basidiomycota, Hymenomycetes, Aphyllophorales,
Bjerkanderaceae (identified and affiliated taxonomically by 18S sequence and homology)
*Trametes sanguinea* (Fr.) Lloyd
syn: *Polyporus sanguineus*; *Pycnoporus sanguineus* (L.:Fr.) Murrill
Acc No of strain: AKU 5062 (Kyoto University Culture Collection)
Classification: Basidiomycota, Aphyllophorales, Polyporaceae
*Schizophyllum commune* Fr
Acc. No. of species: ATCC 38548
Classification: Basidiomycota, Aphyllophorales, Schizophyllaceae
*Rhizophlyctis rosea* (de Bary & Wor) Fischer
Deposit of Strain: Acc No.: CBS 282.96
Classification: Chytridiomycota, Chytridiomycetes, Spizellomycetales, Spizellomycetaceae
*Rhizomucor pusillus* (Lindt) Schipper
syn: *Mucor pusillus*
Acc No of strain: IFO 4578
Ex on Acc No of species: ATCC 46883
Classification: Zygomycota, Zygomycetes, Mucorales, Mucoraceae
*Phycomyces nitens* (Kunze) van Tieghem & Le Monnier
Acc No of strain: IFO 4814
Ex on Acc No of species: ATCC 16327
Classification: Zygomycota, Zygomycetes, Mucorales, Mucoraceae
*Chaetostylum fresenii* van Tieghem & Le Monnier
syn. *Helicostylum fresenii*
Acc No of strain NRRL 2305
Classification: Zygomycota, Zygomycetes, Mucorales, Thamnidiaceae
Unclassified:
*Trichothecium roseum*
Acc No of strain: IFO 5372
*Coniothecium sp*
Endophyte, isolated from leaf of unidentifed higher plant, growing in Kunming, Yunnan, China
Unclassified and Un-identified:
Deposit of strain, Acc No.: CBS 271.96
Isolated from leaf of *Artocarpus altilis* (Moraceae, Urticales), grown in Christiana, Jamaica
Deposit of strain, Acc No.: CBS 273.96
Isolated from leaf of *Pimenta dioica* (Myrtaceae, Myrtales) grown in Dallas Mountain, Jamaica
Deposit of strain: CBS 270.96
Isolated from leaf of Pseudocalymma alliaceum (Bignoniaceae, Solanales) growing in Dallas Mountain, Jamaica Other Strains

*Escherichia coli* MC1061 and DH10B.
Yeast strain: The *Saccharomyces cerevisiae* strain used was W3124 (MATα; ura 3-52; leu 2-3, 112; his 3-D200; pep 4-1137; prc1::HIS3; prbl:: LEU2; cir+).

Plasmids

The Aspergillus expression vector pHD414 is a derivative of the plasmid p775 (described in EP 238 023). The construction of pHD414 is further described in WO 93/11249.
pYES 2.0 (Invitrogen)
pA2C477, pA2C193, pA2C357, pA2C371, pA2C385, pA2C475, pA2C488, pA2C502 (See example 1, 2, 3 and 4).
Isolation of the DNA Sequence Shown in SEQ ID No. 1, 7, 9, 11, 13, 15, 21, or 25, Respectively:

The full length DNA sequence, comprising the cDNA sequence shown in SEQ ID No. 1, 7, 9, 11, 13, 15, 21, or 25, respectively, coding for the endoglucanase of the invention, can be obtained from the deposited organism *S. cerevisiae*, DSM 9770, DSM 10082, DSM 10080, DSM 10081, *E. coli*, DSM 10512, DSM 10511, DSM 10571 or DSM 10576, respectively, by extraction of plasmid DNA by methods known in the art (Sambrook et al. (1989) Molecular cloning: A laboratory manual, Cold Spring Harbor lab., Cold Spring Harbor, N.Y.).

PCR Primers for Molecular Screening of Cellulases of the Present invention:

The four degenerate, deoxyinosine-containing oligonucleotide primers (sense; s and antisense; as1, as2 and as3)

corresponding to four highly conserved amino acid regions found in the deduced amino acid sequences of *Thielavia terrestris* cellulase, *Myceliophthora thermophilum* cellulase, and two cellulases from Acremonium sp. The residues are numbered according to the *Myceliophthora thermophilum* sequence. The deoxyinosines are depicted by an I in the primer sequences, and the restriction sites are underlined.

```
              27                              35           (SEQ ID NO:79)
     NH2  -Thr Arg Tyr Trp Asp Cys Cys Lys Pro/Thr- COOH s 5'CCCCAAGCTT   ACI AGI TAC TGG GAC TGC TGC AAA AC -3'    (SEQ ID NO:84)
       HindIII       C   T       T   T   T   G C 106             111                          (SEQ ID NO:81)
     NH2  -Trp Cys Cys Ala Cys Tyr- COOH As1  3'-  CC ACA ACA CGI ACA AT AGATCTGATC -5'             (SEQ ID NO:85)
             G   G       G     XbaI 145                       152                (SEQ ID NO:82)
     NH2  -Pro Gly Gly Gly Leu/Val Gly Ile/Leu Phe- COOH As2  3'- GGI CCI CCI CCI AAI     CCI AAI    AA  AGATCTGATC -5'(SEQ ID NO:86)
                         C           G          XbaI
                         G           T 193             198                          (SEQ ID NO:83)
     NH2  -Trp Arg Phe/Tyr Asp Trp Phe- COOH As3  3'-  CC GCI AAA    CTA ACC AAA AGATCTTGATC -5'        (SEQ ID NO:87)
             T   TG             G   G    XbaI
```

Molecular Screening by Polymerase Chain Reaction (PCR):

In Vitro Amplification of Genomic DNA and Double-stranded cDNA

Directional, double-stranded cDNA was synthesized from 5 μg of poly(A)+ RNA as described below. Genomic DNA was isolated according to Yelton et al.

Approximately 10 to 20 ng of double-stranded, cellulase-induced cDNA or 100 to 200 ng of genomic DNA from a selection of fungal strains was PCR amplified in PCR buffer (10 mM Tris-HCl, pH 8.3, 50 mM KCl, 1.5 mM $MgCl_2$, 0.01% (w/v) gelatin) containing 200 μM of each dNTP and 100 pmol of each degenerate primer in three combinations:

1) sense,
   5'-CCCCAAGCTTACI$^A/_C$GITA$^C/_T$TGGGA$^C/_T$TG$^C/_T$TG$^C/_T$AA$^A/_G$$^A/_C$C-3' (SEQ ID NO:84) antisense 1,
   5'-CTAGTCTAGATA$^A/_G$CA/GC$^A/_G$CA$^A/_G$CACC-3' (SEQ ID NO:85); or 2) sense,
   5'-CCCCMGCTTACI$^A/_C$GITA$^C/_T$TGGGA$^C/_T$TG$^C/_T$TG$^C/_T$AA$^A/_G$$^A/_C$C-3' (SEQ ID NO:84) antisense 2,
   CTAGTCTAGAAAIA$^A/_G$/$^T$ICCIA$^A/^C$/$^G$ICCICCICCIGG-3' (SEQ ID NO:86); or 3) sense,
   5'-CCCCAAGCTTACI$^A/_C$GITA$^C/_T$TGGGA$^C/_T$TG$^C/_T$TG$^C/_T$AA$^A/_G$$^A/_C$C-3' (SEQ ID NO:84) antisense 3,
   5'-CTAGTCTAGAIAACCA$^A/_G$TCA$^A/_G$$^A/_T$AIC$^G/_T$CC-3 (SEQ ID NO:87);

a DNA thermal cycler (Landgraf, Germany) and 2.5 units of Taq polymerase (Perkin-Elmer, Cetus, USA). Thirty cycles of PCR were performed using a cycle profile of denaturation at 94° C. for 1 min, annealing at 64° C. for 2 min, and extension at 72° C. for 3 min. Ten-μl aliquots of the amplification products were analyzed by electrophoresis in 3% agarose gels (NuSieve, FMC) with HaeIII-digested φX174 RF DNA as a size marker.

Direct Sequencing of the PCR Products

Eighty-μl aliquots of the PCR products were purified using the QIAquick PCR purification kit (Qiagen, USA) according to the manufacturer's instructions. The nucleotide sequences of the amplified PCR fragments were determined directly on the purified PCR products by the dideoxy chain-termination method, using 50–150 ng template, the Taq deoxy-terminal cycle sequencing kit (Perkin-Elmer, USA), fluorescent labeled terminators and 5 pmol of the sense primer: 5'-CCCCAAGCTTACI$^A/_C$GITA$^C/_T$TGGGA$^C/_T$TG$^C/_T$TG$^C/_T$AA$^A/_G$$^A/_C$C-3' (SEQ ID NO:84). Analysis of the sequence data were performed according to Devereux et al.

Cloning by Polymerase Chain Reaction (PCR)

Subcloning of PCR Fragments

Twentyfive-μl aliquots of the PCR products generated as described above were electrophoresed in 0.8% low gelling temperature agarose (SeaPlaque GTG, FMC) gels, the relevant fragments were excised from the gels, and recovered by agarase treatment by adding 0.1 vol of 10×agarase buffer (New England Biolabs) and 2 units per 100 μl molten agarose to the sample, followed by incubation at 45° C. for 1.5 h. The sample was phenol and chloroform extracted, and precipitated by addition of 2 vols of 96% EtOH and 0.1 of 3 M NaAc, pH 5.2. The PCR fragments were recovered by centrifugation, washed in 70% EtOH, dried and resuspended in 20 μl of restriction enzyme buffer (10 mM Tris-HCl, 10 mM MgCl2, 50 mM NaCl, 1 mM DTT). The fragments were digested with HindIII and XbaI, phenol and chloroform extracted, recovered by precipitation with 2 vols of 96% EtOH and 0.1 of 3 M NaAc, pH 5.2, and subcloned into HindIII/XbaI-cleaved pYES 2.0 vector.

Screening of cDNA Libraries and Characterization of the Positive Clones cDNA libraries in *S. cerevisiae* or *E. coli*, constructed as described below, were screened by colony hybridization (Sambrook, 1989) using the corresponding random-primed (Feinberg and Vogelstein) $^{32}$P-labeled (>1×10$^9$ cpm/μg) PCR products as probes. The hybridizations were carried out in 2×SSC (Sambrook, 1989), 5×Denhardt's solution (Sambrook, 1989), 0.5% (w/v) SDS, 100 μg/ml denatured salmon sperm DNA for 20 h at 65° C. followed by washes in 5×SSC at 25° C. (2×15 min), 2×SSC, 0.5% SDS at 65° C. (30 min), 0.2×SSC, 0.5% SDS at 65° C. (30 min) and finally in 5×SSC (2×15 min) at 25° C. The positive cDNA clones were characterized by sequencing the ends of the cDNA inserts with pYES 2.0 polylinker primers (Invitrogen, USA), and by determining the nucleotide sequence of the longest cDNA from both strands by the dideoxy chain termination method (Sanger et al.) using fluorescent labeled terminators. Qiagen purified plasmid DNA (Qiagen, USA) was sequenced with the Taq deoxy terminal cycle sequencing kit (Perkin Elmer, USA) and either pYES 2.0 polylinker primers (Invitrogen, USA) or synthetic oligonucleotide primers using an Applied Biosystems 373A automated sequencer according to the manufacturers instructions. Analysis of the sequence data was performed according to Devereux et al.

Extraction of total RNA was performed with guanidinium thiocyanate followed by ultracentrifugation through a 5.7 M CsCl cushion, and isolation of poly(A)+ RNA was carried out by oligo(dT)-cellulose affinity chromatography using the procedures described in WO 94/14953.

cDNA Synthesis

Double-stranded cDNA was synthesized from 5 µg poly (A)+ RNA by the RNase H method (Gubler and Hoffman (1983) Gene 25:263–269, Sambrook et al. (1989) Molecular cloning: A laboratory manual, Cold Spring Harbor lab., Cold Spring Harbor, N.Y.) using the hair-pin modification developed by F. S. Hagen (pers. comm.). The poly(A)+ RNA (5 µg in 5 µl of DEPC-treated water) was heated at 70° C. for 8 min. in a pre-siliconized, RNase-free Eppendorph tube, quenched on ice and combined in a final volume of 50 µl with reverse transcriptase buffer (50 mM Tris-Cl, pH 8.3, 75 mM KCl, 3 mM MgCl$_2$, 10 mM DTT, Bethesda Research Laboratories) containing 1 mM of dATP, dGTP and dTTP and 0.5 mM 5-methyl-dCTP (Pharmacia), 40 units human placental ribonuclease inhibitor (RNasin, Promega), 1.45 µg of oligo(dT)$_{18}$-Not I primer (Pharmacia) and 1000 units SuperScript II RNase H reverse transcriptase (Bethesda Research Laboratories). First-strand cDNA was synthesized by incubating the reaction mixture at 45° C. for 1 hour. After synthesis, the mRNA:cDNA hybrid mixture was gelfiltrated through a MicroSpin S-400 HR (Pharmacia) spin column according to the manufacturer's instructions.

After the gelfiltration, the hybrids were diluted in 250 µl second strand buffer (20 mM Tris-Cl, pH 7.4, 90 mM KCl, 4.6 mM MgCl$_2$, 10 mM (NH$_4$)$_2$SO$_4$, 0.16 mM βNAD+) containing 200 µM of each dNTP, 60 units E. coli DNA polymerase I (Pharmacia), 5.25 units RNase H (Promega) and 15 units E. coli DNA ligase (Boehringer Mannheim). Second strand cDNA synthesis was performed by incubating the reaction tube at 16° C. for 2 hours and additional 15 min. at 25° C. The reaction was stopped by addition of EDTA to a final concentration of 20 mM followed by phenol and chloroform extractions.

Mung Bean Nuclease Treatment

The double-stranded cDNA was precipitated at −20° C. for 12 hours by addition of 2 vols 96% EtOH, 0.2 vol 10 M NH$_4$Ac, recovered by centrifugation, washed in 70% EtOH, dried and resuspended in 30 µl Mung bean nuclease buffer (30 mM NaAc, pH 4.6, 300 mM NaCl, 1 mM ZnSO$_4$, 0.35 mM DTT, 2% glycerol) containing 25 units Mung bean nuclease (Pharmacia). The single-stranded hair-pin DNA was clipped by incubating the reaction at 30° C. for 30 min., followed by addition of 70 µl 10 mM Tris-Cl, pH 7.5, 1 mM EDTA, phenol extraction and precipitation with 2 vols of 96% EtOH and 0.1 vol 3 M NaAc, pH 5.2 on ice for 30 min.

Blunt-ending with T4 DNA Polymerase

The double-stranded cDNAs were recovered by centrifugation and blunt-ended in 30 µl T4 DNA polymerase buffer (20 mM Tris-acetate, pH 7.9, 10 mM MgAc, 50 mM KAc, 1 mM DTT) containing 0.5 mM of each dNTP and 5 units T4 DNA polymerase (New England Biolabs) by incubating the reaction mixture at 16° C. for 1 hour. The reaction was stopped by addition of EDTA to a final concentration of 20 mM, followed by phenol and chloroform extractions, and precipitation for 12 hours at −20° C. by adding 2 vols 96% EtOH and 0.1 vol 3 M NaAc pH 5.2.

Adaptor Ligation, Not I Digestion and Size Selection

After the fill-in reaction the cDNAs were recovered by centrifugation, washed in 70% EtOH and dried. The cDNA pellet was resuspended in 25 µl ligation buffer (30 mM Tris-Cl, pH 7.8, 10 mM MgCl$_2$, 10 mM DTT, 0.5 mM ATP) containing 2.5 µg non-palindromic BstXI adaptors (Invitrogen) and 30 units T4 ligase (Promega) and incubated at 16° C. for 12 hours. The reaction was stopped by heating at 65° C. for 20 min. and then cooling on ice for 5 min. The adapted cDNA was digested with Not I restriction enzyme by addition of 20 µl water, 5 µl 10×Not I restriction enzyme buffer (New England Biolabs) and 50 units Not I (New England Biolabs), followed by incubation for 2.5 hours at 37° C. The reaction was stopped by heating at 65° C. for 10 min. The cDNAs were size-fractionated by gel electrophoresis on a 0.8% SeaPlaque GTG low melting temperature agarose gel (FMC) in 1×TBE to separate unligated adaptors and small cDNAs. The cDNA was size-selected with a cut-off at 0.7 kb and rescued from the gel by use of β-Agarase (New England Biolabs) according to the manufacturer's instructions and precipitated for 12 hours at −20° C. by adding 2 vols 96% EtOH and 0.1 vol 3 M NaAc pH 5.2.

Construction of Libraries

The directional, size-selected cDNA was recovered by centrifugation, washed in 70% EtOH, dried and resuspended in 30 µl 10 mM Tris-Cl, pH 7.5, 1 mM EDTA. The cDNAs were desalted by gelfiltration through a MicroSpin S-300 HR (Pharmacia) spin column according to the manufacturer's instructions. Three test ligations were carried out in 10 µl ligation buffer-(30 mM Tris-Cl, pH 7.8, 10 mM MgCl$_2$, 10 mM DTT, 0.5 mM ATP) containing 5 µl double-stranded cDNA (reaction tubes #1 and #2), 15 units T4 ligase (Promega) and 30 ng (tube #1), 40 ng (tube #2) and 40 ng (tube #3, the vector background control) of BstXI-NotI cleaved pYES 2.0 vector. The ligation reactions were performed by incubation at 16° C. for 12 hours, heating at 70° C. for 20 min. and addition of 10 µl water to each tube. 1 µl of each ligation mixture was electroporated into 40 µl electrocompetent E. coli DH10B cells (Bethesda research Laboratories) as described (Sambrook et al. (1989) Molecular cloning: A laboratory manual, Cold Spring Harbor lab., Cold Spring Harbor, N.Y.). Using the optimal conditions a library was established in E. coli consisting of pools. Each pool was made by spreading transformed E. coli on LB+ampicillin agar plates giving 15.000–30.000 colonies/plate after incubation at 37° C. for 24 hours. 20 ml LB+ampicillin was added to the plate and the cells were suspended herein. The cell suspension was shaked in a 50 ml tube for 1 hour at 37° C. Plasmid DNA was isolated from the cells according to the manufacturer's instructions using QIAGEN plasmid kit and stored at −20° C.

1 µl aliquots of purified plasmid DNA (100 ng/µl) from individual pools were transformed into *S. cerevisiae* W3124 by electroporation (Becker and Guarante (1991) Methods Enzymol. 194:182–187) and the transformants were plated on SC agar containing 2% glucose and incubated at 30° C.

Identification Positive Colonies

After 3–5 days of growth, the agar plates were replica plated onto a set of SC+ galactose-uracil agar plates containing 0.1% AZCL HE cellulose. These plates were incubated for 3–7 days at 30° C. Endoglucanase positive colonies were identified as colonies surrounded by a blue halo.

Cells from enzyme-positive colonies were spread for single colony isolation on agar, and an enzyme-producing single colony was selected for each of the endoglucanase-producing colonies identified.

Characterization of Positive Clones

The positive clones were obtained as single colonies, the cDNA inserts were amplified directly from the yeast colony using biotinylated polylinker primers, purified by magnetic beads (Dynabead M-280, Dynal) system and characterized individually by sequencing the 5'-end of each cDNA clone using the chain-termination method (Sanger et al. (1977) Proc. Natl. Acad. Sci. U.S.A. 74:5463–5467) and the Sequenase system (United States Biochemical).

The nucleotide sequence was determined of the longest cDNA from both strands by the dideoxy chain termination method (Sanger et al.) using fluorescent labeled terminators. Plasmid DNA was rescued by transformation into *E. coli* as described below. Qiagen purified plasmid DNA (Qiagen, USA) was sequenced with the Taq deoxy terminal cycle sequencing kit (Perkin Elmer, USA) and either pYES 2.0 polylinker primers (Invitrogen, USA) or synthetic oligonucleotide primers using an Applied Biosystems 373A automated sequencer according to the manufacturers instructions. Analysis of the sequence data was performed according to Devereux et al.

Isolation of a cDNA Gene for Expression in Aspergillus

An endoglucanase-producing yeast colony was inoculated into 20 ml YPD broth in a 50 ml glass test tube. The tube was shaken for 2 days at 30° C. The cells were harvested by centrifugation for 10 min. at 3000 rpm.

DNA was isolated according to WO 94/14953 and dissolved in 50 µl water. The DNA was transformed into *E. coli* by standard procedures. Plasmid DNA was isolated from *E. coli* using standard procedures, and analyzed by restriction enzyme analysis. The cDNA insert was excised using appropriate restriction enzymes and ligated into an Aspergillus expression vector.

Transformation of *Aspergillus oryzae* or *Aspergillus niger*

Protoplasts may be prepared as described in WO 95/02043, p. 16, line 21—page 17, line 12, which is hereby incorporated by reference.

100 µof protoplast suspension is mixed with 5–25 µg of the appropriate DNA in 10 µl of STC (1.2 M sorbitol, 10 mM Tris-HCl, pH=7.5, 10 mM $CaCl_2$). Protoplasts are mixed with p3SR2 (an *A. nidulans* amdS gene carrying plasmid). The mixture is left at room temperature for 25 minutes. 0.2 ml of 60% PEG 4000 (BDH 29576), 10 mM $CaCl_2$ and 10 mM Tris-HCl, pH 7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2 M sorbitol. After one more sedimentation the protoplasts are spread on minimal plates (Cove, Biochem. Biophys. Acta 113 (1966) 51–56) containing 1.0 M sucrose, pH 7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Test of *A. oryzae* Transformants

Each of the transformants were inoculated in 10 ml YPM and propagated. After 2–5 days of incubation at 37° C., 10 ml supernatant was removed. The endoglucanase activity was identified by AZCL HE cellulose as described above.

Hybridization conditions (to be used in evaluating property ii) of the DNA construct of the invention): Suitable conditions for determining hybridization between a nucleotide probe and a homologous DNA or RNA sequence involves presoaking of the filter containing the DNA fragments or RNA to hybridize in 5×SSC (standard saline citrate) for 10 min, and prehybridization of the filter in a solution of 5×SSC (Sambrook et al. 1989), 5×Denhardt's solution (Sambrook et al. 1989), 0.5% SDS and 100 µg/ml of denatured sonicated salmon sperm DNA (Sambrook et al. 1989), followed by hybridization in the same solution containing a random-primed (Feinberg, A. P. and Vogelstein, B. (1983) *Anal. Biochem.* 132:6–13), $^{32}$P-dCTP-labeled (specific activity>1×10$^9$ cpm/µg) probe for 12 hours at ca. 45° C. The filter is then washed two times for 30 minutes in 2×SSC, 0.5% SDS at preferably not higher than 50° C., more preferably not higher than 55° C., more preferably not higher than 60° C., more preferably not higher than 65° C., even more preferably not higher than 70° C., especially not higher than 75° C.

The nucleotide probe to be used in the hybridization is the DNA sequence corresponding to the endoglucanase encoding part of the DNA sequence shown in SEQ ID No. 1, 7, 9, 11, 13, 15, or 21, respectively, and/or the DNA sequence obtainable from the plasmid in *S. cerevisiae*, DSM 9770, DSM 10082, DSM 10080, DSM 10081, *E. coli*, DSM 10512, DSM 10511, DSM 10571 or DSM 10576, respectively.

Immunological Cross-reactivity

Antibodies to be used in determining immunological cross-reactivity may be prepared by use of a purified cellulase. More specifically, antiserum against the cellulase of the invention may be raised by immunizing rabbits (or other rodents) according to the procedure described by N. Axelsen et al. in: *A Manual of Quantitative Immunoelectrophoresis*, Blackwell Scientific Publications, 1973, Chapter 23, or A. Johnstone and R. Thorpe, *Immunochemistry in Practice*, Blackwell Scientific Publications, 1982 (more specifically pp. 27–31). Purified immunoglobulins may be obtained from the antisera, for example by salt precipitation (($NH_4)_2 SO_4$), followed by dialysis and ion exchange chromatography, e.g. on DEAE-Sephadex. Immunochemical characterization of proteins may be done either by Outcherlony double-diffusion analysis (O. Ouchterlony in: *Handbook of Experimental Immunology* (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

Media

YPD: 10 g yeast extract, 20 g peptone, $H_2O$ to 900 ml. Autoclaved, 100 ml 20% glucose (sterile filtered) added.

YPM: 10 g yeast extract, 20 g peptone, $H_2O$ to 900 ml. Autoclaved, 100 ml 20% maltodextrin (sterile filtered) added.

10×Basal salt: 75 g yeast nitrogen base, 113 g succinic acid, 68 g NaOH, $H_2O$ ad 1000 ml, sterile filtered.

SC-URA: 100 ml 10×Basal salt, 28 ml 20% casamino acids without vitamins, 10 ml 1% tryptophan, $H_2O$ ad 900 ml, autoclaved, 3.6 ml 5% threonine and 100 ml 20% glucose or 20% galactose added.

SC-URA agar: SC-URA, 20 g/l agar added.

PD agar: 39 g potato dextrose agar, DIFCO 0013; add deionized water up to 1000 ml; autoclave (121° C. for 15–20 min).

PC agar: Potatoes and carrots (grinded, 20 g of each) and water, added up to 1000 ml, are boiled for 1 hr; agar (20 g/l of Merck 1614); autoclave (121° C. for 20 min)

PC liquid broth: as PC agar but without the Agar

PD liquid broth: 24 g potato dextrose broth, Difco 0549, deionized water up to 1000 ml; autoclave (121° C. for 15–20 min)

PC and PD liquid broth with cellulose: add 30 g Solcafloc (Dicacel available 7–5 from Dicalite-Europe-Nord, 9000 Gent, Belgium) per 1000 ml.

PB-9 liquid broth: 12 g Rofec (Roquette 101-0441) and 24 g glucose are added to 1000 ml water; pH is adjusted to 5.5; 5 ml mineral oil and 5 g $CaCo_3$ are added per 1000 ml. Autoclave (121° C. for 40 min).

YPG liquid broth: 4 g yeast extract (Difco 0127), 1 g $KH_2PO_4$ (Merck 4873), 0.5 g $MgSO_4.7H2O$ Merck 5886, 15 g Dextrose, Roquette 101-0441, 0.1 ml Pluronic (101-3088); deionized water up to 1000 ml; autoclave (20 min at 121° C.).

Dilute salt solution (DS): Make up two stock solutions: P-stock: 13.61 g $KH_2PO_4$; 13.21 g $(NH_4)2PO_4$, 17.42 g $KH_2PO_4$; deionized water up 100 ml Ca/Mg stock: 7.35 g $CaCl_2$, $2H_2O$, 10.17 g $MgCl_2$, $6H_2O$, deionized water up to 100 ml; pH adjusted to 7.0; autoclaving (121° C.; 20 min)

Mix 0.5 ml P-stock with 0.1 ml Ca/Mg stock add deionized water up to 1000 ml AZCL HE cellulose (Megazyme, Australia).

Uses

During washing and wearing, dyestuff from dyed fabrics or garment will conventionally bleed from the fabric which then looks faded and worn. Removal of surface fibers from the fabric will partly restore the original colours and looks of the fabric. By the term "colour clarification", as used herein, is meant the partly restoration of the initial colours of fabric or garment throughout multiple washing cycles.

The term "de-pilling" denotes removing of pills from the fabric surface.

The term "soaking liquor" denotes an aqueous liquor in which laundry may be immersed prior to being subjected to a conventional washing process. The soaking liquor may contain one or more ingredients conventionally used in a washing or laundering process.

The term "washing liquor" denotes an aqueous liquor in which laundry is subjected to a washing process, i.e. usually a combined chemical and mechanical action either manually or in a washing machine. Conventionally, the washing liquor is an aqueous solution of a powder or liquid detergent composition.

The term "rinsing liquor" denotes an aqueous liquor in which laundry is immersed and treated, conventionally immediately after being subjected to a washing process, in order to rinse the laundry, i.e. essentially remove the detergent solution from the laundry. The rinsing liquor may contain a fabric conditioning or softening composition.

The laundry subjected to the method of the present invention may be conventional washable laundry. Preferably, the major part of the laundry is sewn or unsewn fabrics, including knits, wovens, denims, yarns, and toweling, made from cotton, cotton blends or natural or manmade cellulosics (e.g. originating from xylan-containing cellulose fibers such as from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyvinylidene chloride fibers, polyurethane fibers, polyurea fibers, aramid fibers), and cellulose-containing fibers (e.g. rayon/viscose, ramie, flax/linen, jute, cellulose acetate fibers, lyocell).

Detergent Compositions

According to one aspect of the present invention, the present endoglucanases may typically be components of a detergent composition. As such, they may be included in the detergent composition in the form of a non-dusting granulate, a stabilized liquid, or protected enzymes. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g. as powder, granules, paste or liquid. A liquid detergent may be aqueous, typically containing up to 70% water and 0–30% organic solvent, or nonaqueous.

The detergent composition comprises one or more surfactants, each of which may be anionic, nonionic, cationic, or zwitterionic. The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. It may also contain 0–40% of nonionic surfactant such as alcohol ethoxylate (AEO or AE), carboxylated alcohol ethoxylates, nonylphenol ethoxylate, alkylpolyglycoside, alkyldimethylamine oxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes such as amylase, lipase, cutinase, protease, peroxidase, and oxidase, e.g. laccase.

The detergent may contain 1–65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzenesulfonate (NOBS). Alternatively, the bleaching system may comprise peroxyacids of, e.g., the amide, imide, or sulfone type.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil-redeposition agents, dyes, bactericides, optical brighteners, or perfume.

The pH (measured in aqueous solution at use concentration) will usually be neutral or alkaline, e.g. in the range of 7–11.

Particular forms of detergent compositions within the scope of the invention include:

1) A detergent composition formulated as a granulate having a bulk density of at least 600 g/l comprising

| | |
|---|---|
| Linear alkylbenzenesulfonate (calculated as acid) | 7–12% |
| Alcohol ethoxysulfate (e.g. $C_{12-18}$ alcohol, 1–2 EO) or alkyl sulfate (e.g. $C_{16-18}$) | 1–4% |
| Alcohol ethoxylate (e.g. $C_{14-15}$ alcohol, 7 EO) | 5–9% |
| Sodium carbonate (as $N_2CO_3$) | 14–20% |
| Soluble silicate (as $NA_2O,2SiO_2$) | 2–6% |
| Zeolite (as $NaAlSiO_4$) | 15–22% |
| Sodium sulfate (as $Na_2SO_4$) | 0–6% |
| Sodium citrate/citric acid (as $C_6H_5Na_3O_7/C_6H_8O_7$) | 0–15% |
| Sodium perborate (as $NaBO_3.H_2O$) | 11–18% |
| TAED | 2–6% |
| Carboxymethylcellulose | 0–2% |
| Polymers (e.g. maleic/acrylic acid copolymer, PVP, PEG) | 0–3% |
| Enzymes (calculated as pure enzyme protein) | 0.0001–0.1% |
| Minor ingredients (e.g. suds suppressors, perfume, optical brightener, photobleach) | 0–5% |

2) A detergent composition formulated as a granulate having a bulk density of at least 600 g/l comprising

| | |
|---|---|
| Linear alkylbenzenesulfonate (calculated as acid) | 6–11% |
| Alcohol ethoxysulfate (e.g. $C_{12-18}$ alcohol, 1–2 EO or alkyl sulfate (e.g. $C_{16-18}$). | 1–3% |
| Alcohol ethoxylate (e.g. $C_{14-15}$ alcohol, 7 EO) | 5–9% |
| Sodium carbonate (as $Na_2CO_3$) | 15–21% |
| Soluble silicate (as $Na_2O,2SiO_2$) | 1–4% |
| Zeolite (as $NaAlSiO_4$) | 24–34% |
| Sodium sulfate (as $Na_2SO_4$) | 4–10% |
| Sodium citrate/citric acid (as $C_6H_5Na_3O_7/C_6H_8O_7$) | 0–15% |
| Carboxymethylcellulose | 0–2% |
| Polymers (e.g. maleic/acrylic acid copolymer, PVP, PEG) | 1–6% |
| Enzymes (calculated as pure enzyme protein) | 0.0001–0.1% |
| Minor ingredients (e.g. suds suppressors, perfume) | 0–5% |

3) A detergent composition formulated as a granulate having a bulk density of at least 600 g/l comprising

| | |
|---|---|
| Linear alkylbenzenesulfonate (calculated as acid) | 5–9% |
| Alcohol ethoxylate (e.g. $C_{12-15}$ alcohol, 7 EO) | 7–14% |
| Soap as fatty acid (e.g. $C_{16-22}$ fatty acid) | 1–3% |
| Sodium carbonate (as $Na_2CO_3$) | 10–17% |
| Soluble silicate (as $N_2O,2SiO_2$) | 3–9% |
| Zeolite (as $NaAlSiO_4$) | 23–33% |
| Sodium sulfate (as $Na_2SO_4$) | 0–4% |
| Sodium perborate (as $NaBO_3.H_2O$) | 8–16% |
| TAED | 2–8% |
| Phosphonate (e.g. EDTMPA) | 0–1% |
| Carboxymethylcellulose | 0–2% |
| Polymers (e.g. maleic/acrylic acid copolymer, PVP, PEG) | 0–3% |
| Enzymes (calculated as pure enzyme protein) | 0.0001–0.1% |
| Minor ingredients (e.g. suds suppressors, perfume, optical brightener) | 0–5% |

4) A detergent composition formulated as a granulate having a bulk density of at least 600 g/l comprising

| | |
|---|---|
| Linear alkylbenzenesulfonate (calculated as acid) | 8–12% |
| Alcohol ethoxylate (e.g. $C_{12-15}$ alcohol, 7 EO) | 10–25% |
| Sodium carbonate (as $Na_2CO_3$) | 14–22% |
| Soluble silicate (as $Na_2O,2SiO_2$) | 1–5% |
| Zeolite (as $NaAlSiO_4$) | 25–35% |
| Sodium sulfate (as $Na_2SO_4$) | 0–10% |
| Carboxymethylcellulose | 0–2% |
| Polymers (e.g. maleic/acrylic acid copolymer, PVP, PEG) | 1–3% |
| Enzymes (calculated as pure enzyme protein) | 0.0001–0.1% |
| Minor ingredients (e.g. suds suppressors, perfume) | 0–5% |

5) An aqueous liquid detergent composition comprising

| | |
|---|---|
| Linear alkylbenzenesulfonate (calculated as acid) | 15–21% |
| Alcohol ethoxylate (e.g. $C_{12-15}$ alcohol, 7 EO or $C_{12-15}$ alcohol, 5 EO) | 12–18% |

-continued

| | |
|---|---|
| Soap as fatty acid (e.g. oleic acid) | 3–13% |
| Alkenylsuccinic acid ($C_{12-14}$) | 0–13% |
| Aminoethanol | 8–18% |
| Citric acid | 2–8% |
| Phosphonate | 0–3% |
| Polymers (e.g. PVP, PEG) | 0–3% |
| Borate (as $B_4O_7$) | 0–2% |
| Ethanol | 0–3% |
| Propylene glycol | 8–14% |
| Enzymes (calculated as pure enzyme protein) | 0.0001–0.1% |
| Minor ingredients (e.g. dispersants, suds suppressors, perfume, optical brightener) | 0–5% |

6) An aqueous structured liquid detergent composition comprising

| | |
|---|---|
| Linear alkylbenzenesulfonate (calculated as acid) | 15–21% |
| Alcohol ethoxylate (e.g. $C_{12-15}$ alcohol, 7 EO, or $C_{12-15}$ alcohol, 5 EO) | 3–9% |
| Soap as fatty acid (e.g. oleic acid) | 3–10% |
| Zeolite (as $NaAlSiO_4$) | 14–22% |
| Potassium citrate | 9–18% |
| Borate (as $B_4O_7$) | 0–2% |
| Carboxymethylcellulose | 0–2% |
| Polymers (e.g. PEG, PVP) | 0–3% |
| Anchoring polymers such as, e.g., lauryl methacrylate/acrylic acid copolymer; molar ratio 25:1; MW 3800 | 0–3% |
| Glycerol | 0–5% |
| Enzymes (calculated as pure enzyme protein) | 0.0001–0.1% |
| Minor ingredients (e.g. dispersants,. suds suppressors, perfume, optical brighteners) | 0–5% |

7) A detergent composition formulated as a granulate having a bulk density of at least 600 g/l comprising

| | |
|---|---|
| Fatty alcohol sulfate | 5–10% |
| Ethoxylated fatty acid monoethanolamide | 3–9% |
| Soap as fatty acid | 0–3% |
| Sodium carbonate (as $Na_2CO_3$) | 5–10% |
| Soluble silicate (as $Na_2O,2SiO_2$) | 1–4% |
| Zeolite (as $NaAlSiO_4$) | 20–40% |
| Sodium sulfate (as $Na_2SO_4$) | 2–8% |
| Sodium perborate (as $NaBO_3.H_2O$) | 12–18% |
| TAED | 2–7% |
| Polymers (e.g. Maleic/acrylic acid copolymer, PEG) | 1–5% |
| Enzymes (calculated as pure enzyme protein) | 0.0001–0.1% |
| Minor ingredients (e.g. optical brightener, suds suppressors, perfume) | 0–5% |

8) A detergent composition formulated as a granulate comprising

| | |
|---|---|
| Linear alkylbenzenesulfonate (calculated as acid) | 8–14% |
| Ethoxylated fatty acid monoethanolamide | 5–11% |
| Soap as fatty acid | 0–3% |
| Sodium carbonate (as $Na_2CO_3$) | 4–10% |
| Soluble silicate (as $Na_2O,2SiO_2$) | 1–4% |
| Zeolite (as $NaAlSiO_4$) | 30–50% |
| Sodium sulfate (as $Na_2SO_4$) | 3–11% |
| Sodium citrate (as $C_6H_5Na_3O_7$) | 5–12% |
| Polymers (e.g. PVP, maleic/acrylic acid copolymer, PEG) | 1–5% |
| Enzymes (calculated as pure enzyme protein) | 0.0001–0.1% |
| Minor ingredients (e.g. suds suppressors, perfume) | 0–5% |

9) A detergent composition formulated as a granulate comprising

| | |
|---|---|
| Linear alkylbenzenesulfonate (calculated as acid) | 6–12% |
| Nonionic surfactant | 1–4% |
| Soap as fatty acid | 2–6% |
| Sodium carbonate (as $Na_2CO_3$) | 14–22% |
| Zeolite (as $NaAlSiO_4$) | 18–32% |
| Sodium sulfate (as $Na_2SO_4$) | 5–20% |
| Sodium citrate (as $C_6H_5Na_3O_7$) | 3–8% |
| Sodium perborate (as $NaBO_3.H_2O$) | 4–9% |
| Bleach activator (e.g. NOBS or TAED) | 1–5% |
| Carboxymethylcellulose | 0–2% |
| Polymers (e.g. polycarboxylate or PEG) | 1–5% |
| Enzymes (calculated as pure enzyme protein) | 0.0001–0.1% |
| Minor ingredients (e.g. optical brightener, perfume) | 0–5% |

10) An aqueous liquid detergent composition comprising

| | |
|---|---|
| Linear alkylbenzenesulfonate (calculated as acid) | 15–23% |
| Alcohol ethoxysulfate (e.g. $C_{12-15}$ alcohol, 2–3 EO) | 8–15% |
| Alcohol ethoxylate (e.g. $C_{12-15}$ alcohol, 7 EO, or $C_{12-15}$ alcohol, 5 EO) | 3–9% |
| Soap as fatty acid (e.g. lauric acid) | 0–3% |
| Aminoethanol | 1–5% |
| Sodium citrate | 5–10% |
| Hydrotrope (e. g. sodium toluensulfonate) | 2–6% |
| Borate (as $B_4O_7$) | 0–2% |
| Carboxymethylcellulose | 0–1% |
| Ethanol | 1–3% |
| Propylene glycol | 2–5% |
| Enzymes (calculated as pure enzyme protein) | 0.0001–0.1% |
| Minor ingredients (e.g. polymers, dispersants, perfume, optical brighteners) | 0–5% |

11) An aqueous liquid detergent composition comprising

| | |
|---|---|
| Linear alkylbenzenesulfonate (calculated as acid) | 20–32% |
| Alcohol ethoxylate (e.g. $C_{12-15}$ alcohol, 7 EO, or $C_{12-15}$ alcohol, 5 EO) | 6–12% |
| Aminoethanol | 2–6% |
| Citric acid | 8–14% |
| Borate (as $B_4O_7$) | 1–3% |
| Polymer (e.g. maleic/acrylic acid copolymer, anchoring polymer such as, e.g., lauryl methacrylate-/acrylic acid copolymer) | 0–3% |
| Glycerol | 3–8% |
| Enzymes (calculated as pure enzyme protein) | 0.0001–0.1% |
| Minor ingredients (e.g. hydrotropes, dispersants, perfume, optical brighteners) | 0–5% |

12) A detergent composition formulated as a granulate having a bulk density of at least 600 g/l comprising

| | |
|---|---|
| Anionic surfactant (linear alkylbenzenesulfonate, alkyl sulfate, alpha-olefinsulfonate, alpha-sulfo fatty acid methyl esters, alkanesulfonates, soap) | 25–40% |
| Nonionic surfactant (e.g. alcohol ethoxylate) | 1–10% |
| Sodium carbonate (as $Na_2CO_3$) | 8–25% |
| Soluble silicates (as $Na_2O, 2SiO_2$) | 5–15% |
| Sodium sulfate (as $Na_2SO_4$) | 0–5% |
| Zeolite (as $NaAlSiO_4$) | 15–28% |
| Sodium perborate (as $NaBO_3.4H_2O$) | 0–20% |
| Bleach activator (TAED or NOBS) | 0–5% |
| Enzymes (calculated as pure enzyme protein) | 0.0001–0.1% |
| Minor ingredients (e.g. perfume, optical brighteners) | 0–3% |

13) Detergent formulations as described in 1)–12) wherein all or part of the linear alkylbenzenesulfonate is replaced by ($C_{12}$–$C_{18}$) alkyl sulfate.

14) A detergent composition formulated as a granulate having a bulk density of at least 600 g/l comprising

| | |
|---|---|
| ($C_{12}$–$C_{18}$) alkyl sulfate | 9–15% |
| Alcohol ethoxylate | 3–6% |
| Polyhydroxy alkyl fatty acid amide | 1–5% |
| Zeolite (as $NaAlSiO_4$) | 10–20% |
| Layered disilicate (e.g. SK56 from Hoechst) | 10–20% |
| Sodium carbonate (as $Na_2CO_3$) | 3–12% |
| Soluble silicate (as $Na_2O,2SiO_2$) | 0–6% |
| Sodium citrate | 4–8% |
| Sodium percarbonate | 13–22% |
| TAED | 3–8% |
| Polymers (e.g. polycarboxylates and PVP— | 0–5% |
| Enzymes (calculated as pure enzyme protein) | 0.0001–0.1% |
| Minor ingredients (e.g. optical brightener, photo bleach, perfume, suds suppressors) | 0–5% |

15) A detergent composition formulated as a granulate having a bulk density of at least 600 g/l comprising

| | |
|---|---|
| ($C_{12}$–$C_{18}$) alkyl sulfate | 4–8% |
| Alcohol ethoxylate | 11–15% |
| Soap | 1–4% |
| Zeolite MAP or zeolite A | 35–45% |
| Sodium carbonate (as $Na_2CO_3$) | 2–8% |
| Soluble silicate (as $Na_2O,2SiO_2$) | 0–4% |
| Sodium percarbonate | 13–22% |
| TAED | 1–8% |
| Carboxymethyl cellulose | 0–3% |
| Polymers (e.g. polycarboxylates and PVP) | 0–3% |
| Enzymes (calculated as pure enzyme protein) | 0.0001–0.1% |
| Minor ingredients (e.g. optical brightener, phosphonate, perfume) | 0–3% |

16) Detergent formulations as described in 1)–15) which contain a stabilized or encapsulated peracid, either as an additional component or as a substitute for already specified bleach systems.

17) Detergent compositions as described in 1), 3), 7), 9) and 12) wherein perborate is replaced by percarbonate.

18) Detergent compositions as described in 1), 3), 7), 9), 12), 14) and 15) which additionally contain a manganese catalyst. The manganese catalyst may, e.g., be one of the compounds described in "Efficient manganese catalysts for low-temperature bleaching", Nature 369, 1994, pp. 637–639.

19) Detergent composition formulated as a nonaqueous detergent liquid comprising a liquid nonionic surfactant such as, e.g., linear alkoxylated primary alcohol, a builder system (e.g. phosphate), enzyme and alkali. The detergent may also comprise anionic surfactant and/or a bleach system.

The endoglucanase may be incorporated in concentrations conventionally employed in detergents. It is at present contemplated that, in the laundry composition of the invention, the cellulase may be added in an amount corresponding to 0.0001–10 mg (calculated as pure enzyme protein) of cellulase per liter of wash liquor.

According to yet another aspect of the present invention, endoglucanase may typically be a component of a fabric conditioning or softener composition. Examples of conventional softener compositions are disclosed in e.g. EP 0 233 910.

Textile Applications

In another embodiment, the present invention relates to use of the endoglucanase of the invention in the bio-polishing process. Bio-Polishing is a specific treatment of the yarn surface which improves fabric quality with respect to handle and appearance without loss of fabric wettability. The most important effects of Bio-Polishing can be characterized by less fuzz and pilling, increased gloss/luster, improved fabric handle, increased durable softness and altered water absorbency. Bio-Polishing usually takes place in the wet processing of the manufacture of knitted and woven fabrics. Wet processing comprises such steps as e.g. desizing, scouring, bleaching, washing, dying/printing and finishing. During each of these steps, the fabric is more or less subjected to mechanical action. In general, after the textiles have been knitted or woven, the fabric proceeds to a desizing stage, followed by a scouring stage, etc. Desizing is the act of removing size from textiles. Prior to weaving on mechanical looms, warp yarns are often coated with size starch or starch derivatives in order to increase their tensile strength. After weaving, the size coating must be removed before further processing the fabric in order to ensure a homogeneous and wash-proof result. It is known that in order to achieve the effects of Bio-Polishing, a combination of cellulytic and mechanical action is required. It is also known that "super-softness" is achievable when the treatment with a cellulase is combined with a conventional treatment with softening agents. It is contemplated that use of the endoglucanase of the invention for bio-polishing of cellulosic fabrics is advantageous, e.g. a more thorough polishing can be achieved. Bio-polishing may be obtained by applying the method described e.g. in WO 93/20278.

Stone-washing

It is known to provide a "stone-washed" look (localized abrasion of the colour) in dyed fabric, especially in denim fabric or jeans, either by washing the denim or jeans made from such fabric in the presence of pumice stones to provide the desired localized lightening of the colour of the fabric or by treating the fabric enzymatically, in particular with cellulytic enzymes. The treatment with an endoglucanase of the present invention may be carried out either alone such as disclosed in U.S. Pat. No. 4,832,864, together with a smaller amount of pumice than required in the traditional process, or together with perlite such as disclosed in WO 95/09225.

Pulp and Paper Applications

In the papermaking pulp industry, the endoglucanase of the present invention may be applied advantageously e.g. as follows:

For debarking: pretreatment with the endoglucanase may degrade the cambium layer prior to debarking in mechanical drums resulting in advantageous energy savings.

For defibration: treatment of a material containing cellulosic fibers with the endoglucanase prior to refining or beating may result in reduction of the energy consumption due to the hydrolysing effect of the cellulase on the interfibre surfaces. Use of the endoglucanase may result in improved energy savings as compared to the use of known enzymes, since it is believed that the enzyme composition of the invention may possess a higher ability to penetrate fibre walls.

For fibre modification, i.e. improvement of fibre properties where partial hydrolysis across the fibre wall is needed which requires deeper penetrating enzymes (e.g. in order to make coarse fibers more flexible). Deep treatment of fibers has so far not been possible for high yield pulps e.g. mechanical pulps or mixtures of recycled pulps. This has been ascribed to the nature of the fibre wall structure that prevents the passage of enzyme molecules due to physical restriction of the pore matrix of the fibre wall. It is contemplated that the present endoglucanase is capable of penetrating into the fibre wall.

For drainage improvement. The drainability of papermaking pulps may be improved by treatment of the pulp with hydrolysing enzymes, e.g. cellulases. Use of the present endoglucanase may be more effective, e.g. result in a higher degree of loosening bundles of strongly hydrated micro-fibrils in the fines fraction (consisting of fibre debris) that limits the rate of drainage by blocking hollow spaces between fibers and in the wire mesh of the paper machine. The Canadian standard freeness (CSF) increases and the Schopper-Riegler drainage index decreases when pulp in subjected to cellulase treatment, see e.g. U.S. Pat. No. 4,923,565; TAPPI T227, SCAN C19:65.ence.

For inter fibre bonding. Hydrolytic enzymes are applied in the manufacture of papermaking pulps for improving the inter fibre bonding. The enzymes rinse the fibre surfaces for impurities e.g. cellulosic debris, thus enhancing the area of exposed cellulose with attachment to the fibre wall, thus improving the fibre-to-fibre hydrogen binding capacity. This process is also referred to as dehornification. Paper and board produced with a cellulase containing enzyme preparation may have an improved strength or a reduced grammage, a smoother surface and an improved printability.

For enzymatic deinking. Partial hydrolysis of recycled paper during or upon pulping by use of hydrolysing enzymes such as cellulases are known to facilitate the removal and agglomeration of ink particles. Use of the present endoglucanse may give a more effective loosening of ink from the surface structure due to a better penetration of the enzyme molecules into the fibrillar matrix of the fibre wall, thus softening the surface whereby ink particles are effectively loosened. The agglomeration of loosened ink particles are also improved, due to a more efficient hydrolysis of cellulosic fragments found attached to ink particles originating from the fibres.

The treatment of lignocellulosic pulp may, e.g., be performed as described in WO 91/14819, WO 91/14822, WO 92/17573 and WO 92/18688.

Degradation of Plant Material

In yet another embodiment, the present invention relates to use of the endoglucanase and/or enzyme preparation according to the invention for degradation of plant material e.g. cell walls.

It is contemplated that the novel endoglucanase and/or enzyme preparation of the invention is useful in the preparation of wine, fruit or vegetable juice in order to increase yield. Endoglucanases according to the invention may also be applied for enzymatic hydrolysis of various plant cellwall derived materials or waste materials, e.g. agricultural residues such as wheat-straw, corn cobs, whole corn plants, nut shells, grass, vegetable hulls, bean hulls, spent grains, sugar beet pulp, and the like. The plant material may be degraded in order to improve different kinds of processing, facilitate purification or extraction of other components like purification of beta-glucan or beta-glucan oligomers from cereals, improve the feed value, decrease the water binding capacity, improve the degradability in waste water plants, improve the conversion of e.g. grass and corn to ensilage, etc.

The following examples illustrate the invention.

EXAMPLE 1

Cellulytic enzymes from 4 fungi, belonging to 3 families under two orders within the Ascomycetes were detected by expression cloning; corresponding DNA sequences were determined; the enzymes heterologously expressed, and produced by liquid fermentation, characterized and demonstrated to give good performance in colour clarification assays.

Isolate CBS 117.65, CBS 478.94, NRRL 8126, and ATCC 10523 were grown in shake flask cultures on cellulose enriched potato dextrose broth, incubated for 5 days at 26° C. (shaking conditions, 150 rpm).

A. Cloning and Expression of an Endoglucanase from *Myceliophthora thermophila*, Acremonium sp., and *Thielavia terrestris* and *Volutella colletotrichoides* mRNA was isolated from *Myceliophthora thermophila*, Acremonium sp., *Thielavia terrestris* and *Volutella colletotrichoides*, respectively, grown in a cellulose-containing fermentation medium with agitation to ensure sufficient aeration. Mycelia were harvested after 3–5 days' growth, immediately frozen in liquid nitrogen and stored at −80° C. Libraries from *Myceliophthora thermophila*, Acremonium sp., *Thielavia terrestris* and *Volutella colletotrichoides*, respectively, each consisting of approx. $10^6$ individual clones were constructed in *E. coli* as described with a vector background of 1%.

Plasmid DNA from some of the pools from each library was transformed into yeast, and 50–100 plates containing 250–400 yeast colonies were obtained from each pool.

Endoglucanase-positive colonies were identified and isolated on SC-agar plates with the AZCL HE cellulose assay. cDNA inserts were amplified directly from the yeast colonies and characterized as described in the Materials and Methods section above.

The DNA sequence of the cDNA encoding the endoglucanase from *Myceliophthora thermophila* is shown in SEQ ID No. 1 and the corresponding amino acid sequence is shown in SEQ ID No. 2. The cDNA is obtainable from the plasmid in DSM 9770.

The DNA sequence of the cDNA encoding the endoglucanase from Acremonium sp. is shown in SEQ ID No. 7 and the corresponding amino acid sequence is shown in SEQ ID No. 8. The cDNA is obtainable from the plasmid in DSM 10082.

The DNA sequence of the cDNA encoding the endoglucanase from *Thielavia terrestris* is shown in SEQ ID No. 11 and the corresponding amino acid sequence is shown in SEQ ID No. 12. The cDNA is obtainable from the plasmid in DSM 10081.

The DNA sequence of the cDNA encoding the endoglucanase from *Volutella colletotrichoides* is shown in SEQ ID No. 21 and the corresponding amino acid sequence is shown in SEQ ID No. 22. The cDNA is obtainable from the plasmid in DSM 10571.

Total DNA was isolated from a yeast colony and plasmid DNA was rescued by transformation of *E. coli* as described above. In order to express the endoglucanases in Aspergillus, the DNA was digested with appropriate restriction enzymes, size fractionated on gel, and a fragment corresponding to the endoglucanase gene from *Myceliophthora thermophila*, Acremonium sp., *Thielavia terrestris* and

*Volutella colletotrichoides*, respectively, was purified. The genes were subsequently ligated to pHD414, digested with appropriate restriction enzymes, resulting in the plasmids pA2C193, pA2C357, pA2C385 and pA2C488, respectively.

After amplification of the DNA in *E. coli* the plasmids were transformed into *Aspergillus oryzae* as described above.

Test of *A. oryzae* Transformants

Each of the transformants were tested for endoglucanase activity as described above. Some of the transformants had endoglucanase activity which was significantly larger than the *Aspergillus oryzae* background. This demonstrates efficient expression of the endoglucanases in *Aspergillus oryzae*. The transformants with the highest endoglucanase activity were selected and inoculated in a 500 ml shake flask with YPM media. After 3–5 days of fermentation with sufficient agitation to ensure good aeration, the culture broth was centrifuged for 10 minutes at 2000 g and the supernatant recovered.

B. Determination of Endoglucanase Activity

The cellulytic activity of the endoglucanase may be determined relative to an analytical standard and expressed in the unit S-CEVU.

Cellulytic enzymes hydrolyse CMC, thereby decreasing the viscosity of the incubation mixture. The resulting reduction in viscosity may be determined by a vibration viscosimeter (e.g. MIVI 3000 from Sofraser, France).

Determination of the cellulytic activity, measured in terms of S-CEVU, may be determined according to the analysis method AF 301.1 which is available from the Applicant upon request.

The S-CEVU assay quantifies the amount of catalytic activity present in the sample by measuring the ability of the sample to reduce the viscosity of a solution of carboxymethylcellulose (CMC). The assay is carried out at 40° C., pH 7.5 using a relative enzyme standard for reducing the viscosity of the CMC substrate.

Assay for determination of endoglucanase activity in terms of SAVI units using phosphoric-acid swollen cellulose (PASC):
Definition: 1 SAVI-U is the amount of enzyme which forms an amount of reducing carbohydrates equivalent to 1 $\mu$mol of glucose per minute.
Assay Condition:
  Enzyme solution: 0.5 ml
  4 g/l PASC in 0,1 M Buffer: 2.0 ml
  20 min, 40° C.
Sensitivity:
  Max 0.1 SAVIU/ml =approx. 1 S-CEVU/ml (CMC viscosity)
  Min 0.01 SAVIU/ml =approx. 0.1 S-CEVU/ml
Determination of Formation of Reducing Sugars:
  The reducing groups assay was performed according to Lever, M. A new reaction for colorimetric determination of carbohydrates. Anal. Biochem. 1972. Vol 47 (273–279). Reagent mixture was prepared by mixing 1,5 gram p-hydroxybenzoic-acide hydracide (PHBAH) with 5 gram sodium tartrate in 100 ml 2% sodium hydroxide.
Substrate:
  PASC stock solution was prepared the following way using ice cold acetone and phosphoric acid. 5 gram of cellulose (Avicel®) was moistered with water, and 150 ml ice cold 85% ortho-phosphoric acid was added. The mixture was placed in ice bath under slow stirring for 1 hr. Then 100 ml ice cold acetone was added with stirring. The slurry was transferred to a Buchner filter with pyrex sintered disc number 3 and then washed three times with 100 ml ice cold acetone, and sucked as dry as possible after each wash. Finally, the filter cake was washed twice with 500 ml water, sucked as dry as possible after each wash. The PASC was mixed with deionized water to a total volume of 300 ml, blended to homogeneity (using the Ultra Turrax Homogenizer) and stored in refrigerator (up to one month).

Substrate equilibration with buffer: 20 gram phosphoric acid swollen cellulose PASC stock solution was centrifuged for 20 min at 5000 rpm., the supernatant was poured of; the sediment was resuspended in 30 ml of buffer and centrifuged for 20 min. at 5000 rpm., the supernatant was poured of, and the sediment was resuspended in buffer to a total of 60 g corresponding to a substrate concentration of 5 g cellulose/ litre.
  Buffer for pH 8,5 determination: 0.1 M Barbital.
  Buffer for pH 10 determination: 0.1 M Glycine.
Procedure:
1. Dilution of Enzyme Samples
   The enzyme solution is diluted in the same buffer as the substrate.
2. Enzyme Reaction
   The substrate in buffer solution is preheated for 5 min. at 40° C. (2 ml). Then the enzyme solution (diluted to between 0.2 and 1 S-CEVU/ml) 0,5 ml is added and mixed for 5 sec. Enzymes blanks are obtained by adding the stop reagent before enzyme solution. Incubate for 20 min. at 40° C. The reaction is stopped by adding 0.5 ml 2% NaOH solution and mixing for 5 sec.
   The samples are centrifuged for 20 min. at 5000 rpm. 1 ml supernatant is mixed with 0.5 ml PHBAH reagent and boiled for 10 min. The test tubes are cooled in a ice water bath.
3. Determination of Reducing end Groups:
   The absorbancy at 410 nm is measured using a spectrophotometer. Blanks are prepared by adding sodium hydroxide before adding enzyme solution.
   A standard glucose curve was obtained by using glucose concentrations of 5, 10, 15 and 25 mg/l in the same buffer and adding PHBAH reagent before boiling. The release of reducing glucose equivalent is calculated using this standard curve.
4. Calculation of Catalytic Activity:
   Measure absorbance at 410 nm
   1) Standard Curve
      (Glucose)—($H_2O$) vs concentration of glucose
   2) Enzyme Sample
      (Sample)—(Blank)
   Calculate glucose concentration according to a standard curve Activity (SAVIU/ml):

$$\frac{X(\text{mg glucose}/1) * \text{Dilution}}{180.16 (\text{MW of glucose}) * 20 (\text{min})}$$

C. Purification and Characterisation of the Endoglucanase from *M. thermophila*

*Aspergillus oryzae* transformed with pA2C193 was grown on YPM medium for 4 days. The liquid was then centrifuged and sterile filtered.

The sample was concentrated by ultrafiltration on AMICON cells using a DOW membrane GR61PP with cut-off 20 kD. The Uf-concentrate was analyzed for S-CEVU/ml and SaviU/ml with the following result:

| UF-concentrate | S-CEVU/ml | SaviU/ml |
|---|---|---|
| 9.25 ml | 570 | 41 |

Purification:

2 ml of the UF-concentrate was diluted 5 times to lower the ionic strength and filtered through 0.22 µm disk filter. This sample was applied to a Mono Q® HR5/5 Pharmacia column, equilibrated with 50 mM Tris/HCl buffer, pH 7.5, (buffer A) and a flow of 1 ml/min. After wash to baseline, with buffer A, the column was eluted with a Tris/HCl buffer, pH 7.5, containing 1 M NaCl (buffer B), the elution gradient was 0–50% buffer B in 1 hour.

After 36 min. a peak complex showed up, 1 ml fractions were picked up and the first 10 fractions showed cellulase activity on CMC/Agarose/congo-red plates.

These fractions were pooled and concentrated, by ultra-filtration on AMICON cells using a DOW membrane GR61PP with cut-off 20 kD, to 3 ml.

This sample was applied to a HiLoad 26/60 Superdex 75™ prep grade Pharmacia column, equilibrated with 100 mM Na-Acetate buffer, pH 6.35, and a 1 ml/min flow.

After 82 min. a peak showed up, 1 ml fractions were picked up and the first 10 fractions showed cellulase activity on CMC/Agarose/congo-red plates.

These fractions were pooled and the following results were obtained:

$A_{280}$=0.15

$A_{280}/A_{260}$=1.62

Mw(SDS)=22 kD pI=3.5–5

Purity on SDS-PAGE=100%

S-CEVU/ml=28.5

S-CEVU/$A_{280}$=188

S-CEVU/mg=436

Extinction coefficient=54880 (calculated)

Mw(calculated)=22 kD

The Extinction coefficient is based on the content of tyrosine, tryptophane and cystein calculated from the sequence of SEQ ID No. 2 (the amino acid sequence). SDS-Page was performed on NOVEX Pre-Cast Gels 4–20% Tris-Glycine Gel 1.0 mm×10 Well IEF was performed on Pharmacia PAGplate pH 3.5–9.5, the activity was visualized by CMC-Congored overlaying.

Determination of $K_M$ & $k_{cat}$: $k_m$ and $k_{cat}$ was determined in the same manner as the determination of SAVI Units at pH 8.5 with a substrate concentration up to 8 g/l.

The following results were obtained:

$k_{cat}$ 38 per sec.

$k_m$ 5 g/l, phosporic acid swollen cellulose, pH 8.5.

Specific activity on CMC at pH 7.5:

436 S-CEVU per mg protein.

D. Determination of pH and Temperature Profile of the Endoglucanase from *M. thermophila*

The pH profile was determined at the following conditions: Buffers of pH values between 2.5 and 10.0 were made by mixing 0.1M Tri-sodium phosphate with 0.1M citric acid. Purified endoglucanase was diluted to ensure the assay response to be within the linear range of the assay. The substrate was a 0.4% suspension of AZCL-HE-cellulose (MegaZyme) mixed 1:1 with the citrate/phosphate buffer to a final substrate concentration of 0.2% AZCL-HE-cellulose. 1 ml substrate in Eppendorf® 1.5 ml polypropylene tubes were added 10 µl of enzyme solution and incubated for 15 minutes in Eppendorf® temperature controlled Thermomixers before heat-inactivation of enzymes for 20 minutes at 95° C. in a separate Thermomixer. The tubes were centrifuged and 200 µl of each supernatant was transferred to a well in a 96 well microtiter plate and OD was measured at 620 nm in an ELISA reader (Labsystems Multiskan® MCC/340).

For the pH optimum incubations took place at 30° C. For each pH value, three tubes were added enzyme and incubated before heat-inactivation, whereas one tube (the blank) was added enzyme and heat-inactivated immediately. The mean value of the three incubated samples was calculated and the blank value was substracted.

The following pH profile was determined:

| pH | Relative Activity |
|---|---|
| 2.5 | <10% |
| 3 | <10% |
| 3.5 | 22% |
| 4 | 87% |
| 4.5 | 89% |
| 5 | 100% |
| 6 | 94% |
| 6.5 | 86% |
| 7 | 78% |
| 7.5 | 73% |
| 8 | 68% |
| 8.5 | 54% |
| 9 | 31% |
| 10 | 18% |

It is seen that the endoglucanase has more than 60% activity between pH 4.0 and 8.0 and optimal activity at pH 5.0–6.0.

Temperature Profile:

The temperature optimum was determined in the same manner at pH 5.5. The temperatures ranged from 30° C. to 80° C. For each temperature three incubations were carried out and the mean calculated. Three blanks were produced by immediate heat-inactivation of enzyme and the mean was subtracted from the incubated sample values.

It is seen that the endoglucanase has optimal activity at 50–70° C.

| | Temp (° C.) | | | | | |
|---|---|---|---|---|---|---|
| | 30 | 40 | 50 | 60 | 70 | 80 |
| Relative Activity | 74% | 77% | 99% | 100% | 93% | 62% |

The temperature stability was determined in the same manner at pH 5.5 and 30° C., and, further, the enzyme solutions were preheated for 1 hour at the actual temperature and cooled on ice. The residual activity is shown below in % of the activity of a non-preheated enzyme sample:

| | Temp. (° C.) | | | | |
|---|---|---|---|---|---|
| | 40 | 50 | 60 | 70 | 80 |
| Relative Activity | 95% | 84% | 92% | 86% | 24% |

E. Color Clarification of Myceliophthora Cellulase (SEQ ID No. 2) Measured as Removal of Surface Fibrils and Fibers Protruding from the Yarn of a Textile Containing Cellulosic Fibers

| Apparatus | Terg-o-tometer |
|---|---|
| Liquid volume | 100 ml |
| Agitation | 150 movements/min with vertical stirrer |
| Rinse time | 5 min in tapwater |
| Washing temp | 40° |
| Washing liqour | 0.05 M phosphate buffer |
| pH | 7.0 |
| Washing time | 30 min |
| Repetitions | 2 |
| Enzymes | Myceliophthora SEQ ID No. 2 |
| Dosage | 500 and 2500 S-CEVU/l |
| Textile | 2 swatches of aged black 100% cotton 5 × 6 cm (0.9 gram) |
| Drying | Tumble dry |

Evaluation:

The light remission is measured by a Datacolor Elrepho Remission spectrophotometer. Remission is calculated as delta L (Hunter Lab-values). When the surface fibrils and fibers protruding from the yarn are removed by the cellulase, the surface of the black fabric appears darker, and lower L values are obtained.

The sample is compared with a blind sample, i.e. washed without enzyme:

| No cellulase | 500 ECU/l | 2500 ECU/l |
|---|---|---|
| 0.00 | −1.41 | −1.91 |

Delta L-values Compared to Blind Sample.

The data shows that Myceliophthora cellulase without CBD gives good color clarification under the conditions tested.

F. Construction of the Gene Fusions Between the Endoglucanase from Myceliophthora Thermophila and the 43 kD Endoglucanase from Humicola Insolens The purpose of the two constructions was to make derivatives of the endoglucanase from *M. thermophila* with the linker and CBD from the 43 kD endoglucanase from *H. insolens* (disclosed in WO 91/17243). The native endoglucanase from *M. thermophila* do not have a linker and/or a cellulose binding domain, CBD.

CM1: Construction 1 consist of the endoglucanase from *M. thermophila* (225 amino acids) and the 72 C-terminal amino acids from the *H. insolens* 43 kD endoglucanase.

CM2: Construction 2 consist of the endoglucanase from *M. thermophila* (225 amino acids) and the 83 C-terminal amino acids from the *H. insolens* 43 kD endoglucanase.

The 43 kD endoglucanase cDNA from *H. insolens* was cloned into pHD414 in such a way that the endoglucanase gene was transcribed from the Taka-promoter. The resulting plasmid was named pCaHj418.

In a similar way the cDNA encoding the endoglucanase from *M. thermophila* was cloned into pHD414 and the resulting plasmid was named pA2C193.

Primers:
primer 1:
   5'-CGGAGCTCACGTCCAAGAGCGGCTGCTCCCG-TCCCTCCAGCAGCACCAGCTCTCCGG-3' (SEQ ID NO:88)
primer 2:
   5'-CCGGAGAGCTGGTGCTGCTGGAGGGACGGGA-GCAGCCGCTCTTGGACGTGAGCTCCG-3' (SEQ ID NO:89)
primer 3:
   5'-CGGAGCTCACGTCCAAGAGCGGCTGCTCCCGT-AACGACGACGGCAACTTCCCTGCCG-3' (SEQ ID NO:90)
primer 4:
   5'-CGGCAGGGAAGTTGCCGTCGTCGTTACGGGA-GCAGCCGCTCTTGGACGTGAGCTCCG-3' (SEQ ID NO:91)
Taka-pro. primer: 5' CAACATCACATCAAGCTCTCC-3' (SEQ ID NO:92)
AMG-term. primer: 5' CCCCATCCTTTAACTATAGCG-3' (SEQ ID NO:93)

The endoglucanase fusions were constructed by the PCR overlap-extension method as described by Higuchi et al. 1988.

Construction 1:
   Reaction A: The Polymerase Chain Reaction (PCR) was used to amplify the fragment of pCaHj418 between primer 1 and AMG-term. primer (the linker and CBD from the 43 kD endoglucanase from *H. insolens*).
   Reaction B: PCR amplification of the fragment between Taka-pro. primer and primer 2 in pA2C193, the endoglucanase gene from *M. thermophila*.
   Reaction C: The two purified fragments were used in a third PCR in the presence of the primers flanking the total region, i.e. Taka-pro. primer and AMG-term. primer.

Construction 2:
   The same procedure was used where primer 3 and primer 4 had replaced respectively primer 1 and primer 2.

The fragment amplified in reaction C was purified, digested with restriction enzymes Xba I and BsstE II. The purified digested fragment was ligated into pA2C193 digested with restriction enzymes Xba I and BsstE II.

Competent cells from *E. coli* strain DH5αF' (New England Biolabs.) were transformed with the ligated plasmid and colonies containing the gene fusion were isolated. The sequence of the cloned part was verified by DNA sequencing.

The sequence of the re shown in SEQ ID No. 3 and SEQ ID No. 5.

Polymerase Chain Reactions were carried out under standard conditions, as recommended by Perkin-Elmer.

Reaction A and B started with 2 min. at 94° C. followed by 20 cycles of (30 sec. at 94° C., 30 sec. at 50° C. and 1 min. at 72° C.) and end with 4 min. at 72° C.

Reaction C started with (2 min. at 94° C., 1 min. at 52° C. and 2 min. at 72° C.), followed by 15 cycles of (30 sec. at 94° C., 30 sec. at 52° C. and 90 sec. at 72° C.) and end with 4 min. at 72° C.

The two constructs were transformed into Aspergillus oryzae as described above.

G. Purification and Characterisation of Cloned Cellulases with Cellulose Binding Domains The cloned product is recovered after fermentation by separation of the extracellular fluid from the production organism.

About one gram of cellulase is then highly purified by affinity chromatography using 150 gram of Avicel in a slurry with 20 mm Sodium-phosphate pH 7.5.

The Avicel is mixed with the crude fermentation broth which contain total about 1 gram of cellulase. After mixing at 4 C for 20 min the Avicel enzyme is packed into a column with a dimension of 50 times 200 mm about 400 ml total.

The column is washed with the 200 ml buffer, then washed with 0.5 M NaCl in the same buffer until no more protein elutes. Then washed with 500 ml 20 mm Tris pH 8.5. Finally the pure full length enzyme is eluted with 1% triethylamine pH 11.8.

The eluted enzyme solution is adjusted to pH 8 and concentrated using a Amicon cell unit with a membrane DOW GR61PP (polypropylene with a cut off of 20 KD) to above 5 mg protein per ml.

The purified cellulases were characterised as follow:

| | Mw SDS-PAGE | pI | Molar E.280 | S-CEVU per A.280 |
|---|---|---|---|---|
| Myceliophthora (SEQ ID No. 4) | 43 kD | 4 | 74.950 | 135 |
| Acremonium (SEQ ID No. 8) | 40 kD | 5 | 68.020 | 185 |
| Thielavia (SEQ ID No. 12) | 35 kD | 4.3 | 52.470 | 75 |

| | pH Activity above 50% | N-terminal | Thermostability DSC |
|---|---|---|---|
| Myceliophthora (SEQ ID No. 4) | 5.0–9.0 | Blocked. | 80° C. |
| Acremonium (SEQ ID No. 8) | 6.0–9.5 | Blocked. | 61° C. |
| Thielavia (SEQ ID No. 12) | 5.0–9.0 | ASGSG - - - | 83° C. |

The purified cellulases was analysed for MW by SDS-PAGE and using standard LMW protein marker kit from Pharmacia the MW was calculated for the cellulases. The MW is apparently higher than the MW of the composition of the coding amin acids and is due to the fact the linker region are O-glycosylated resulting in this higher MW. The pI was determined using a Pharmacia Ampholine PAG plates pH 3.5 to 9.5 and again using a Pharmacia kit with known pI proteins.

The molar extinction coefficient was calculated based on the amin acids composition using the known absorbance of Tryptophan, Tyrosine and Cystein.

pH activity profile was obtained using CMC substrate, incubation for 20 min at 40° C. at a 0.5 pH interval and measuring the formation of reducing sugars. The relative activity at the different pH was calculated and the table contain the interval with more than 50% relative activity has been measured.

The N-terminal was determined for the purified cellulase using a Applied Biosystems model 473A sequencer. The protein sequenceer was run according to the manufacturer instructions.

Two of the cellulases were blocked, this is due to the N-terminal glutamine which form a pyroglutamate which can not be detected and which block for further sequencing.

DSC Differential scanning calometry was done at neutral pH (7.0) using a MicroCalc Inc. MC calorimeter with a constant scan rate and raising the temperature from 20 to 90° at a rate of 90° per hour.

Raising antibody. The cellulases from Myceliophthora, Acremonium and Thielavia were used for raising antibody in rabbits. 0.1 mg of the purified cellulase in 0.9% NaCl solution mixed with Freunds adjuvant immediately prior to injection. The rabbits were immunized 10 times with one week interval. The immunoglobulin G fraction (IgG) was purified by ammonium sulfate precipitation (25% saturation). The precipitate was solubilized in water and then dialyzed extensively against sodium acetate buffer (pH 5.0, 50 mM) altering with deionized water. After filtration, the IgG fraction was stabilized with sodium azide (0.01%).

Using immunodiffusion in agar plates all three cellulases form a single immunoprecipitate with its homologous antiserum and no precipitate was seen between the 3 cloned cellulases and the sera raised against the other two cellulases.

H-I. Performance of Endoglucanase of Construction 1 (SEQ ID No. 3) Measured in Buffer as Removal of Surface Fibrils and Fibers Protruding from the Yarn of a Textile Containing Cellulosic Fibers

| Apparatus | Terg-o-tometer |
|---|---|
| Liquid volume | 100 ml |
| Agitation | 150 movements/min (rpm) |
| Rinse time | 5 min in tap water |
| Washing temp | 40° C. |
| Water Hardness | 1 mM $CaCl_2$ |
| Washing liquor | 0.05 M phosphate buffer |
| pH | 7.0 |
| Washing time | 30 min |
| Repetitions | 2 |
| Textile | 2 swatches of aged black, 100% cotton 5 × 6 cm |
| Drying | Tumble dry |

Evaluation:

The light remission was measured by a Macbeth Color Eye 7000 Remission spectrophotometer. Remission is calculated as delta L (Hunter Lab-values). When the surface fibrils and fibers protruding from the yarn were removed by the cellulase, the surface appeared more bright, and lower L values were obtained.

Results:

| S-CEVU/l | 0 | 250 | 1000 |
|---|---|---|---|
| Inventive enzyme | 0 | −1.4 | −1.6 |

The data show that the enzyme of the invention gives very good color clarification under the conditions tested.

H-II. Performance of Cloned Endoglucanase from *Thielavia terrestris* (SEQ ID No. 12) in Buffer Measured as Removal of Surface Fibrils and Fibers Protruding from the Yarn of a Textile Containing Cellulosic Fibers

| Apparatus | Terg-o-tometer |
|---|---|
| Liquid volume | 100 ml |

-continued

| | |
|---|---|
| Agitation | 150 movements/min with vertical stirrer |
| Rinse time | 10 min in tapwater |
| Washing temp | 40° |
| Washing liqour | 0.05 M phosphate buffer. |
| pH | 7.0 |
| Washing time | 30 min |
| Repetitions | 2 |
| Textile | 2 swatches of aged black cotton 5 × 6 cm (app. 150 g/m$^2$) |
| Drying | Tumble dry |

Evaluation:

The light remission was measured by a Datacolor Elrepho Remission spectrophotometer. Remission is calculated as delta L (Hunter Lab-values). When the surface fibrils and fibers protruding from the yarn are removed by the cellulase, the surface of the black fabric appears darker and nicer, and lower L values are obtained.

Results:

| S-CEVU/l | 0 | 50 | 200 |
|---|---|---|---|
| Inventive enzyme | 0 | −0.66 ± 0.10 | −1.3 ± 0.06 |

The data show that the cellulase gives good color clarification under the conditions tested.

H-III. Performance of Endoglucanase of *Volutella colletrichoides* (SEQ ID No. 22) Measured in Buffer as Removal of Surface Fibrils and Fibers Protruding from the Yarn of a Textile Containing Cellulosic Fibers

| | |
|---|---|
| Apparatus | Terg-o-tometer |
| Liquid volume | 100 ml |
| Agitation | 150 movements/min with vertical stirrer |
| Rinse time | 5 min in tapwater |
| Washing temp | 40° |
| Washing liqour | 0.05 M phosphate buffer |
| pH | 7.0 |
| Washing time | 30 min |
| Repetitions | 2 |
| Dosage | 2.5 S-CEVU/ml |
| Textile | 2 swatches of aged black 100% cotton 5 × 6 cm (0.9 gram) |
| Drying | Tumble dry |

Evaluation:

The light remission is measured by a Datacolor Elrepho Remission spectrophotometer. Remission is calculated as delta L (Hunter Lab-values). When the surface fibrils and fibers protruding from the yarn are removed by the cellulase, the surface of the black fabric appears darker, and lower L values are obtained.

The sample is compared with a blind sample, i.e. washed without enzyme:

No cellulase With cellulase
0.00–0.57

Delta L remission values compared to blind sample.

The data shows that the *Volutella colletrichoides* cellulase gives good color clarification under the conditions tested.

H-IV. Performance of Cloned Cellulases from *Thielavia terrestris* and Acremonium sp. CBS 478.94 in High pH Heavy Duty Detergent Measured as Removal of Surface Fibrils and Fibers Protruding from the Yarn of a Textile Containing Cellulosic Fibers

| | |
|---|---|
| Apparatus | Terg-o-tometer |
| Liquid volume | 150 ml |
| Agitation | 150 movements/min with vertical stirrer |
| Rinse time | 10 min in tapwater |
| Washing temp | 35° C. |
| Washing liqour | 1.0 g/l US type HDG (zeolite/soda built, anionic/nonionic weight ratio > 2.5) |
| pH | 10.0 |
| Hardness | 1.0 mM CaCl$_2$ 0.34 mM MgCl$_2$ |
| Washing time | 12 min |
| Repetitions | 6 |
| Textile | 2 swatches of aged black cotton 5 × 6 cm (app. 150 g/m$^2$) 2 swatches of heavy knitted cotton 5 × 6 cm (app. 600 g/m$^2$) |
| Drying | Tumble dry |

Evaluation:

The light remission is measured by a Datacolor Elrepho Remission spectrophotometer. Remission is calculated as delta L (Hunter Lab-values). When the surface fibrils and fibers protruding from the yarn are removed by the cellulase, the surface of the black fabric appears darker and nicer, and lower L values are obtained. Different dosages of cloned cellulases from *Thielavia terrestris* (SEQ ID No. 12) and Acremonium sp. CBS 478.94 (SEQ ID No.8), respectively, (denoted A and B, respectively) were tested.

Results:

| S-CEVU/l | 0 | 500 | 2000 |
|---|---|---|---|
| A | 0 | −2.0 ± 0.22 | −2.86 ± 0.19 |
| B | 0 | −0.6 ± 0.36 | −1.96 ± 0.23 |

The data show that both cellulases gives good color clarification under the conditions tested.

H-V. Performance of Cellulases Cloned from *Thielavia terrestris* and Acremonium sp. CBS 478.94, and Construction 1 (SEQ ID No. 3) Measured as Removal of Surface Fibrils and Fibers Protruding from the Yarn of a Textile Containing Cellulosic Fibers

| | |
|---|---|
| Apparatus | Terg-o-tometer |
| Liquid volume | 150 ml |
| Agitation | 150 movements/min with vertical stirrer |
| Rinse time | 10 min in tapwater |
| Washing temp | 35° C. |
| Hardness | 1.0 mM CaCl$_2$ 0.34 mM MgCl$_2$ |
| Washing liqour | 2.0 g/l HDL (neutral, citrate built HDL, with nonionic/anionic weight ration > 0.5) |
| pH | 7.5 |
| Washing time | 30 min |
| Repetitions | 2 |

-continued

| Textile | 2 swatches of aged black cotton 5 × 6 cm (app. 150 g/m²) |
| --- | --- |
| | 2 swatches of heavy knitted cotton 4 × 7 cm (app. 600 g/m²) |
| Drying | Tumble dry |

Evaluation:

The light remission is measured by a Datacolor Elrepho Remission spectrophotometer. Remission is calculated as delta L (CIE Lab-values). When the surface fibrils and fibers protruding from the yarn are removed by the cellulase, the surface of the black fabric appears darker and nicer, and lower L values are obtained. Three different dosages of cloned cellulases from *Thielavia terrestris* (SEQ ID No. 12) and Acremonium sp. CBS 478.94 (SEQ ID No. 8) and the construction 1 (SEQ ID No. 3), respectively, (denoted A and B and C, respectively) were tested. black fabric appears darker and nicer, and lower L values are obtained. Three different dosages of cloned cellulases from *Thielavia terrestris* (SEQ ID No. 9) and Acremonium sp. CBS 478.94 (SEQ ID No. 5) and the construction 1 (SEQ ID No. 2), respectively, (denoted A and B and C, respectively) were tested.

Results:

| S-CEVU/l | 0 | 100 | 200 | 400 |
| --- | --- | --- | --- | --- |
| A | 0 | −3.06 ± 0.24 | −3.15 ± 0.27 | −3.92 ± 0.26 |
| B | 0 | −1.75 ± 0.27 | −3.08 ± 0.32 | −3.51 ± 0.44 |
| C | 0 | −1.84 ± 0.39 | −1.70 ± 0.47 | −2.30 ± 0.61 |

The data show that all cellulases gives very good color clarification under the conditions tested.

I. Application of Endoglucanases from *Thielavia terrestris*, Acremonium sp. and Construction 1 (SEQ ID No. 2) in Denim Finishing Experimental Apparatus: Washing machine Wascator FL 120
Liquid volume: 20 L
Fabric: 1.1 kg denim fabric, 14½ oz 100% cotton
Desizing: 10 min, 55° C., pH 7
  50 ml Aquazyme 120L
  2.5 g/l Phosphate buffer
Abrasion: 2 hours;
  pH and temperature varied according to the following table:

| Enzyme SEQ ID | Activity | pH/temp | Buffer system |
| --- | --- | --- | --- |
| No. 3 | 1400 S-CEVU/g | 6/55° C. | 2.5 g/l phosphate buffer |
| No. 12 | 292 S-CEVU/g | 5/65° C. | 1 g/l citrate buffer |
| No. 8 | 782 S-CEVU/g | 7/45° C. | 2.5 g/l phosphate buffer |

Inactivation: 15 min, 80° C.
  1 g/l sodium carbonate
Rinses: Three rinse cycles of 5 min in cold tap water
Evaluation:
Abrasion: The remission from the fabric was determined at 420 nm using a Texflash 2000 as a measure of the abrasion level.

The results from the treatment of the denim fabric with different endoglucanases of the invention is shown in the following table:

| Enzyme | Dosage | Trial conditions | Abrasion (420 nm) |
| --- | --- | --- | --- |
| Blank | 0 S-CEVU/g textile | pH 6, 55° C. | 9.96 |
| SEQ ID No. 3 | 10 S-CEVU/g textile | pH 6, 55° C. | 14.37 |
| Blank | 0 S-CEVU/g textile | pH 5, 65° C. | 9.26 |
| SEQ ID No. 12 | 10 S-CEVU/g textile | pH 5, 65° C. | 16.86 |
| Blank | 0 S-CEVU/g textile | pH 7, 45° C. | 9.47 |
| SEQ ID No. 8 | 10 S-CEVU/g textile | pH 7, 45° C. | 14.08 |

All tested cellulases show excellent performance in denim finishing, although each enzyme is unique in its own way. When applying the enzyme corresponding to SEQ ID No. 3 for denim finishing it is possible to reach a high abrasion level with a minimum of strength loss. When treating denim with the enzyme corresponding to SEQ ID No. 12, a very high wash down can be reached which leaves the fabric with an almost bleached appearance. Denim finishing with the enzyme corresponding to SEQ ID No. 8 gives a high abrasion level at a low temperature optimum which makes it possible to reduce the processing temperature and save energy.

J. Use of Cloned Cellulases from Acremonium sp. and *Thielavia terrestris* for Biopolishing of Lyocell Fibers Lyocell fibers which are sold under the trade name Tencel are spun from wood pulp cellulose in a more environmentally friendly waterbased solvent than is the case for normal viscose production). However, the fibers have a tendency to fibrillate when they are processed into textiles which is seen on the surface and denoted "fuzz". By using cellulases it is possible to permanently remove the exposed and fuzzy fibers and significantly improve the look of the finished fabric, the treatment generally known as Biopolishing. The endoglucanases of the present invention are especially suited for the removal of Lyocell surface fibers.

MATERIALS AND METHODS

The textile substrate was either 100% woven or different kinds of jersey knitted dark blue Tencel. The dark colour and jersey knit was preferred in order to enhance the visual effects which simplifed the evaluation. A woven 70/30 Tencel/Rayon blend was also used to a lesser extent.

The assays were either performed in 200 ml scale using a Launder-o-meter or in the 20 l scale using a Wascator. The treatment time was 60 min at 55° C. in Wascator and 60–90 min in LOM. The buffer was 2 g/l sodium acetate adjusted to pH 5 with acetic acid. The fabric to liquid ratio was 1:10 but in the Launder-o-meter 20 steel balls with a diameter of 14 mm (11 g each) was used to obtain sufficient mechanical abrasion. The biopolishing was immediately followed by inactivation using 2 g/lit sodium carbonate at 80° C. for 15 min followed by rinsing in cold water.

The results were evaluated using a fuzz note scale from 1–5 were 1 is the fibrillated look of the starting material and 5 is a high quality look with no visible fibers on the surface. Since the performance of endocellulases is specific towards a surface treatment the weightloss is below 2% and is therefore not included in the evaluation. Two cellulases were evaluated: the cellulases cloned from Acremonium sp. (SEQ ID No. 8) and from *Thielavia terrestris* (SEQ ID No. 12).

The two cellulases are able to defibrillate both Tencel and Tencel blended fabrics. By using an endoglucanase of the invention, only small fibrils are removed rather than whole fibers such as is the case when using acid cellulase mixtures from Trichoderma. The strength loss of the treated fabric is threrefore kept at a minimum when using endoglucanases of the present invention.

The following dosages gave a superior defibrillation, i.e. fuzz note 4 or above:

15 S-CEVU/g fabric of cellulase from Acremonium sp (SEQ ID No. 8); and

10 S-CEVU/g fabric of cellulase from *Thelavia terrestris* (SEQ ID No. 12).

EXAMPLE 2

A New Cellulytic Enzyme was by Expression Cloning as well as by PCR Cloning Detected to be Produced by a Plant Pathogen, Isolated from Soy Bean Seeds and Identified as *Macrophomina phaseolina*.

Production of biomass for PCR and expression cloning procedures:

Isolate CBS 281.96 was grown in shake flask cultures on cellulose enriched potato dextrose broth, incubated for 5 days at 260C (shaking conditions: 150 rpm).

A. Cloning and Expression of an Endoglucanase from *Macrophomina phaseolina* mRNA was isolated from *Macrophomina phaseolina*, grown in a cellulose-containing fermentation medium with agitation to ensure sufficient aeration. Mycelia were harvested after 3–5 days' growth, immediately frozen in liquid nitrogen and stored at −80° C. A library from *Macrophomina phaseolina*, consisting of approx. $10^6$ individual clones was constructed in *E. coli* as described with a vector background of 1%.

Plasmid DNA from some of the pools was transformed into yeast, and 50–100 plates containing 250–400 yeast colonies were obtained from each pool.

Endoglucanase-positive colonies were identified and isolated on SC-agar plates with the AZCL HE cellulose assay. cDNA inserts were amplified directly from the yeast colonies and characterized as described in the Materials and Methods section above. The DNA sequence of the cDNA encoding the endoglucanase is shown in SEQ ID No. 13 and the corresponding amino acid sequence is shown in SEQ ID No. 14.

The cDNA is obtainable from the plasmid in DSM 10512.

Total DNA was isolated from a yeast colony and plasmid DNA was rescued by transformation of *E. coli* as described above. In order to express the endoglucanse in Aspergillus, the DNA was digested with appropriate restriction enzymes, size fractionated on gel, and a fragment corresponding to the endoglucanase gene was purified. The gene was subsequently ligated to pHD414, digested with appropriate restriction enzymes, resulting in the plasmid pA2C477.

After amplification of the DNA in *E. coli* the plasmid was transformed into *Aspergillus oryzae* as described above. Screening of the cDNA Library by Hybridization and Characterization of the Positive Clones.

Approximately 6000 colony forming units (c.f.u.) from the *Macrophomina phaseolina* cDNA library in *E. coli* was screened by colony hybridization using a random-primed $^{32}$P-labeled PCR product from *M. phaseolina* as probe. The PCR product was generated as described in the Materials and methods section. The positive cDNA clones were characterized by sequencing the ends of the cDNA inserts, and by determining the nucleotide seuence of the longest cDNA from both strands. The DNA sequence of the cDNA encoding the endoglucanase is shown in SEQ ID No. 13 and the corresponding amino acid sequence is shown in SEQ ID No. 14.

B. Construction of Gene Fusion Between the Endoglucanase from *Macrophomina phaseolina* and the 43 kD Endoglucanase from *Humicola insolens*

One construction was prepared in order to make a derivative of the endoglucanase from *M. phaseolina* with the linker and CBD from the 43 kD endoglucanase from *H. insolens* (disclosed in WO 91/17243). The native endoglucanase from *M. phaseolina* does not have a linker and/or a cellulose binding domain, CBD.

The construction consists of the endoglucanase from *M. phaseolina* (223 amino acids) and the 72 C-terminal amino acids from the *H. insolens* 43 kD endoglucanase (SEQ ID NO:24).

The 43 kD endoglucanase cDNA from *H. insolens* is cloned into pHD414 in such a way that the endoglucanase gene is transcribed from the Taka-promoter. The resulting plasmid is named pCaHj418.

The cDNA encoding the endoglucanase from *M. phaseolina* (SEQ ID NO:23) is cloned into pYES2.0 as a BstX I/Not I fragment and the resulting plasmid is named pC1C477.

Primers:

primer 1(SEQ ID NO:94): 5'-GGTCGCCCGGACTGGCTGTTCCCGTACCCC-CTCCAGCAGCACCAGCTCTCCGG-3' primer 2(SEQ ID NO:95): 5'-CCGGAGAGCTGGTGCTGCTGGAGGGGGTAC-GGGAACAGCCAGTCCGGGCGACC3' pYES2.0 F.HT primer (SEQ ID NO:96): 5' CGGACTACTAGCAGCTGTAATACG-3'

AMG-term. primer (SEQ ID NO:93): 5' CCCCATCCTTTAACTATAGCG-3'

The endoglucanase fusion is constructed by the PCR overlap-extension method as described by Higuchi et al. 1988.

Reaction A: The Polymerase Chain Reaction (PCR) is used to amplify the fragment of pCaHj418 between primer 1 and AMG-term. primer (the linker and CBD from the 43 kD endoglucanase from *H. insolens*).

Reaction B: PCR amplification of the fragment between pYES2.0 F.HT primer and primer 2 in pC1C477, the endoglucanase gene from *M. phaseolina*.

Reaction C: The two purified fragments are used in a third PCR in the presence of the primers flanking the total region, i.e. pYES2.0 F.HT primer and AMG-term. primer.

The fragment amplified in reaction C is purified, digested with restriction enzymes, e.g. Xba I and BamH I. The purified digested fragment is ligated into pHD414 digested with restriction enzymes, e.g. Xba I and BamH I.

Competent cells from *E. coli* strain DH5αF' (New England Biolabs) are transformed with the ligated plasmid and colonies containing the gene fusion are isolated. The sequence of the cloned part was verified by DNA sequencing.

Polymerase Chain Reactions are carried out under standard conditions, as recommended by Perkin-Elmer.

Reaction A and B start with 2 min. at 94° C. followed by 20 cycles of (30 sec. at 94° C., 30 sec. at 52° C. and 1 min. at 72° C.) and ends with 4 min. at 72° C.

Reaction C starts with (2 min. at 94° C., 1 min. at 52° C. and 2 min. at 72° C.), followed by 20 cycles of (30 sec. at 94° C., 30 sec. at 52° C. and 90 sec. at 72° C.) and ends with 4 min. at 72° C.

The construct may be transformed into *Aspergillus oryzae* as described above.

EXAMPLE 3

Cloning and Expression of an Endoglucanase from Acremonium sp. and *Sordaria fimicola*

Production of biomass for expression cloning procedures: Isolates CBS 478.94 and ATCC 52644, respectively, were grown in shake flask cultures on cellulose enriched potato dextrose broth, incubated for 5 days at 260C (shaking conditions: 150 rpm).

mRNA was isolated from Acremonium sp., CBS 478.94, and *Sordaria fimicola*, ATCC 52644, respectively, grown in a cellulose-containing fermentation medium with agitation to ensure sufficient aeration. Mycelia were harvested after 3–5 days' growth, immediately frozen in liquid nitrogen and stored at −80° C. Libraries from Acremonium sp., and *Sordaria fimicola*, respectively, each consisting of approx. $10^6$ individual clones were constructed in *E. coli* as described with a vector background of 1%.

Plasmid DNA from some of the pools from each library was transformed into yeast, and 50–100 plates containing 250–400 yeast colonies were obtained from each pool.

Endoglucanase-positive colonies were identified and isolated on SC-agar plates with the AZCL HE cellulose assay. cDNA inserts were amplified directly from the yeast colonies and characterized as described in the Materials and Methods section above.

The DNA sequence of the cDNA encoding the endoglucanase from Acremonium sp. is shown in SEQ ID No. 9 and the corresponding amino acid sequence is shown in SEQ ID No. 10. The cDNA is obtainable from the plasmid in DSM 10080.

The partial DNA sequence of the cDNA encoding the endoglucanase from *Sordaria fimicola* is shown in SEQ ID No. 25 (Nucleotide sequence of the 5'-end of the cDNA) and the corresponding amino acid sequence is shown in SEQ ID No. 26. The cDNA is obtainable from the plasmid in DSM 10576.

Total DNA was isolated from a yeast colony and plasmid DNA was rescued by transformation of *E. coli* as described above. In order to express the endoglucanase in Aspergillus, the DNA was digested with appropriate restriction enzymes, size fractionated on gel, and a fragment corresponding to the endoglucanase gene from Acremonium sp. and *Sordaria fimicola*, respectively, was purified. The genes were subsequently ligated to pHD414, digested with appropriate restriction enzymes, resulting in the plasmids pA2C371 and pA2C502, respectively.

After amplification of the DNA in *E. coli* the plasmids were transformed into *Aspergillus oryzae* as described above.

EXAMPLE 4

A. Cloning by PCR an Endoglucanase From *Crinipellis scabella*, CBS 280.96

Isolate CBS 280.96 was grown in static flask cultures, holding wheat bran medium (per flask: 300 g wheat bran added 450 ml salt solution), incubated for 6 days at 26C. After incubation the wheat bran was extracted with destilled water (300 ml per flask) and the extract tested for endoglucanase activity (0.1% AZCL-HE-Cellulose (megazyme) in 1% agarose (Litex agarose, Medinova). Activity was observed on the plates holding pH of 3.0, 7.0 and 9.5.

mRNA was isolated from Crinipellis scabella grown as describe above. Mycelia were harvested after 3–5 days' growth, immediately frozen in liquid nitrogen and stored at −80° C. A library from *Crinipellis scabella*, consisting of approx. $10^6$ individual clones was constructed in *E. coli* as described with a vector background of 1%.

Approximately 10 000 colony forming units (c.f.u.) from the *Crinipellis scabella* cDNA library in *E. coli* was screened by colony hybridization using a random-primed $^{32}$P-labeled PCR product from *C. scabella* as probe. The PCR product was generated as described in the Materials and methods section. The positive cDNA clones were characterized by sequencing the ends of the cDNA inserts, and by determining the nucleotide seuence of the longest cDNA from both strands.

The DNA sequence of the cDNA encoding the endoglucanase is shown in SEQ ID No. 15 and the corresponding amino acid sequence is shown in SEQ ID No. 16.

The cDNA is obtainable from the plasmid in DSM 10511.

Total DNA was isolated from a yeast colony and plasmid DNA was rescued by transformation of *E. coli* as described above. In order to express the endoglucanse in Aspergillus, the DNA was digested with appropriate restriction enzymes, size fractionated on gel, and a fragment corresponding to the endoglucanase gene was purified. The gene was subsequently ligated to pHD414, digested with appropriate restriction enzymes, resulting in the plasmid pA2C475.

After amplification of the DNA in *E. coli* the plasmid was transformed into *Aspergillus oryzae* as described above.

Construction of Two Gene Fusions Between the Endoglucanase From *Crinipellis scabella* and the Linker/CBD Region of the 43 kDa Endoglucanase From *Humicola insolens*.

The native endoglucanase from *Crinipellis scabella* neither has a linker nor a cellulose binding domain (CBD). In addition, the full-length cDNA contains an ATG start codon upstream from the endoglucanase encoding open reading frame (ORF), presumably resulting in scrambled translation initiation upon heterologous expression of the cDNA, such as in the yeast *Saccharomyces cerevisiae* and the filamentous fungus *Aspergillus oryzae*. Thus, two gene fusions between the endoglucanase from *Crinipellis scabella* and the linker/CBD region of the 43 kD endoglucanase from *Humicola insolens* (disclosed in WO 91/17243) has been constructed using splicing by overlap extension (SOE) (Horton et al, 1989).

Construction 1 consists of the cDNA encoding the 226-residue endoglucanase from *C. scabella* fused by PCR with the 3'-end cDNA of *H. insolens* coding for the linker and CBD region (72 amino acids) at the COOH-terminus of the *H. insolens* 43 kD endoglucanase. The second hybrid construct is identical to the abovementioned gene fusion, except that the first five residues from the putative signal peptide have been deleted by PCR resulting in a shorter signal, which starts with the second in-frame ATG start codon.

Plasmid Constructs

The plasmid pC1C475 contains the full-length cDNA from *C. scabella*, cloned into BstXI/NotI-cut yeast expression vector pYES 2.0, the plasmid pC1C144 contains the full-length cDNA from *H. insolens*, cloned into the BstXI site of pYES 2.0.

Splicing by Overlap Extension

Two PCR fragments encoding the core region of the endoglucanase from *C. scabella* were generated in PCR buffer (10 mM Tris-HCl, pH 8.3, 50 mM KCl, 1.5 mM MgCl$_2$, 0.01% gelatin; containing 200 μM each dNTP), using 50–100 ng of pC1C475 as template, and 250 pmol of the reverse primer (5'-GACCGGAGAGCTGGTGCTGCTGGAGGGTTTACGA-ACACAGCCCGAGATATTAGTG-3' (SEQ ID NO:97)) in two combinations with 300–350 pmol of each forward primer (forward no. 1 5'-CCCCAAGCTTGACTTGGAACCAATGGTCCATCC-3' (SEQ ID NO:98), forward no. 2 5'-CCCCAAGCTTCCATCCAAACATGCTTAAAACGCT-CG-3' (SEQ ID NO:99)), a DNA thermal cycler (Landgraf, Germany) and 2.5 units of Taq polymerase (Perkin-Elmer, Cetus, USA). Thirty cycles of PCR were performed using a cycle profile of denaturation at 94° C. for 1 min, annealing at 55° C. for 2 min, and extension at 72° C. for 3 min. The PCR fragment coding for the linker and CBD of the endoglucanase of *H. insolens* was generated in PCR buffer (10 mM Tris-HCl, pH 8.3, 50 mM KCl, 1.5 mM MgCl$_2$, 0.01% gelatin; containing 200 μM each dNTP) using 100 ng of the pC1C144 template, 250 pmol forward primer (5'-CACTAATATCTCGGGCTGTGTTCGTAAACCCTCCAG-CAGCACCAGCTCTCCGGTC-3' (SEQ ID NO:100)), 250 pmol of the pYES 2.0 reverse primer (5'-GGGCGTGAATGTAAGCGTGACATA-3' (SEQ ID NO:101)) a DNA thermal cycler (Landgraf, Germany) and 2.5 units of Taq polymerase (Perkin-Elmer, USA). Thirty cycles of PCR were performed as above. The PCR products were electrophoresed in 0.7% low gelling temperature agarose gels (SeaPlaque, FMC), the fragments of interest were excised from the gel and recovered by treatment with agarase (New England Biolabs, USA) according to the manufacturer's instructions, followed by phenol extraction and ethanol precipitation at −20° C. for 12 h by adding 2 vols of 96% EtOH and 0.1 vol of 3M NaAc.

The recombinant hybrid genes between the endoglucanase from *Crinipellis scabella* and the linker/CBD region of the 43 kD endoglucanase from *Humicola insolens* were generated by combining the overlapping PCR fragments from above (ca. 50 ng of each template) in two combinations in PCR buffer (10 mM Tris-HCl, pH 8.3, 50 mM KCl, 1.5 mM MgCl$_2$, 0.01% gelatin; containing 200 μM each dNTP). The SOE reaction was carried out using the DNA thermal cycler (Landgraf, Germany) and 2.5 units of Taq polymerase (Perkin-Elmer, Cetus, USA). Two cycles of PCR were performed using a cycle profile of denaturation at 94° C. for 1 min, annealing at 55° C. for 2 min, and extension at 72° C. for 3 min, the reaction was stopped, 250 pmol of each end-primer (forward no. 1 5'-CCCCAAGCTTGACTTGGMCCAATGGTCCATCC-3' (SEQ ID NO:98), forward no. 2 5'-CCCCAAGCTTCCATCCAAACATGCTTAAAACGCT-CG-3' (SEQ ID NO:99), reverse primer 5'-GGGCGTGAATGTAAGCGTGACATA-3' (SEQ ID NO:101)) was added to the reaction mixture, and an additional 30 cycles of PCR were performed using a cycle profile of denaturation at 94° C. for 1 min, annealing at 55° C. for 2 min, and extension at 72° C., for 3 min.

Construction of the Expression Cassettes for Heterologous Expression in *Aspergillus oryzae*

The PCR-generated, recombinant fragments were electrophoresed in a 0.7% low gelling temperature agarose gel (SeaPlaque, FMC), the fragments of interest were excised from the gel and recovered by treatment with agarase (New England Biolabs, USA) according to the manufacturer's instructions, followed by phenol extraction and ethanol precipitation at −20° C. for 12 h. The DNA fragments were digested to completion with HindIII and XbaI, and ligated into HindIII/XbaI-cleaved pHD414 vector followed by electroporation of the constructs into *E. coli* DH10B cells according to the manufacturer's instructions (Life Technologies, USA).

The nucleotide sequence of the resulting gene fusions were determined from both strands as described in the Materials and methods section, SEQ ID Nos. 17 and 19. The constructs may be transformed into *A. oryzae* as described.

EXAMPLE 5

PCR Facilitated Detection of Said Type of Cellulytic Enzyme From 46 Filamentous and Monocentric Fungi, Representing 32 Genera, From 23 Families, Belonging to 15 Orders of 7 Classes, Covering all in all Four Groups of the True Fungi: Ascomycetous, Basidiomycetous, Chytridiomycetous and *Zygomycetous Fungi*

5.1 Materials

1. *Diplodia gossypina* Cooke
   Deposit of Strain, Acc No: CBS 274.96
2. *Ulospora bilgramii* (Hawksw. et al.)
   Acc No of strain: NKBC 1444,
3. *Microsphaeropsis* sp
4. *Ascobolus stictoideus* Speg.
   Acc No of strain: Q026 (Novo Nordisk collection)
   Isolated from goose dung, Svalbard, Norway
5. *Saccobolus dilutellus* (Fuck) Sacc.
   Deposit of strain: Acc No CBS 275.96
6. *Penicillium verruculosum* Peyronel
   Ex on Acc No of species: ATCC 62396
7. *Penicillium chrysogenum* Thom
   Acc No of Strain: ATCC 9480
8. *Thermomyces verrucosus* Pugh et al
   Deposit of Strain, Acc No.: CBS 285.96
9. *Xylaria hypoxylon* L. ex Greville
   Deposit of Strain, Acc No: CBS 284.96
10. *Poronia punctata* (Fr.ex L.) Fr.
    Ref:A.Munk: Danish Pyrenomycete s,
    Dansk Botanisk Arkiv, Vol17,1 1957
11. *Nodulisporum* sp
    Isolated from leaf of *Camellia reticulatá* (Theaceae, Guttiferales),
    Kunming Botanical Garden, Yunnan Province, China
12. *Cylindrocarpon* sp
    Isolated from marine sample, the Bahamas
13. *Fusarium anguioides* Sherbakoff
    Acc No of strain: IFO 4467
14. *Fusarium poae* (Peck) Wr.
    Ex on Acc No of species: ATCC 60883
15. *Fusarium solani* (Mart.)Sacc.emnd.Snyd & Hans.
    Acc No of strain: IMI 107.511
16. *Fusarium oxysporum* ssp *lycopersici* (Sacc.)Snyd. & Hans.
    Acc No of strain: CBS 645.78
17. *Fusarium oxysporum* ssp *passiflora*
    Acc No of strain: CBS 744.79
18. *Gliocladium catenulatum* Gillman & Abbott
    Acc. No. of strain: ATCC 10523
19. *Nectria pinea* Dingley
    Deposit of Strain, Acc. No. CBS 279.96
20. *Sordaria macrospora* Auerswald
    Ex on Acc No of species: ATCC 60255

21. *Humicola grisea* Traeen
    ex on Acc No for the species: ATCC 22726
22. *Humicola nigrescens* Omvik
    Acc No of strain: CBS 819.73
23. *Scytalidium thermophilum* (Cooney et Emerson) Austwick
    Acc No of strain: ATCC 28085
24. *Thielavia thermophila* Fergus et Sinden (syn *Corynascus thermophilus*)
    Acc No of strain: CBS 174.70, IMI 145.136
25. *Cladorrhinum foecundissimum* Saccardo et Marchal
    Ex on Acc No of species: ATCC 62373
26. *Syspastospora boninensis*
    Acc No of strain: NKBC 1515 (Nippon University, profe Tubaki Collection)
27. *Chaetomium cuniculorurn* Fuckel
    Acc. No. of strain: CBS 799.83
28. *Chaetomium brasiliense* Batista et Potual
    Acc No of strain: CBS 122.65
29. *Chaetomium murorum* Corda
    Acc No of strain: CBS 163.52
30. *Chaetomium virescens* (von Arx) Udagawa
    Acc. No. of strain: CBS 547.75
31. Nigrospora sp
    Deposit of strain, Acc No: CBS 272.96
32. Nigrospora sp
    Isolated from:
33. *Diaporthe syngenesia*
    Deposit of strain, Acc No: CBS 278.96
34. *Colletotrichum lagenarium* (Passerini) Ellis et Halsted syn *Glomerella cingulata* var orbiculare Jenkins et Winstead
    Ex on acc No of species: ATCC 52609
35. *Exidia glandulosa* Fr.
    Deposit of Strain, Acc No: CBS 277.96
36. *Fomes fomentarius* (L.) Fr.
    Deposit of strain: Acc. No. CBS 276.96
37. Spongipellis (?)
    Deposit of Strain: Acc No CBS 283.96
38. *Rhizophlyctis rosea* (de Bary & Wor) Fischer
    Deposit of Strain: Acc No.: CBS 282.96
39. *Rhizomucor pusillus* (Lindt) Schipper syn: *Mucor pusillus*
    Acc No of strain: IFO 4578
40. *Phycomyces nitens* (Kunze) van Tieghem & Le Monnier
    Acc No of strain: IFO 4814
41. *Chaetostylum fresenii* van Tieghem & Le Monnier syn. *Helicostylum fresenii*
    Acc No of strain NRRL 2305
42. *Trichothecium roseum*, Acc No of strain: IFO 5372
43. Coniothecium sp
    Endophyte, isolated from leaf of flowering plant, Kunming, Yunnan, China
44. Deposit of strain, Acc No.: CBS 271.96
    Coelomycete, Isolated from leaf of *Artocarpus altilis* (Moraceae, Urticales), Christiana, Jamaica
45. Deposit of strain, Acc No.: CBS 273.96
    Coelomycete, isolated from leaf of *Pimenta dioica* (Myrtaceae, Myrtales), Dallas Mountain, Jamaica
46. Deposit of strain: CBS 270.96
    Coelomycete, isolated from leaf of *Pseudocalymma alliaceum* (Bignoniaceae, Solanales) growing in Dallas Mountain, Jamaica 5.2 Procedure
Maintenance of Strains and Production of Biomass:
The strains were maintained on agar in petrie dishes (9 cm) or on slants (see list of Media: PCA and PDA). 44 of the strains were grown in shake flasks under the following growth conditions: general fungal media as PC, PD and PB 9 or YPG (see list of media); incubation time from 3 to 9 days; temperature 26° C.; rpm between 150 and 175. Strain No 14 (*F. poae*) was grown on wheat bran for 15 days (26° C.; static). Strain No 38 was grown in dilute salt solution (DS/2), added 1 cm$^2$ pieces of autoclaved filter paper.
Activity Test:
Activity was tested on 0.1% AZCL-HE-Cellulose (Megazyme) plates (14 cm Petrie dishes), made up in 1% agarose (HSB, Litex Agarose, Medinova). All tests were done in triplicate, viz. AZCL-HE-Cellulose dissolved in three buffers, adjusted to pH 3, 7 or 9.5 (using various proportions of the following two ingredients Citric acid monohydrat, Merck art. No 100244 (21.0 g) dissolved in water, making a total of 1000 ml; 0.1M tri-Sodium dodecabrohydrate, Merck art.no. 6578 (38 g), dissolved in water, making a total of 1000 ml. The mixing is done immidiately before use.
Harvesting of Biomass:
The biomass was harvested by filtering (mesh adjusted to the growth of the fungus, the finest used for fungi which have highly sporulating mycelium as e.g. Fusarium spp.). The biomass on the filter was scraped into a sterile plastic bag and immidiately frozen (by submerging into liquid nitrogen).

5.3 Results
I. Using the PCR screening and amplification techniques described in Materials and Methods the following partial cDNA sequences were obtained:

*Saccobolus dilutellus* (Fuck) Sacc., CBS 275.96: SEQ ID No. 27 (and the deduced amino acid sequence in SEQ ID No. 28);

*Thermomyces verrucosus*, CBS 285.96: SEQ ID No. 29 (and the deduced amino acid sequence in SEQ ID No. 30);

*Xylaria hypoxylon*, CBS 284.96: SEQ ID No. 31 (and the deduced amino acid sequence in SEQ ID No. 32);

*Fusarium oxysporum* ssp *lycopersici*, CBS 645.78: SEQ ID No. 33 (and the deduced amino acid sequence in SEQ ID No. 34);

*Nectria pinea*, CBS 279.96: SEQ ID No. 35 (and the deduced amino acid sequence in SEQ ID No. 36);

*Humicola grisea*, ATCC 22726: SEQ ID No. 37 (and the deduced amino acid sequence in SEQ ID No. 38);

*Humicola nigrescens*, CBS 819.73: SEQ ID No. 39 (and the deduced amino acid sequence in SEQ ID No. 40);

*Cladorrhinum foecundissimum*, ATCC 62373: SEQ ID No. 41 (and the deduced amino acid sequence in SEQ ID No. 42);

*Syspastospora boninensis*, NKBC 1515: SEQ ID No. 43 (and the deduced amino acid sequence in SEQ ID No. 44);

Nigrospora sp., CBS 272.96: SEQ ID No. 45 (and the deduced amino acid sequence in SEQ ID No. 46);

*Chaetostylum fresenii*: SEQ ID No. 47 (and the deduced amino acid sequence in SEQ ID No. 48);

*Exidia glandulosa*, CBS 277.96: SEQ ID No. 49 (and the deduced amino acid sequence in SEQ ID No. 50);

Coniothecium sp.: SEQ ID No. 51 (and the deduced amino acid sequence in SEQ ID No. 52);

Deposition No. CBS 271.96: SEQ ID No. 53 (and the deduced amino acid sequence in SEQ ID No. 54);

Deposition No. CBS 270.96: SEQ ID No. 55 (and the deduced amino acid sequence in SEQ ID No. 56);

*Diplodia gossypina*, CBS 274.96: SEQ ID No. 57 (and the deduced amino acid sequence in SEQ ID No. 58);

*Ulospora bilgramii*, NKBC 1444: SEQ ID No. 59 (and the deduced amino acid sequence in SEQ ID No. 60);

*Penicillium verruculosum*, ATCC 62396: SEQ ID No. 61 (and the deduced amino acid sequence in SEQ ID No. 62);

*Poronia punctata*: SEQ ID No. 63 (and the deduced amino acid sequence in SEQ ID No. 64);

*Fusarium anguioides*, IFO 4467: SEQ ID No. 65 (and the deduced amino acid sequence in SEQ ID No. 66);

*Thielavia thermophila*, CBS 174.70: SEQ ID No. 67 (and the deduced amino acid sequence in SEQ ID No. 68);

*Chaetomium cuniculorum*, CBS 799.83: SEQ ID No. 69 (and the deduced amino acid sequence in SEQ ID No. 70);

*Chaetomium virescens*: SEQ ID No. 71 (and the deduced amino acid sequence in SEQ ID No. 72);

*Colletotrichum lagenarium*: SEQ ID No. 73 (and the deduced amino acid sequence in SEQ ID No. 74);

*Phycomyces nitens*: SEQ ID No. 75 (and the deduced amino acid sequence in SEQ ID No. 76); and

*Trichothecium roseum*: SEQ ID No. 77 (and the deduced amino acid sequence in SEQ ID No. 78);

II. Using the PCR screening and amplification techniques described in Materials and Methods partial cDNA encoding partially for the enzyme of the invention was obtained and the plasmid was deposited according to the Budapest Treaty:

*Escherichia coli*, DSM 10583, deposition date Mar. 13, 1996; cDNA from Trichothecium roseum;

*Escherichia coli*, DSM 10584, deposition date Mar. 13, 1996; cDNA from Syspastospora boninensis;

*Escherichia coli*, DSM 10585, deposition date Mar. 13, 1996; cDNA from Cheatomium murorum

*Escherichia coli*, DSM 10587, deposition date Mar. 13, 1996; cDNA from Sordaria fimicola;

*Escherichia coli*, DSM 10588, deposition date Mar. 13, 1996; cDNA from the unidentified strain CBS 273.96;

*Escherichia coli*, DSM 10586, deposition date Mar. 13, 1996; cDNA from Spongipellis sp.

Color Clarification of Crude Supernatants

During normal wash the fabric will often fade. However, the fabric appearance is improved and the original colours are much better preserved or maintained if the fabric is washed with a cellulase giving color clarification. Color clarification is measured as removal of surface fibrils and fibers protruding from the yarn of a textile containing cellulosic fibers.

| | |
|---|---|
| Apparatus | Terg-o-tometer |
| Liquid volume | 100 ml |
| Agitation | 150 movements/min with vertical stirrer |
| Rinse time | 5 min in tapwater |
| Washing temp | 40° |
| Washing liqour | 0.05 M phosphate buffer |
| pH | 7.0 |
| Washing time | 30 min |
| Repetitions | 2 |

-continued

| | |
|---|---|
| Enzymes | Crude supernatants from the strains shown below. |
| Dosage | Two dosages from: 200, 500, 1000 or 2500 S-CEVU/l |
| Textile | 2 swatches of aged black 100% cotton 5 × 6 cm (0.9 gram) |
| Drying | Tumble dry |

Evaluation:

The light remission is measured by a Datacolor Elrepho Remission spectrophotometer. Remission is calculated as delta L (Hunter Lab-values). When the surface fibrils and fibers protruding from the yarn are removed by the cellulase, the surface of the black fabric appears darker, and lower L values are obtained.

The samples are compared with a blind sample, i.e. washed without enzyme. Below is shown the delta L remission values compared to a blind sample.

REFERENCES

Background of the Invention:

1. GB-A-1368599
2. EP-A-0 307 564
3. EP-A-0 435 876
4. WO 91/17243
5. WO 91/10732
6. WO 91/17244
7. WO 95/24471
8. WO 95/26398
9. Methods in Enzymology, 1988, Vol. 160, p. 200–391 (edited by Wood, W. A. and Kellogg, S. T.).
10. Béguin, P., "Molecular Biology of Cellulose Degradation", Annu. Rev. Microbiol. (1990), Vol. 44, pp. 219–248.
11. Henrissat, B., "Cellulases and their interaction with cellulose", Cellulose (1994), Vol. 1, pp. 169–196.
12. T.-M. Enveri, "Microbial Cellulases" in W. M. Fogarty, Microbial Enzymes and Biotechnology, Applied Science Publishers, 183–224 (1983).
13. Béguin, P. and Aubert, J-P., "The biological degradation of cellulose", FEMS Microbiology Reviews 13 (1994) 25–58.
14. Sheppard, P. O., et al., "The use of conserved cellulase family-specific sequences to clone Cellulase homologue cDNAs from *Fusarium oxysporum*, Gene, (1994), Vol. 15, pp. 163–167.
15. Saloheimo, A., et al., "A novel, small endoglucnaase gene, egI5, from *Trichoderma reesei* isolated by expression in yeast", Molecular Microbiology (1994), Vol. 13(2), pp. 219–228.
16. van Arsdell, J. N. et al., (1987) Cloning, characterization, and expression in *Saccharomyces cerevisiae* of endoglucanase I from *Trichoderma reesei*, Bio/Technology 5: 60–64.
17. Penttilä, M. et al, (1986) Homology between cellulase gnees of *Trichoderma reesei*: complete nucleotide sequence of the endoglucanase I gene. *Gene* 45:253–263.
18. Saloheimo, M. et al, (1988) EGIII, a new endoglucanase from *Trichoderma reesei*: the characterization of both gene and enzyme. *Gene* 63:11–21.
19. Gonzalés, R., et al., "Cloning, sequence analysis and yeast expression of the egl1 gene from *Trichoderma longibrachiatum*", *Appl. Microbiol. Biotechnol.* (1992), Vol. 38, pp. 370–375.

20. Ooi, T. et al. "Cloning and sequence analysis of a cDNA for cellulase (FI-CMCase) from *Aspergillus aculeatus*" Curr. Genet. (1990), Vol. 18, pp. 217–222.
21. Ooi, T. et al, "Complete nucleotide sequence of a gene coding for *Aspergillus aculeatus* cellulase (FI-CMCase)" Nucleic Acids Research (1990), Vol. 18, No. 19, p. 5884.
22. Xue, G. et al., "Cloning and expression of multiple cellulase cDNAs fromthe anaerobic rumen fungus *Neocallimastix patriciarum* in *E. coli*, J. Gen. Microbiol. (1992), Vol. 138, pp. 1413–1420.
23. Xue, G. et al., "A novel polysaccharide hydrolase cDNA (celD) from *Neocallimastix patriciarum* encoding three multi-functional catalytical domains with high endoglucanase, cellobiohydrolase and xylanase activities", J. Gen. Microbiol. (1992), Vol. 138, pp. 2397–2403.
24. Zhou, L. et al., "Intronless celB from the anaerobic fungus *Neocallimastix patriciarum* encodes a modular family A endoglucanase", Biochem. J. (1994), Vol. 297, pp. 359–364.
25. Dalbøge, H. and Heldt-Hansen, H. P., "A novel method for efficient expression cloning of fungal enzyme genes", Mol. Gen. Genet. (1994), Vol. 243, pp. 253–260.
26. Ali, B. R. S. et al., "Cellulases and hemicellulases of the anaerobic fungus Piromyces constitute a multiprotein cellulose-binding complex and are encoded by multigene families", FEMS Microbiol. Lett. (1995), Vol. 125, No. 1, pp. 15–21.
27. DNA Data Bank of Japan (DDBJ).
28. Wang, H. Y. and Jones, R. W.: "Cloning, characterization and functional expression of an endoglucanase-encoding gene from the phytopathogenic fungus *Macrophomina phaseolina*", Gene, 158:125–128, 1995.
29. Wang, H. Y. and Jones, R. W.: "A unique endoglucanase-encoding gene cloned from the phytopathogenic fungus *Macrophomina phaseolina*", Appl. and Environm. Microbiology, 61:2004–2006, 1995.
30. B. Henrissat: Biochem. J., 280:309–316, 1991.
31. Schauwecker, F., Wanner, G., Kahmann, R.: "Filament-specific expression of a cellulase gene in the dimorphic fungus Ustilago maydis", 1995, Biological Chemistry Hoppe-Seyler, 376:617–625.
32. WO 93/20193
33. WO 94/21801
34. WO 94/26880
35. WO 95/02043

The Drawings:
1. Feng and Doolittle, 1987, J. Mol. Evol. 25: 351–360.
2. NIH Data Base (Entrez, version spring 1996) available on World Wide Web: (http://www3.ncbi.nlm.nih.gov/htbin/ef/entrezTAX).
3. Eriksson, O. E. & Hawksworth, D. L.: Systema Ascomycetum vol 12 (1993).
4. Júlich, W.: Higher Taxa of Basidiomycetes, Bibliotheca Mycologia 85, 485pp (1981).
5. O'Donnell, K.: Zygomycetes in culture, University of Georgia, U.S., 257pp (1979).
6. Hawksworth, D. L., Kirk, P. M., Sutton, B. C. and Pegler, D. N.: Dictionary of the fungi, International Mycological Institute, 616pp (1995);
7. Von Arx, J. A.: The genera of fungi sporulating in culture, 424pp (1981).

Detailed Description:
1. Ford et al., Protein Expression and Purification 2: 95–107, 1991.
2. Cunningham and Wells, Science 244, 1081–1085, 1989.
3. de Vos et al., Science 255: 306–312, 1992.
4. Smith et al., J. Mol. Biol. 224: 899–904, 1992.
5. Wlodaver et al., FEBS Lett. 309: 59–64, 1992.
6. Tomme, P. et al. "Cellulose-Binding Domains: Classification and Properties" in "Enzymatic Degradation of Insoluble Carbohydrates", John N. Saddler and Michael H. Penner (Eds.), ACS Symposium Series, No. 618, 1996.
7. WO 90/00609
8. WO 95/16782
9. Needleman, S. B. and Wunsch, C. D., Journal of Molecular Biology, 48: 443–453, 1970.
10. WO 94/14953
11. Sambrook, J., Fritsch, E. F. & Maniatis, T. 1989. Molecular Cloning: A Laboratory Manual. Cold Spring Harbor Lab., Cold Spring Harbor, N.Y.
12. Beaucage and Caruthers, *Tetrahedron Letters* 22 (1981), 1859–1869.
13. Matthes et al., *EMBO Journal* 3 (1984), 801–805.
14. U.S. Pat. No. 4,683,202
15. Saiki et al., *Science* 239 (1988), 487–491.
16. Hitzeman et al., *J. Biol. Chem.* 255 (1980), 12073–12080.
17. Alber and Kawasaki, *J. Mol. Appl. Gen.* 1 (1982), 419–434).
18. Young et al., in *Genetic Engineering of Microorganisms for Chemicals* (Hollaender et al, eds.), Plenum Press, New York, 1982).
19. U.S. Pat. No. 4,599,311
20. Russell et al., *Nature* 304 (1983), 652–654.
21. McKnight et al., *The EMBO J.* 4 (1985), 2093–2099
22. P. R. Russell, Gene 40, 1985, pp. 125–130.
23. U.S. Pat. No. 4,870,008
24. O. Hagenbuchle et al., *Nature* 289, 1981, pp. 643–646.
25. L. A. Valls et al., *Cell* 48, 1987, pp. 887–897.
26. WO 87/02670
27. M. Egel-Mitani et al., Yeast 6, 1990, pp. 127–137.
28. U.S. Pat. No. 4,546,082
29. EP 16 201
30. EP 123 294
31. EP 123 544
32. EP 163 529
33. WO 89/02463
34. WO 92/11378
35. U.S. Pat. No. 4,599,311
36. U.S. Pat. No. 4,931,373
37. U.S. Pat. No. 4,870,008
38. U.S. Pat. No. 5,037,743
39. U.S. Pat. No. 4,845,075
40. U.S. Pat. No. 4,931,373
41. Gleeson et al., *J. Gen. Microbiol.* 132, 1986, pp. 3459–3465.
42. U.S. Pat. No. 4,882,279
43. EP 272 277

44. EP 230 023
45. Malardier et al., 1989, Gene 78: 147–156.
46. WO 93/11249.
47. WO 94/14953.
48. WO 95/02043.
49. Horton, R. M., Hunt, H. D., Ho, S. N., Pullen, J. K., and Pease, L. R. (1989) *Gene* 77, 61–68
50. Dalbøge, H., and Heldt-Hansen, H. (1994) *Mol. Gen. Genet.* 243, 253–260
51. Christensen, T., Wøldike, H., Boel, E., Mortensen, S. B., Hjortshøj, K., Thim, L., and Hansen, M. T. (1988) *Bio/Technology* 6, 1419–1422
52. Sanger, F., Nicklen, S., and Coulson, A. R. (1977) *Proc. Natl. Acad. Sci. U. S. A.* 74, 5463–5467
53. Devereux, J., Haeberli, P., and Smithies, O. (1984) *Nucleic Acids Res.* 12, 387–395
54. Becker, D. M. & Guarante, L. 1991. Methods Enzymol. 194: 182–187.
55. Gubler, U. & Hoffman, B. J. 1983. Gene 25: 263–269.
56. R. Higuchi, B. Krummel, and R. K. Saiki (1988). A general method of in vitro preparation and specific mutagenesis of DNA fragments: study of protein and DNA interactions. Nucl. Acids Res. 16: 7351–7367.
57. Sanger, F., Nicklen, S. & Coulson, A. R. 1977. Proc. Natl. Acad. Sci. U. S. A. 74: 5463–5467.
58. N. Axelsen et al., *A Manual of Quantitative Immunoelectrophoresis*, Blackwell Scientific Publications, 1973, Chapters 2,3,4 and 23.

---

What is claimed is:

1. An enzyme preparation comprising an endoglucanase or endoglucanase core having a first amino acid sequence of SEQ ID NO:79 and a second amino acid sequence of SEQ ID NO:80 wherein,
   (a) in position 3 of the first sequence, the amino acid is Trp, Tyr or Phe;
   (b) in position 4 of the first sequence, the amino acid is Trp, Tyr or Phe;
   (c) in position 8 of the first sequence, the amino acid is Arg, Lys or His;
   (d) in position 9, 10, 12 and 14, respectively, of the first sequence, and in position 4 of the second sequence, the amino acid is any of the 20 naturally occurring amino acid residues, provided that, in the first amino acid sequence, (i) when the amino residue in position 12 is Ser, then the amino acid residue in position 14 is not Ser, and (ii) when the amino residue in position 12 is Gly, then the amino acid residue in position 14 is not Ala, wherein the endoglucanase is obtained from a strain selected from the group consisting of *Crinipellis scapella, Macrophomina phaseolina, Myceliophthora thermophila, Sordaria fimicola, Volutella colletotrichoides, Thielavia terrestris,* Acremonium sp., *Exidia glandulosa, Fomes fomentarius,* Spongipellis sp., *Rhizophlyctis rosea, Rhizomucor pusillus, Phycomyces niteus, Chaetostylum fresenii, Diplodia gossypina, Ulospora bilgramii, Saccobolus dilutellus, Penicillium verruculosum, Penicillium chrysogenum, Thermomyces verrucosus, Diaporthe syngenesia, Colletotrichum lagenarium,* Nigrospora sp., *Xylaria hypoxylon, Nectria pinea, Sordaria macrospora, Thielavia thermophila, Chaetomium mororum, Chaetomium virscens, Chaetomium brasiliensis, Chaetomium cunicolorum, Syspastospora boninensis, Cladorrhinum foecundissimum, Scytalidium thermophila, Gliocladium catenulatum, Fusarium oxysporum* ssp. *lycopersici, Fusarium oxysporum* ssp. *passiflora, Fusarium solani, Fusarium anguioides, Fusarium poae, Humicola nigrescens, Humicola grisea, Panaeolus retirugis, Trametes sanguinea, Schizophyllum commune, Trichothecium roseum,* Microsphaeropsis sp., *Acsobolus stictoideus* spej., *Poronia punctata,* Nodulisporum sp. and Cylindrocarpon sp.

2. The enzyme preparation of claim 1, wherein the amino acid residue in position 9 of the first sequence is selected from the group consisting of proline, threonine, valine, alanine, leucine, isoleucine, phenylalanine, glycine, cysteine, asparagine, glutamine, tyrosine, serine, methionine and tryptophan.

3. The enzyme preparation of claim 1, wherein the amino acid residue in position 10 of the first sequence is selected from the group consisting of proline, threonine, valine, alanine, leucine, isoleucine, phenylalanine, glycine, cysteine, asparagine, glutamine, tyrosine, serine, methionine and tryptophan.

4. The enzyme preparation of claim 1, wherein the amino acid residue in position 12 of the first sequence is selected from the group consisting of proline, threonine, valine, alanine, leucine, isoleucine, phenylalanine, glycine, cysteine, asparagine, glutamine, tyrosine, serine, methionine and tryptophan.

5. The enzyme preparation of claim 1, wherein the amino acid residue in position 14 of the first sequence is selected from the group consisting of proline, threonine, valine, alanine, leucine, isoleucine, phenylalanine, glycine, cysteine, asparagine, glutamine, tyrosine, serine, methionine, tryptophan, glutamic acid and aspartic acid.

6. The enzyme preparation of claim 1, wherein the amino acid residue in position 4 of the second sequence is selected from the group consisting of proline, threonine, valine, alanine, leucine, isoleucine, phenylalanine, glycine, cysteine, asparagine, glutamine, tyrosine, serine, methionine, tryptophan, glutamic acid and aspartic acid.

7. The enzyme preparation of claim 1, wherein, in the first sequence, the amino acid residue in position 3 is tyrosine; or the amino acid residue in position 4 is tryptophan; or the amino acid residue in position 8 is lysine.

8. The enzyme preparation of claim 1, wherein the first sequence comprises an amino acid sequence selected from the group consisting of SEQ ID NO:102 and SEQ ID NO:103.

9. The enzyme preparation of claim 1 further comprising a cellulose-binding domain (CBD) of a 43 kD endoglucanase from *Humicola insolens.*

10. A method of providing colour clarification of laundry, which method comprising treating the laundry with a soaking, washing or rinsing liquor comprising an enzyme preparation of claim 1.

11. A laundry composition comprising the enzyme preparation of claim 1, and a compound selected from the group consisting of a surfactant, a builder compound, and a fabric softening agent.

* * * * *

UNITED STATES PATENT AND TRADEMARK OFFICE
CERTIFICATE OF CORRECTION

| | | |
|---|---|---|
| PATENT NO. | : 6,387,690 B1 | Page 1 of 1 |
| APPLICATION NO. | : 09/229911 | |
| DATED | : May 14, 2002 | |
| INVENTOR(S) | : Martin Schulein et al. | |

It is certified that error appears in the above-identified patent and that said Letters Patent is hereby corrected as shown below:

On the cover page, item (62), insert
--which is a continuation of PCT/DK96/00105 filed March 18, 1996--.

On column 1, line 5, after "6,001,639", delete "and" and insert --which is a continuation of international application no. PCT/DK96/00105 filed March 18, 1996, which--.

Signed and Sealed this

Thirty-first Day of August, 2010

David J. Kappos
*Director of the United States Patent and Trademark Office*